US010582973B2

(12) United States Patent
Wilson et al.

(10) Patent No.: US 10,582,973 B2
(45) Date of Patent: Mar. 10, 2020

(54) ROBOTIC SURGICAL DEVICES, SYSTEMS, AND RELATED METHODS

(71) Applicant: Virtual Incision Corporation, Lincoln, NE (US)

(72) Inventors: John Wilson, Brooklyn, NY (US); Jeff Shasho, Brooklyn, NY (US); Nishant Kumar, Bergenfield, NJ (US); Matt Mahin, Longmont, CO (US); Chris Santoro, Brooklyn, NY (US); Erik Mumm, Longmont, CO (US); Jason Herman, East Northport, NY (US); Shane Farritor, Lincoln, NE (US)

(73) Assignee: Virtual Incision Corporation, Lincoln, NE (US)

( * ) Notice: Subject to any disclaimer, the term of this patent is extended or adjusted under 35 U.S.C. 154(b) by 609 days.

(21) Appl. No.: 13/833,605

(22) Filed: Mar. 15, 2013

(65) Prior Publication Data
US 2014/0046340 A1    Feb. 13, 2014

Related U.S. Application Data

(60) Provisional application No. 61/680,809, filed on Aug. 8, 2012.

(51) Int. Cl.
*A61B 34/30* (2016.01)
*A61B 90/30* (2016.01)
(Continued)

(52) U.S. Cl.
CPC .............. *A61B 34/30* (2016.02); *A61B 34/37* (2016.02); *A61B 90/30* (2016.02); *A61B 90/361* (2016.02);
(Continued)

(58) Field of Classification Search
CPC ... A61B 6/4458; A61B 19/2203; A61B 18/12; A61B 19/5212; A61B 5/00; A61B 19/20; A61M 1/0058
(Continued)

(56) References Cited

U.S. PATENT DOCUMENTS 3,870,264 A    3/1975  Robinson
3,989,952 A   11/1976  Timberlake et al.
(Continued)

FOREIGN PATENT DOCUMENTS

CN    1082821918    12/2012
DE    102010040405    3/2012
(Continued)

OTHER PUBLICATIONS

Definition of Individually. Dictionary.com, retrieved on Aug. 9, 2016; Retrieved from the Internet: <http://www.dictionary.com/browse/individually>.*
(Continued)

*Primary Examiner* — Gary Jackson
*Assistant Examiner* — Sebastian X Lukjan
(74) *Attorney, Agent, or Firm* — Davis, Brown, Koehn, Shors & Roberts, P.C.; Sean D. Solberg

(57) ABSTRACT

The embodiments disclosed herein relate to various medical device components, including components that can be incorporated into robotic and/or in vivo medical devices. Certain embodiments include various modular medical devices for in vivo medical procedures.

15 Claims, 36 Drawing Sheets

(51) Int. Cl.
  *A61B 34/37* (2016.01)
  *A61M 1/00* (2006.01)
  *A61B 34/20* (2016.01)
  *A61B 90/50* (2016.01)
  *A61B 90/00* (2016.01)

(52) U.S. Cl.
  CPC ....... *A61B 90/50* (2016.02); *A61B 2034/2051* (2016.02); *A61B 2034/2059* (2016.02); *A61B 2034/302* (2016.02); *A61M 1/0058* (2013.01)

(58) Field of Classification Search
  USPC .................................................. 606/1, 130
  See application file for complete search history.

(56) References Cited

U.S. PATENT DOCUMENTS

| | | |
|---|---|---|
| 4,246,661 A | 1/1981 | Pinson |
| 4,258,716 A | 3/1981 | Sutherland |
| 4,278,077 A | 7/1981 | Mizumoto |
| 4,538,594 A | 9/1985 | Boebel et al. |
| 4,568,311 A | 2/1986 | Miyaki |
| 4,623,183 A | 11/1986 | Amori |
| 4,736,645 A | 4/1988 | Zimmer |
| 4,771,652 A | 9/1988 | Zimmer |
| 4,852,391 A | 8/1989 | Ruch et al. |
| 4,896,015 A | 1/1990 | Taboada et al. |
| 4,897,014 A | 1/1990 | Tietze |
| 4,922,755 A | 5/1990 | Oshiro et al. |
| 4,922,782 A | 5/1990 | Kawai |
| 4,990,050 A | 2/1991 | Tsuge et al. |
| 5,019,968 A | 5/1991 | Wang et al. |
| 5,108,140 A | 4/1992 | Bartholet |
| 5,172,639 A | 12/1992 | Wiesman et al. |
| 5,176,649 A | 1/1993 | Wakabayashi |
| 5,178,032 A | 1/1993 | Zona et al. |
| 5,187,032 A | 2/1993 | Sasaki et al. |
| 5,187,796 A | 2/1993 | Wang et al. |
| 5,195,388 A | 3/1993 | Zona et al. |
| 5,201,325 A | 4/1993 | McEwen et al. |
| 5,217,003 A | 6/1993 | Wilk |
| 5,263,382 A | 11/1993 | Brooks et al. |
| 5,271,384 A | 12/1993 | McEwen et al. |
| 5,284,096 A | 2/1994 | Pelrine et al. |
| 5,297,443 A | 3/1994 | Wentz |
| 5,297,536 A | 3/1994 | Wilk |
| 5,304,899 A | 4/1994 | Sasaki et al. |
| 5,307,447 A | 4/1994 | Asano et al. |
| 5,353,807 A | 10/1994 | DeMarco |
| 5,363,935 A | 11/1994 | Schempf et al. |
| 5,382,885 A | 1/1995 | Salcudean et al. |
| 5,441,494 A | 1/1995 | Oritz |
| 5,388,528 A | 2/1995 | Pelrine et al. |
| 5,436,542 A | 7/1995 | Petelin et al. |
| 5,458,131 A | 10/1995 | Wilk |
| 5,458,583 A | 10/1995 | McNeely et al. |
| 5,458,598 A | 10/1995 | Feinberg et al. |
| 5,471,515 A | 11/1995 | Fossum et al. |
| 5,515,478 A | 5/1996 | Wang |
| 5,524,180 A | 6/1996 | Wang et al. |
| 5,553,198 A | 9/1996 | Wang et al. |
| 5,562,448 A | 10/1996 | Mushabac |
| 5,588,442 A | 12/1996 | Scovil et al. |
| 5,620,417 A | 4/1997 | Jang et al. |
| 5,623,582 A | 4/1997 | Rosenberg |
| 5,624,380 A | 4/1997 | Shuichi et al. |
| 5,624,398 A | 4/1997 | Smith et al. |
| 5,632,761 A | 5/1997 | Smith et al. |
| 5,645,520 A | 7/1997 | Nakamura et al. |
| 5,657,429 A | 8/1997 | Wang et al. |
| 5,657,584 A | 8/1997 | Hamlin |
| 5,672,168 A | 9/1997 | de la Torre et al. |
| 5,674,030 A | 10/1997 | Sigel |
| 5,728,599 A | 3/1998 | Rosteker et al. |
| 5,736,821 A | 4/1998 | Suyama et al. |
| 5,754,741 A | 5/1998 | Wang et al. |
| 5,762,458 A | 6/1998 | Wang et al. |
| 5,769,640 A | 6/1998 | Jacobus et al. |
| 5,791,231 A | 8/1998 | Cohn et al. |
| 5,792,135 A | 8/1998 | Madhani et al. |
| 5,797,538 A | 8/1998 | Heaton et al. |
| 5,797,900 A | 8/1998 | Madhani et al. |
| 5,807,377 A | 9/1998 | Madhani et al. |
| 5,808,665 A | 9/1998 | Green |
| 5,815,640 A | 9/1998 | Wang et al. |
| 5,825,982 A | 10/1998 | Wright et al. |
| 5,841,950 A | 11/1998 | Wang et al. |
| 5,845,646 A | 12/1998 | Lemelson |
| 5,855,583 A | 1/1999 | Wang et al. |
| 5,876,325 A | 3/1999 | Mizuno et al. |
| 5,878,193 A | 3/1999 | Wang et al. |
| 5,878,783 A | 3/1999 | Smart |
| 5,895,417 A | 4/1999 | Pomeranz et al. |
| 5,906,591 A | 5/1999 | Dario et al. |
| 5,907,664 A | 5/1999 | Wang et al. |
| 5,910,129 A | 6/1999 | Koblish et al. |
| 5,911,036 A | 6/1999 | Wright et al. |
| 5,971,976 A | 10/1999 | Wang et al. |
| 5,993,467 A | 11/1999 | Yoon |
| 6,001,108 A | 12/1999 | Wang et al. |
| 6,007,550 A | 12/1999 | Wang et al. |
| 6,030,365 A | 2/2000 | Laufer |
| 6,031,371 A | 2/2000 | Smart |
| 6,058,323 A | 5/2000 | Lemelson |
| 6,063,095 A | 5/2000 | Wang et al. |
| 6,066,090 A | 5/2000 | Yoon |
| 6,102,850 A | 8/2000 | Wang et al. |
| 6,107,795 A | 8/2000 | Smart |
| 6,132,368 A | 10/2000 | Cooper |
| 6,132,441 A | 10/2000 | Grace |
| 6,139,563 A | 10/2000 | Cosgrove, III et al. |
| 6,156,006 A | 12/2000 | Brosens et al. |
| 6,159,146 A | 12/2000 | El Gazayerli |
| 6,162,171 A | 12/2000 | Ng et al. |
| D438,617 S | 3/2001 | Cooper et al. |
| 6,206,903 B1 | 3/2001 | Ramans |
| D441,076 S | 4/2001 | Cooper et al. |
| 6,223,100 B1 | 4/2001 | Green |
| D441,862 S | 5/2001 | Cooper et al. |
| 6,238,415 B1 | 5/2001 | Sepetka et al. |
| 6,240,312 B1 | 5/2001 | Alfano et al. |
| 6,241,730 B1 | 6/2001 | Alby |
| 6,244,809 B1 | 6/2001 | Wang et al. |
| 6,246,200 B1 | 6/2001 | Blumenkranz et al. |
| D444,555 S | 7/2001 | Cooper et al. |
| 6,286,514 B1 | 9/2001 | Lemelson |
| 6,292,678 B1 | 9/2001 | Hall et al. |
| 6,293,282 B1 | 9/2001 | Lemelson |
| 6,296,635 B1 | 10/2001 | Smith et al. |
| 6,309,397 B1 | 10/2001 | Julian et al. |
| 6,309,403 B1 | 10/2001 | Minor et al. |
| 6,312,435 B1 | 11/2001 | Wallace et al. |
| 6,321,106 B1 | 11/2001 | Lemelson |
| 6,327,492 B1 | 12/2001 | Lemelson |
| 6,331,181 B1 | 12/2001 | Tierney et al. |
| 6,346,072 B1 | 2/2002 | Cooper |
| 6,352,503 B1 | 3/2002 | Matsui et al. |
| 6,364,888 B1 | 4/2002 | Niemeyer et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,400,980 B1 | 6/2002 | Lemelson |
| 6,408,224 B1 | 6/2002 | Lemelson |
| 6,424,885 B1 | 7/2002 | Niemeyer et al. |
| 6,432,112 B2 | 8/2002 | Brock et al. |
| 6,436,107 B1 | 8/2002 | Wang et al. |
| 6,441,577 B2 | 8/2002 | Blumenkranz et al. |
| 6,450,104 B1 | 9/2002 | Grant et al. |
| 6,451,027 B1 | 9/2002 | Cooper et al. |
| 6,454,758 B1 | 9/2002 | Thompson et al. |
| 6,459,926 B1 | 10/2002 | Nowlin et al. |
| 6,463,361 B1 | 10/2002 | Wang et al. |
| 6,468,203 B2 | 10/2002 | Belson |
| 6,468,265 B1 | 10/2002 | Evans et al. |

(56) References Cited

U.S. PATENT DOCUMENTS

| | | |
|---|---|---|
| 6,470,236 B2 | 10/2002 | Ohtsuki |
| 6,491,691 B1 | 12/2002 | Morley et al. |
| 6,491,701 B2 | 12/2002 | Nemeyer et al. |
| 6,493,608 B1 | 12/2002 | Niemeyer et al. |
| 6,496,099 B2 | 12/2002 | Wang et al. |
| 6,508,413 B2 | 1/2003 | Bauer et al. |
| 6,512,345 B2 | 1/2003 | Borenstein |
| 6,522,906 B1 | 2/2003 | Salisbury, Jr. et al. |
| 6,544,276 B1 | 4/2003 | Azizi |
| 6,548,982 B1 | 4/2003 | Papanikolopoulos et al. |
| 6,554,790 B1 | 4/2003 | Moll |
| 6,565,554 B1 | 5/2003 | Niemeyer |
| 6,574,355 B2 | 6/2003 | Green |
| 6,587,750 B2 | 7/2003 | Gerbi et al. |
| 6,591,239 B1 | 7/2003 | McCall et al. |
| 6,594,552 B1 | 7/2003 | Nowlin et al. |
| 6,610,007 B2 | 8/2003 | Belson et al. |
| 6,620,173 B2 | 9/2003 | Gerbi et al. |
| 6,642,836 B1 | 11/2003 | Wang et al. |
| 6,645,196 B1 | 11/2003 | Nixon et al. |
| 6,646,541 B1 | 11/2003 | Wang et al. |
| 6,648,814 B2 | 11/2003 | Kim et al. |
| 6,659,939 B2 | 12/2003 | Moll et al. |
| 6,661,571 B1 | 12/2003 | Shioda et al. |
| 6,671,581 B2 | 12/2003 | Niemeyer et al. |
| 6,676,684 B1 | 1/2004 | Morley et al. |
| 6,684,129 B2 | 1/2004 | Salisbury, Jr. et al. |
| 6,685,648 B2 | 2/2004 | Flaherty et al. |
| 6,685,698 B2 | 2/2004 | Morley et al. |
| 6,687,571 B1 | 2/2004 | Byrne et al. |
| 6,692,485 B1 | 2/2004 | Brock et al. |
| 6,699,177 B1 | 3/2004 | Wang et al. |
| 6,699,235 B2 | 3/2004 | Wallace et al. |
| 6,702,734 B2 | 3/2004 | Kim et al. |
| 6,702,805 B1 | 3/2004 | Stuart |
| 6,714,839 B2 | 3/2004 | Salisbury, Jr. et al. |
| 6,714,841 B1 | 3/2004 | Wright et al. |
| 6,719,684 B2 | 4/2004 | Kim et al. |
| 6,720,988 B1 | 4/2004 | Gere et al. |
| 6,726,699 B1 | 4/2004 | Wright et al. |
| 6,728,599 B2 | 4/2004 | Wright et al. |
| 6,730,021 B2 | 5/2004 | Vassiliades, Jr. et al. |
| 6,731,988 B1 | 5/2004 | Green |
| 6,746,443 B1 | 6/2004 | Morley et al. |
| 6,764,441 B2 | 7/2004 | Chiel et al. |
| 6,764,445 B2 | 7/2004 | Ramans et al. |
| 6,766,204 B2 | 7/2004 | Niemeyer et al. |
| 6,770,081 B1 | 8/2004 | Cooper et al. |
| 6,774,597 B1 | 8/2004 | Borenstein |
| 6,776,165 B2 | 8/2004 | Jin |
| 6,780,184 B2 | 8/2004 | Tanrisever |
| 6,783,524 B2 | 8/2004 | Anderson et al. |
| 6,785,593 B2 | 8/2004 | Wang et al. |
| 6,788,018 B1 | 9/2004 | Blumenkranz |
| 6,792,663 B2 | 9/2004 | Krzyzanowski |
| 6,793,653 B2 | 9/2004 | Sanchez et al. |
| 6,799,065 B1 | 9/2004 | Niemeyer |
| 6,799,088 B2 | 9/2004 | Wang et al. |
| 6,801,325 B2 | 10/2004 | Farr et al. |
| 6,804,581 B2 | 10/2004 | Wang et al. |
| 6,810,281 B2 | 10/2004 | Brock et al. |
| 6,817,972 B2 | 11/2004 | Snow |
| 6,817,974 B2 | 11/2004 | Cooper et al. |
| 6,817,975 B1 | 11/2004 | Farr et al. |
| 6,820,653 B1 | 11/2004 | Schempf et al. |
| 6,824,508 B2 | 11/2004 | Kim et al. |
| 6,824,510 B2 | 11/2004 | Kim et al. |
| 6,832,988 B2 | 12/2004 | Sprout |
| 6,832,996 B2 | 12/2004 | Woloszko et al. |
| 6,836,703 B2 | 12/2004 | Wang et al. |
| 6,837,846 B2 | 1/2005 | Jaffe et al. |
| 6,837,883 B2 | 1/2005 | Moll et al. |
| 6,839,612 B2 | 1/2005 | Sanchez et al. |
| 6,840,938 B1 | 1/2005 | Morley et al. |
| 6,852,107 B2 | 2/2005 | Wang et al. |
| 6,858,003 B2 | 2/2005 | Evans et al. |
| 6,860,346 B2 | 3/2005 | Burt et al. |
| 6,860,877 B1 | 3/2005 | Sanchez et al. |
| 6,866,671 B2 | 3/2005 | Tierney et al. |
| 6,870,343 B2 | 3/2005 | Borenstein et al. |
| 6,871,117 B2 | 3/2005 | Wang et al. |
| 6,871,563 B2 | 3/2005 | Choset et al. |
| 6,879,880 B2 | 4/2005 | Nowlin et al. |
| 6,892,112 B2 | 5/2005 | Wang et al. |
| 6,899,705 B2 | 5/2005 | Niemeyer |
| 6,902,560 B1 | 6/2005 | Morley et al. |
| 6,905,460 B2 | 6/2005 | Wang et al. |
| 6,905,491 B1 | 6/2005 | Wang et al. |
| 6,911,916 B1 | 6/2005 | Wang et al. |
| 6,917,176 B2 | 7/2005 | Schempf et al. |
| 6,933,695 B2 | 8/2005 | Blumenkranz |
| 6,936,001 B1 | 8/2005 | Snow |
| 6,936,003 B2 | 8/2005 | Iddan |
| 6,936,042 B2 | 8/2005 | Wallace et al. |
| 6,943,663 B2 | 9/2005 | Wang et al. |
| 6,949,096 B2 | 9/2005 | Davison et al. |
| 6,951,535 B2 | 10/2005 | Ghodoussi et al. |
| 6,965,812 B2 | 11/2005 | Wang et al. |
| 6,974,411 B2 | 12/2005 | Belson |
| 6,974,449 B2 | 12/2005 | Niemeyer |
| 6,979,423 B2 | 12/2005 | Moll |
| 6,984,203 B2 | 1/2006 | Tartaglia et al. |
| 6,984,205 B2 | 1/2006 | Gazdzinski |
| 6,991,627 B2 | 1/2006 | Madhani et al. |
| 6,993,413 B2 | 1/2006 | Sunaoshi |
| 6,994,703 B2 | 2/2006 | Wang et al. |
| 6,994,708 B2 | 2/2006 | Manzo |
| 6,997,908 B2 | 2/2006 | Carrillo, Jr. et al. |
| 7,025,064 B2 | 4/2006 | Wang et al. |
| 7,027,892 B2 | 4/2006 | Wang et al. |
| 7,033,344 B2 | 4/2006 | Imran |
| 7,039,453 B2 | 5/2006 | Mullick |
| 7,042,184 B2 | 5/2006 | Oleynikov et al. |
| 7,048,745 B2 | 5/2006 | Tierney et al. |
| 7,053,752 B2 | 5/2006 | Wang et al. |
| 7,063,682 B1 | 6/2006 | Whayne et al. |
| 7,066,879 B2 | 6/2006 | Fowler et al. |
| 7,066,926 B2 | 6/2006 | Wallace et al. |
| 7,074,179 B2 | 7/2006 | Wang et al. |
| 7,077,446 B2 | 7/2006 | Kameda et al. |
| 7,083,571 B2 | 8/2006 | Wang et al. |
| 7,083,615 B2 | 8/2006 | Peterson et al. |
| 7,087,049 B2 | 8/2006 | Nowlin et al. |
| 7,090,683 B2 | 8/2006 | Brock et al. |
| 7,097,640 B2 | 8/2006 | Wang et al. |
| 7,105,000 B2 | 9/2006 | McBrayer |
| 7,107,090 B2 | 9/2006 | Salisbury, Jr. et al. |
| 7,109,678 B2 | 9/2006 | Kraus et al. |
| 7,118,582 B1 | 10/2006 | Wang et al. |
| 7,121,781 B2 | 10/2006 | Sanchez et al. |
| 7,125,403 B2 | 10/2006 | Julian et al. |
| 7,126,303 B2 | 10/2006 | Farritor et al. |
| 7,147,650 B2 | 12/2006 | Lee |
| 7,155,315 B2 | 12/2006 | Niemeyer et al. |
| 7,169,141 B2 | 1/2007 | Brock et al. |
| 7,182,025 B2 | 2/2007 | Ghorbel et al. |
| 7,182,089 B2 | 2/2007 | Ries |
| 7,199,545 B2 | 4/2007 | Oleynikov et al. |
| 7,206,626 B2 | 4/2007 | Quaid, III |
| 7,206,627 B2 | 4/2007 | Abovitz et al. |
| 7,210,364 B2 | 5/2007 | Ghorbel et al. |
| 7,214,230 B2 | 5/2007 | Brock et al. |
| 7,217,240 B2 | 5/2007 | Snow |
| 7,239,940 B2 | 7/2007 | Wang et al. |
| 7,250,028 B2 | 7/2007 | Julian et al. |
| 7,259,652 B2 | 8/2007 | Wang et al. |
| 7,273,488 B2 | 9/2007 | Nakamura et al. |
| 7,311,107 B2 | 12/2007 | Harel et al. |
| 7,339,341 B2 | 3/2008 | Oleynikov et al. |
| 7,372,229 B2 | 5/2008 | Farritor et al. |
| 7,447,537 B1 | 11/2008 | Funda et al. |
| 7,492,116 B2 | 2/2009 | Oleynikov et al. |
| 7,566,300 B2 | 7/2009 | Devierre et al. |
| 7,574,250 B2 | 8/2009 | Niemeyer |

(56) References Cited

U.S. PATENT DOCUMENTS

| | | |
|---|---|---|
| 7,637,905 B2 | 12/2009 | Saadat et al. |
| 7,645,230 B2 | 1/2010 | Mikkaichi et al. |
| 7,655,004 B2 | 2/2010 | Long |
| 7,670,329 B2 | 3/2010 | Flaherty et al. |
| 7,678,043 B2 | 3/2010 | Gilad |
| 7,731,727 B2 | 6/2010 | Sauer |
| 7,762,825 B2 | 7/2010 | Burbank et al. |
| 7,772,796 B2 | 8/2010 | Farritor et al. |
| 7,785,251 B2 | 8/2010 | Wilk |
| 7,785,333 B2 | 8/2010 | Miyamoto et al. |
| 7,789,825 B2 | 9/2010 | Nobis et al. |
| 7,794,494 B2 | 9/2010 | Sahatjian et al. |
| 7,865,266 B2 | 1/2011 | Moll et al. |
| 7,960,935 B2 | 6/2011 | Farritor et al. |
| 8,021,358 B2 | 9/2011 | Doyle et al. |
| 8,179,073 B2 | 5/2012 | Farritor et al. |
| 8,353,897 B2 | 1/2013 | Doyle et al. |
| 8,604,742 B2 | 12/2013 | Farritor et al. |
| 9,089,353 B2 | 7/2015 | Farritor |
| 2001/0018591 A1 | 8/2001 | Brock et al. |
| 2001/0049497 A1 | 12/2001 | Kalloo et al. |
| 2002/0003173 A1 | 1/2002 | Bauer et al. |
| 2002/0013601 A1 | 1/2002 | Nobles et al. |
| 2002/0026186 A1 | 2/2002 | Woloszka et al. |
| 2002/0038077 A1 | 3/2002 | de la Torre et al. |
| 2002/0065507 A1 | 5/2002 | Azizi |
| 2002/0091374 A1 | 7/2002 | Cooper |
| 2002/0103417 A1 | 8/2002 | Gazdzinski |
| 2002/0111535 A1 | 8/2002 | Kim et al. |
| 2002/0120254 A1 | 8/2002 | Julien et al. |
| 2002/0128552 A1 | 9/2002 | Nowlin et al. |
| 2002/0140392 A1 | 10/2002 | Borenstein et al. |
| 2002/0147487 A1 | 10/2002 | Sundquist et al. |
| 2002/0151906 A1 | 10/2002 | Demarais et al. |
| 2002/0156347 A1 | 10/2002 | Kim et al. |
| 2002/0171385 A1 | 11/2002 | Kim et al. |
| 2002/0173700 A1 | 11/2002 | Kim et al. |
| 2002/0190682 A1 | 12/2002 | Schempf et al. |
| 2003/0020810 A1 | 1/2003 | Takizawa et al. |
| 2003/0045888 A1 | 3/2003 | Brock et al. |
| 2003/0065250 A1 | 4/2003 | Chiel et al. |
| 2003/0089267 A1 | 5/2003 | Ghorbel et al. |
| 2003/0092964 A1 | 5/2003 | Kim et al. |
| 2003/0097129 A1 | 5/2003 | Davison et al. |
| 2003/0100817 A1 | 5/2003 | Wang et al. |
| 2003/0114731 A1 | 6/2003 | Cadeddu et al. |
| 2003/0135203 A1 | 7/2003 | Wang et al. |
| 2003/0139742 A1 | 7/2003 | Wampler et al. |
| 2003/0144656 A1 | 7/2003 | Ocel et al. |
| 2003/0167000 A1 | 9/2003 | Mullick |
| 2003/0172871 A1 | 9/2003 | Scherer |
| 2003/0179308 A1 | 9/2003 | Zamorano et al. |
| 2003/0181788 A1 | 9/2003 | Yokoi et al. |
| 2003/0229268 A1 | 12/2003 | Uchiyama et al. |
| 2003/0230372 A1 | 12/2003 | Schmidt |
| 2004/0117032 A1 | 1/2004 | Roth et al. |
| 2004/0024311 A1 | 2/2004 | Quaid |
| 2004/0034282 A1 | 2/2004 | Quaid |
| 2004/0034283 A1 | 2/2004 | Quaid |
| 2004/0034302 A1 | 2/2004 | Abovitz et al. |
| 2004/0050394 A1 | 3/2004 | Jin |
| 2004/0070822 A1 | 4/2004 | Shioda et al. |
| 2004/0099175 A1 | 5/2004 | Perrot et al. |
| 2004/0102772 A1 | 5/2004 | Baxter et al. |
| 2004/0106916 A1 | 6/2004 | Quaid et al. |
| 2004/0111113 A1 | 6/2004 | Nakamura et al. |
| 2004/0138525 A1 | 7/2004 | Saadat |
| 2004/0138552 A1 | 7/2004 | Harel et al. |
| 2004/0140786 A1 | 7/2004 | Borenstein |
| 2004/0153057 A1 | 8/2004 | Davison |
| 2004/0173116 A1 | 9/2004 | Ghorbel et al. |
| 2004/0176664 A1 | 9/2004 | Iddan |
| 2004/0215331 A1 | 10/2004 | Chew et al. |
| 2004/0225229 A1 | 11/2004 | Viola |
| 2004/0254680 A1 | 12/2004 | Sunaoshi |
| 2004/0267326 A1 | 12/2004 | Ocel et al. |
| 2005/0014994 A1 | 1/2005 | Fowler et al. |
| 2005/0021069 A1 | 1/2005 | Feuer et al. |
| 2005/0029978 A1 | 2/2005 | Oleynikov et al. |
| 2005/0043583 A1 | 2/2005 | Killmann et al. |
| 2005/0049462 A1 | 3/2005 | Kanazawa |
| 2005/0054901 A1 | 3/2005 | Yoshino |
| 2005/0054902 A1 | 3/2005 | Konno |
| 2005/0064378 A1 | 3/2005 | Toly |
| 2005/0065400 A1 | 3/2005 | Banik et al. |
| 2005/0083460 A1 | 4/2005 | Hattori et al. |
| 2005/0095650 A1 | 5/2005 | Khalili et al. |
| 2005/0096502 A1 | 5/2005 | Khalili |
| 2005/0143644 A1 | 6/2005 | Gilad et al. |
| 2005/0154376 A1 | 7/2005 | Riviere et al. |
| 2005/0165449 A1 | 7/2005 | Cadeddu et al. |
| 2005/0283137 A1 | 12/2005 | Doyle et al. |
| 2005/0288555 A1 | 12/2005 | Binmoeller |
| 2005/0288665 A1 | 12/2005 | Woloszko |
| 2006/0020272 A1 | 1/2006 | Gildenberg |
| 2006/0046226 A1 | 3/2006 | Bergler et al. |
| 2006/0119304 A1 | 6/2006 | Farritor et al. |
| 2006/0149135 A1 | 7/2006 | Paz |
| 2006/0152591 A1 | 7/2006 | Lin |
| 2006/0155263 A1 | 7/2006 | Lipow |
| 2006/0195015 A1 | 8/2006 | Mullick et al. |
| 2006/0196301 A1 | 9/2006 | Oleynikov et al. |
| 2006/0198619 A1 | 9/2006 | Oleynikov et al. |
| 2006/0241570 A1 | 10/2006 | Wilk |
| 2006/0241732 A1 | 10/2006 | Denker et al. |
| 2006/0253109 A1 | 11/2006 | Chu |
| 2006/0258954 A1 | 11/2006 | Timberlake |
| 2007/0032701 A1 | 2/2007 | Fowler et al. |
| 2007/0043397 A1 | 2/2007 | Ocel et al. |
| 2007/0055342 A1 | 3/2007 | Wu et al. |
| 2007/0080658 A1 | 4/2007 | Farritor et al. |
| 2007/0106113 A1 | 5/2007 | Ravo |
| 2007/0123748 A1 | 5/2007 | Meglan |
| 2007/0142725 A1 | 6/2007 | Hardin et al. |
| 2007/0156019 A1 | 7/2007 | Larkin et al. |
| 2007/0156211 A1 | 7/2007 | Ferren et al. |
| 2007/0167955 A1 | 7/2007 | De La Menardiere et al. |
| 2007/0225633 A1 | 9/2007 | Ferren et al. |
| 2007/0225634 A1 | 9/2007 | Ferren et al. |
| 2007/0241714 A1 | 10/2007 | Oleynikov et al. |
| 2007/0244520 A1 | 10/2007 | Ferren et al. |
| 2007/0250064 A1 | 10/2007 | Darois et al. |
| 2007/0255273 A1 | 11/2007 | Fernandez et al. |
| 2008/0004634 A1* | 1/2008 | Farritor .............. A61B 1/00158 606/130 |
| 2008/0015565 A1 | 1/2008 | Davison |
| 2008/0015566 A1 | 1/2008 | Livneh |
| 2008/0033569 A1 | 2/2008 | Ferren et al. |
| 2008/0045803 A1 | 2/2008 | Williams |
| 2008/0058835 A1 | 3/2008 | Farritor et al. |
| 2008/0058989 A1 | 3/2008 | Oleynikov et al. |
| 2008/0103440 A1 | 5/2008 | Ferren et al. |
| 2008/0109014 A1 | 5/2008 | Pena |
| 2008/0111513 A1 | 5/2008 | Farritor et al. |
| 2008/0119870 A1 | 5/2008 | Williams et al. |
| 2008/0132890 A1 | 6/2008 | Woloszko et al. |
| 2008/0161804 A1 | 7/2008 | Rioux et al. |
| 2008/0164079 A1 | 7/2008 | Ferren et al. |
| 2008/0183033 A1 | 7/2008 | Bern et al. |
| 2008/0221591 A1 | 9/2008 | Farritor et al. |
| 2008/0269557 A1 | 10/2008 | Marescaux et al. |
| 2008/0269562 A1 | 10/2008 | Marescaux et al. |
| 2009/0020724 A1 | 1/2009 | Paffrath |
| 2009/0024142 A1 | 1/2009 | Ruiz Morales |
| 2009/0048612 A1 | 2/2009 | Farritor et al. |
| 2009/0054909 A1 | 2/2009 | Farritor et al. |
| 2009/0069821 A1 | 3/2009 | Farritor et al. |
| 2009/0076536 A1 | 3/2009 | Rentschler et al. |
| 2009/0137952 A1 | 5/2009 | Ramamurthy et al. |
| 2009/0143787 A9 | 6/2009 | De La Pena |
| 2009/0163929 A1 | 6/2009 | Yeung et al. |
| 2009/0171373 A1 | 7/2009 | Farritor et al. |
| 2009/0234369 A1 | 9/2009 | Bax et al. |
| 2009/0236400 A1 | 9/2009 | Cole et al. |

(56) References Cited

U.S. PATENT DOCUMENTS

| | | |
|---|---|---|
| 2009/0240246 A1 | 9/2009 | Devill et al. |
| 2009/0247821 A1 | 10/2009 | Rogers |
| 2009/0248038 A1 | 10/2009 | Blumenkranz et al. |
| 2009/0281377 A1 | 11/2009 | Newell et al. |
| 2009/0305210 A1 | 12/2009 | Guru et al. |
| 2010/0010294 A1 | 1/2010 | Conlon et al. |
| 2010/0016659 A1 | 1/2010 | Weitzner et al. |
| 2010/0016853 A1 | 1/2010 | Burbank |
| 2010/0042097 A1 | 2/2010 | Newton et al. |
| 2010/0056863 A1 | 3/2010 | Dejima et al. |
| 2010/0069710 A1 | 3/2010 | Yamatani et al. |
| 2010/0069940 A1 | 3/2010 | Miller et al. |
| 2010/0081875 A1 | 4/2010 | Fowler et al. |
| 2010/0139436 A1 | 6/2010 | Kawashima et al. |
| 2010/0198231 A1 | 8/2010 | Manzo et al. |
| 2010/0204713 A1 | 8/2010 | Ruiz |
| 2010/0245549 A1 | 9/2010 | Allen et al. |
| 2010/0262162 A1 | 10/2010 | Omori |
| 2010/0292691 A1 | 11/2010 | Brogna |
| 2010/0318059 A1 | 12/2010 | Farritor et al. |
| 2011/0015569 A1 | 1/2011 | Kirschenman et al. |
| 2011/0020779 A1 | 1/2011 | Hannaford et al. |
| 2011/0071347 A1 | 3/2011 | Rogers et al. |
| 2011/0071544 A1 | 3/2011 | Steger et al. |
| 2011/0077478 A1 | 3/2011 | Freeman et al. |
| 2011/0082365 A1 | 4/2011 | McGrogan et al. |
| 2011/0098529 A1 | 4/2011 | Ostrovsky et al. |
| 2011/0152615 A1 | 6/2011 | Schostek et al. |
| 2011/0224605 A1 | 9/2011 | Farritor et al. |
| 2011/0230894 A1 | 9/2011 | Simaan et al. |
| 2011/0237890 A1 | 9/2011 | Farritor et al. |
| 2011/0238080 A1 | 9/2011 | Ranjit et al. |
| 2011/0264078 A1* | 10/2011 | Lipow .................. A61B 19/201 606/1 |
| 2011/0270443 A1 | 11/2011 | Kamiya et al. |
| 2012/0035582 A1 | 2/2012 | Nelson et al. |
| 2012/0109150 A1 | 5/2012 | Quaid et al. |
| 2012/0116362 A1* | 5/2012 | Kieturakis ............. A61B 17/29 606/1 |
| 2012/0179168 A1 | 7/2012 | Farritor |
| 2012/0253515 A1 | 10/2012 | Coste-Maniere et al. |
| 2013/0041360 A1 | 2/2013 | Farritor |
| 2013/0131695 A1 | 5/2013 | Scarfogliero et al. |
| 2013/0345717 A1 | 5/2013 | Scarfogliero et al. |
| 2014/0039515 A1 | 2/2014 | Mondry et al. |
| 2014/0046340 A1 | 2/2014 | Wilson et al. |
| 2014/0058205 A1 | 2/2014 | Frederick et al. |
| 2014/0303434 A1 | 10/2014 | Farritor et al. |
| 2015/0051446 A1 | 2/2015 | Farritor et al. |

FOREIGN PATENT DOCUMENTS

| | | |
|---|---|---|
| EP | 1354670 | 10/2003 |
| EP | 2286756 | 2/2011 |
| EP | 2286756 A1 | 2/2011 |
| EP | 2329787 | 8/2011 |
| EP | 2563261 | 3/2013 |
| JP | 2004144533 | 5/1990 |
| JP | 5115425 | 5/1993 |
| JP | 200716235 | 6/1993 |
| JP | 2006507809 | 9/1994 |
| JP | 07 136173 | 5/1995 |
| JP | 7306155 | 11/1995 |
| JP | 08-224248 | 9/1996 |
| JP | 2001505810 | 5/2001 |
| JP | 2003220065 | 8/2003 |
| JP | 2004322310 | 6/2004 |
| JP | 2004180781 | 7/2004 |
| JP | 2004329292 | 11/2004 |
| JP | 2006508049 | 3/2006 |
| JP | 2010536436 | 8/2007 |
| JP | 2009-106606 | 5/2009 |
| JP | 2010-533045 | 10/2010 |
| JP | 2010-536436 | 12/2010 |
| JP | 2011-504794 | 2/2011 |
| JP | 2011-045500 | 3/2011 |
| JP | 2011-115591 | 6/2011 |
| WO | WO 1992/21291 | 5/1991 |
| WO | WO 0189405 | 11/2001 |
| WO | WO 2002/082979 | 10/2002 |
| WO | WO 2002/100256 | 12/2002 |
| WO | WO 2005/009211 | 7/2004 |
| WO | WO 2005009211 | 2/2005 |
| WO | WO 2005044095 | 5/2005 |
| WO | WO 2006/052927 | 8/2005 |
| WO | WO 2006 005075 | 1/2006 |
| WO | WO 2006/079108 | 1/2006 |
| WO | WO2006079108 | 7/2006 |
| WO | WO 2007011654 | 1/2007 |
| WO | WO 2007/111571 | 10/2007 |
| WO | WO 2007/149559 | 12/2007 |
| WO | WO 2009023851 A1 | 8/2008 |
| WO | WO 2009/144729 | 12/2009 |
| WO | WO2010/042611 | 4/2010 |
| WO | WO2010/046823 | 4/2010 |
| WO | WO201050771 A2 | 5/2010 |
| WO | WO 2011/118646 A1 | 9/2011 |
| WO | WO 2011/135503 A1 | 11/2011 |
| WO | WO 2011135503 | 11/2011 |
| WO | WO 2011135503 A1 * | 11/2011 ............. A61B 34/30 |
| WO | WO 2011075693 | 7/2012 |
| WO | WO 2013009887 | 1/2013 |
| WO | WO 2014011238 | 1/2014 |

OTHER PUBLICATIONS

International Preliminary Report on Patentability from related case PCT/US2007/014567, dated Jan. 8, 2009, 11 pp.

International Search report and Written Opinion from international application No. PCT/US2012/41911, dated Mar. 13, 2013.

International Search Report and Written Opinion from international application No. PCT/US12/46274, dated Sep. 25, 2012.

International Search Report and Written Opinion from international application No. PCT/US2007/089191, dated Nov. 10, 2008, 20 pp.

"International Search Report and Written Opinion from international application No. PCT/US07/14567, dated Apr. 28, 2008, 19 pp."

International Search Report and Written Opinion of international application No. PCT/US2008/069822, dated Aug. 5, 2009, 12 pp.

International Search Report and Written Opinion of international application No. PCT/US2008/073334, dated Jan. 12, 2009, 11 pp.

International Search Report and Written Opinion of international application No. PCT/US2008/073369, dated Nov. 12, 2008, 12 pp.

International Search Report and Written Opinion issued in PCT/US11/46809, dated Dec. 8, 2011.

Ishiyama et al., "Spiral-type Micro-machine for Medical Applications," 2000 International Symposium on Micromechatronics and Human Science, 2000: 65-69.

Jagannath et al., "Peroral transgastric endoscopic ligation of fallopian tubes with long-term survival in a porcine model," Gastrointestinal Endoscopy, 2005; 61(3): 449-453.

Kalloo et al., "Flexible transgastric peritoneoscopy: a novel approach to diagnostic and therapeutic interventions in the peritoneal cavity," Gastrointestinal Endoscopy, 2004; 60(1): 114-117.

Kang et al., "Robotic Assistants Aid Surgeons During Minimally Invasive Procedures," IEEE Engineering in Medicine and Biology, Jan.-Feb. 2001; pp. 94-104.

Kantsevoy et al., "Endoscopic gastrojejunostomy with survival in a porcine model," Gastrointestinal Endoscopy, 2005; 62(2): 287-292.

Kantsevoy et al., "Transgastric endoscopic splenectomy," Surgical Endoscopy, 2006; 20: 522-525.

Kazemier et al. (1998), "Vascular Injuries During Laparoscopy," J. Am. Coli. Surg. 186(5): 604-5.

Kim, "Early Experience with Telemanipulative Robot-Assisted Laparoscopic Cholecystectomy Using da Vinci," Surgical Laparoscopy, Endoscopy & Percutaneous Techniques, 2002; 12(1):33-40.

Ko et al., "Per-Oral transgastric abdominal surgery," Chinese Journal of Digestive Diseases, 2006; 7: 67-70.

(56) References Cited

OTHER PUBLICATIONS

Lafullarde et al., "Laparoscopic Nissen Fundoplication: Five-year Results and Beyond," Arch/Surg, Feb. 2001; 136:180-184.
Leggett et al. (2002), "Aortic injury during laparoscopic fundoplication," Surg. Endoscopy 16(2): 362.
Li et al. (2000), "Microvascular Anastomoses Performed in Rats Using a Microsurgical Telemanipulator," Comp. Aid. Surg. 5: 326-332.
Liem et al., "Comparison of Conventional Anterior Surgery and Laparoscopic Surgery for Inguinal-hernia Repair," New England Journal of Medicine, 1997; 336 (22): 1541-1547.
MacFarlane et al., "Force-Feedback Grasper Helps Restore the Sense of Touch in Minimally Invasive Surgery," Journal of Gastrointestinal Surgery, 1999; 3: 278-285.
Mack et al., "Present Role of Thoracoscopy in the Diagnosis and Treatment of Diseases of the Chest," Ann Thorac Surgery, 1992; 54: 403-409.
Mack, "Minimally Invasive and Robotic Surgery," JAMA, Feb. 2001; 285(5): 568-572.
Mei et al., "Wireless Drive and Control of a Swimming Microrobot," Proceedings of the 2002 IEEE International Conference on Robotics & Automation, May 2002: 1131-1136.
Melvin et al., "Computer-Enhanced vs. Standard Laparoscopic Antireflux Surgery," J Gastrointest Surg 2002; 6: 11-16.
Menciassi et al., "Locomotion of a Leffed Capsule in the Gastrointestinal Tract: Theoretical Study and Preliminary Technological Results," IEEE Int. Conf. on Engineering in Medicine and Biology, San Francisco, CA, pp. 2767-2770, Sep. 2004.
Menciassi et al., "Robotic Solutions and Mechanisms for a Semi-Autonomous Endoscope," Proceedings of the 2002 IEEE/RSJ Intl. Conference on Intelligent Robots and Systems, Oct. 2002; 1379-1384.
Menciassi et al., "Shape memory alloy clamping devices of a capsule for monitoring tasks in the gastrointestinal tract," J. Micromech. Microeng, 2005, 15: 2045-2055.
Meron, "The development of the swallowable video capsule (M2A)," Gastrointestinal Endoscopy 2000; 52 6: 817-819.
Micron, http://www.micron.com, 2006, ¼-inch VGA NTSC/PAL CMOS Digital Image Sensor, 98 pp.
Midday Jeff et al., "Material Handling System for Robotic natural Orifice Surgery", Proceedings of the 2011 Design of medical Devices Conference, Apr. 12-14, 2011, Minneapolis, MN, 4 pages.
Miller, Ph.D., et al., "In-Vivo Stereoscopic Imaging System with 5 Degrees-of-Freedom for Minimal Access Surgery," Dept. of Computer Science and Dept. Of Surgery, Columbia University, New York, NY, 7 pp.
Munro (2002), "Laparoscopic access: complications, technologies, and techniques," Curro Opin. Obstet. Gynecol., 14(4): 365-74.
Nio et al., "Efficiency of manual vs robotical (Zeus) assisted laparoscopic surgery in the performance of standardized tasks," Surg Endosc, 2002; 16: 412-415.
Office Action dated Apr. 17, 2007, received in related case U.S. Appl. No. 11/552,379, 5 pp.
Office Action dated Apr. 3, 2009, received in related case U.S. Appl. No. 11/932,516, 43 pp.
Office Action dated Aug. 18, 2006, received in related case U.S. Appl. No. 11/398,174, 6 pp.
Office Action dated Aug. 21, 2006, received in related case U.S. Appl. No. 11/403,756, 6 pp.
Office Action dated Oct. 29, 2007, received in related case U.S. Appl. No. 11/695,944, 6 pp.
Office Action dated Oct. 9, 2008, received in related case U.S. Appl. No. 11/932,441, 4 pp.
Oleynikov et al., "In Vivo Camera Robots Provide Improved Vision for Laparoscopic Surgery," Computer Assisted Radiology and Surgery (CARS), Chicago, IL, Jun. 23-26, 2004b.
Oleynikov et al., "In Vivo Robotic Laparoscopy," Surgical Innovation, Jun. 2005, 12(2): 177-181.
Oleynikov et al., "Miniature Robots Can Assist in Laparoscopic Cholecystectomy," Journal of Surgical Endoscopy, 19-4: 473-476, 2005.
O'Neill, "Surgeon takes new route to gallbladder," The Oregonian, Jun. 2007, 2 pp.
Orlando et al., (2003), "Needle and Trocar Injuries in Diagnostic Laparoscopy under Local Anesthesia: What Is the True Incidence of These Complications?" Journal of Laparoendoscopic & Advanced Surgical Techniques 13(3): 181-184.
Park et al., "Trocar-less Instrumentation for Laparoscopy: Magnetic Positioning of Intra-abdominal Camera and Retractor," Ann Surg, Mar. 2007; 245(3): 379-384.
Park et al., "Experimental studies of transgastric gallbladder surgery: cholecystectomy and cholecystogastric anastomosis (videos)," Gastrointestinal Endoscopy, 2005; 61(4): 601-606.
Abbott et al., "Design of an Endoluminal NOTES Robotic System," from the Proceedings of the 2007 IEEE/RSJ Int'l Conf. on Intelligent Robot Systems, San Diego, CA, Oct. 29-Nov. 2, 2007, pp. 410-416.
Allendorf et al., "Postoperative Immune Function Varies Inversely with the Degree of Surgical Trauma in a Murine Model," Surgical Endoscopy 1997; 11:427-430.
Ang, "Active Tremor Compensation in Handheld Instrument for Microsurgery," Doctoral Dissertation, tech report CMU-RI-TR-04-28, Robotics Institute, Carnegie Mellon Unviersity, May 2004, 167pp.
Applicant Amendment after Notice of Allowance under Rule 312, filed Aug. 25, 2008, in related case U.S. Appl. No. 11/695,944, 6pp.
Applicant Response to Office Action dated Apr. 17, 2007, in related case U.S. Appl. No. 11/552,379, filed Aug. 8, 2007, 7 pp.
Applicant Response to Office Action dated Aug. 18, 2006, in related case U.S. Appl. No. 11/398,174, filed Nov. 7, 2006, 8pp.
Applicant Response to Office Action dated Aug. 21, 2006, in related case U.S. Appl. No. 11/403,756, filed Nov. 21, 2006, 52pp.
Applicant Response to Office Action dated Oct. 29, 2007, in related case U.S. Appl. No. 11/695,944, filed Jan. 22, 2008, 6pp.
Atmel 8005X2 Core, http://www.atmel.com, 2006, 186pp.
Bailey et al., "Complications of Laparoscopic Surgery," Quality Medical Publishers, Inc., 1995, 25pp.
Ballantyne, "Robotic Surgery, Telerobotic Surgery, Telepresence, and Telementoring," Surgical Endoscopy, 2002; 16: 1389-1402.
Bauer et al., "Case Report: Remote Percutaneous Renal Percutaneous Renal Access Using a New Automated Telesurgical Robotic System," Telemedicine Journal and e-Health 2001; (4): 341-347.
Begos et al., "Laparoscopic Cholecystectomy: From Gimmick to Gold Standard," J Clin Gastroenterol, 1994; 19(4): 325-330.
Berg et al., "Surgery with Cooperative Robots," Medicine Meets Virtual Reality, Feb. 2007, 1 pg.
Breda et al., "Future developments and perspectives in laparoscopy," Eur. Urology 2001; 40(1): 84-91.
Breedveld et al., "Design of Steerable Endoscopes to Improve the Visual Perception of Depth During Laparoscopic Surgery," ASME, Jan. 2004; vol. 126, pp. 1-5.
Breedveld et al., "Locomotion through the Intestine by means of Rolling Stents," Proceedings of the ASME Design Engineering Technical Conferences, 2004, pp. 1-7.
Calafiore et al., Multiple Arterial Conduits Without Cardiopulmonary Bypass: Early Angiographic Results,: Ann Thorac Surg, 1999; 67: 450-456.
Camarillo et al., "Robotic Technology in Surgery: Past, Present and Future," The American Journal of Surgery, 2004; 188: 2S-15.
Cavusoglu et al., "Telesurgery and Surgical Simulation: Haptic Interfaces to Real and Virtual Surgical Environments," In McLaughliin, M.L., Hespanha, J.P., and Sukhatme, G., editors. Touch in virtual environments, IMSC Series in Multimedia 2001, 28pp.
Cavusoglu et al., "Robotics for Telesurgery: Second Generation Berkeley/UCSF Laparoscopic Telesurgical Workstation and Looking Towards the Future Applications," Industrial Robot: An International Journal, 2003; 30(1): 22-29.
Chanthasopeephan et al., (2003), "Measuring Forces in Liver Cutting: New Equipment and Experimenal Results," Annals of Biomedical Engineering 31: 1372-1382.

(56) References Cited

OTHER PUBLICATIONS

Choi et al., "Flexure-based Manipulator for Active Handheld Microsurgical Instrument," Proceedings of the 27th Annual International Conference of the IEEE Engineering in Medicine and Biology Society (EMBS), Sep. 2005, 4pp.
Cuschieri, "Technology for Minimal Access Surgery," BMJ, 1999, 319: 1-6.
Dakin et al., "Comparison of laparoscopic skills performance between standard instruments and two surgical robotic systems," Surg Endosc., 2003; 17: 574-579.
Dumpert et al., "Improving in Vivo Robot Visioin Quality," from the Proceedings of Medicine Meets Virtual Realtiy, Long Beach, CA, Jan. 26-29, 2005. 1 pg.
Dumpert et al., "Stereoscopic In Vivo Surgical Robots," IEEE Sensors Special Issue on In Vivo Sensors for Medicine, Jan. 2007, 10 pp.
Examiner Interview Summary dated Aug. 6 and Aug. 12, 2008, in related case U.S. Appl. No. 11/695,944, 1 pg.
Examiner Interview Summary dated May 9, 2008, in related case U.S. Appl. No. 11/695,944, 1 pg.
Examiner Interview Summary dated Nov. 30, 2006, in related case U.S. Appl. No. 11/398,174, 2pp.
Falcone et al., "Robotic Surgery," Clin. Obstet. Gynecol. 2003, 46(1): 37-43.
Faraz et al., "Engineering Approaches to Mechanical and Robotic Design for Minimaly Invasive Surgery (MIS)," Kluwer Academic Publishers (Boston), 2000, 13pp.
Fearing et al., "Wing Transmission for a Micromechanical Flying Insect," Proceedings of the 2000 IEEE International Conference to Robotics & Automation, Apr. 2000; 1509-1516.
Fireman et al., "Diagnosing small bowel Crohn's desease with wireless capsule endoscopy," Gut 2003; 52: 390-392.
Flynn et al., "Tomorrow's Surgery: micromotors and microbots for minimally invasive procedures," Minimally Invasive Surgery & Allied Technologies.
Franklin et al., "Prospective Comparison of Open vs. Laparoscopic Colon Surgery for Carcinoma: Five-Year Results," Dis Colon Rectum, 1996; 39: S35-S46.
Franzino, "The Laprotek Surgical System and the Next Generation of Robotics," Surg Clin North Am, 2003 83(6): 1317-1320.
Fraulob et al., "Miniature assistance module for robot-assisted heart surgery," Biomed. Tech. 2002, 47 Suppl. 1, Pt. 1:12-15.
Fukuda et al., "Mechanism and Swimming Experiment of Micro Mobile Robot in Water," Proceedings of the 1994 IEEE International Conference on Robotics and Automation, 1994: 814-819.
Fukuda et al., "Micro Active Catheter System with Multi Degrees of Freedom," Proceedings of the IEEE International Conference on Robotics and Automation, May 1994, pp. 2290-2295.
Fuller et al., "Laparoscopic Trocar Injuries: A Report from a U.S. Food and Drug Administration (FDA) Center for Devices and Radiological Health (CDRH) Systematic Technology Assessment of Medical Products (STAMP) Committe," U.S. Food and Drug Adminstration, available at http://www.fdaJ:?;ov, Finalized: Nov. 7, 2003; Updated: Jun. 24, 2005, 11 pp.
Grady, "Doctors Try New Surgery for Gallbladder Removal," The New York Times, Apr. 20, 2007, 3 pp.
Guber et al., "Miniaturized Instrument Systems for Minimally Invasive Diagnosis and Therapy," Biomedizinishe Technic. 2002, Band 47, Erganmngsband 1: 198-201.
Tendick et al., "Applications of Micromechatronics in Minimally Invasive Surgery," IEEE/ASME Transactions on Mechatronics, 1998; 3(1): 34-42.
Thomann et al., "The Design of a new type of Micro Robot for the Intestinal Inspection," Proceedings of the 2002 IEEE Intl. Conference on Intelligent Robots and Systems, Oct. 2002: 1385-1390.
U.S. Appl. No. 60/180,960, filed Feb. 2000.
U.S. Appl. No. 60/956,032, filed Aug. 15, 2007.
U.S. Appl. No. 60/983,445, filed Oct. 29, 2007.
U.S. Appl. No. 60/990,062, filed Nov. 26, 2007.
U.S. Appl. No. 60/990,076, filed Nov. 26, 2007.
U.S. Appl. No. 60/990,086, filed Nov. 26, 2007.
U.S. Appl. No. 60/990,106, filed Nov. 26, 2007.
U.S. Appl. No. 60/990,470, filed Nov. 27, 2007.
U.S. Appl. No. 61/025,346, filed Feb. 1, 2008.
U.S. Appl. No. 61/030,588, filed Feb. 22, 2008.
U.S. Appl. No. 61/030,617 filed Feb. 22, 2008.
Way et al., (editors), "Fundamentals of Laparoscopic Surgery," Churchill Livingstone Inc., 1995, 14 pp.
Wolfe et al., "Endoscopic Cholecystectomy: An analysis of Complications," Arch. Surg. Oct. 1991; 126: 1192-1196.
Worn et al., "Espirit Project No. 33915: Miniaturised Robot for Micro Manipulation (MINIMAN)", Nov. 1998; http://www.ipr.ira.ujka.de/-microbot/miniman.
Yu et al., "Microrobotic Cell Injection," Proceedings of the 2001 IEEE International Conference on Robotics and Automation, May 2001; 620-625.
Yu, BSN, RN, "M2ATM Capsule Endoscopy a Breakthrough Diagnostic Tool for Small Intestine Imagining," vol. 25, No. 1, Gastroenterology Nursing, pp. 24-27.
International Search Report and Written Opinion of international application No. PCT/US2010/061137, dated Feb. 11, 2011, 10 pp.
Abbou et al., "Laparoscopic Radical Prostatectomy with a Remote Controlled Robot," The Journal of Urology, Jun. 2001, 165: 1964-1966.
Glukhovsky et al.., "The development and application of wireless capsule endoscopy," Int. J. Med. Robot. Comput. Assist. Surgery, 2004; I (1): 114-123.
Gong et al., Wireless endoscopy, Gastrointestinal Endoscopy 2000; 51(6): 725-729.
Hanly et al., "Value of the SAGES Learning Center in introducing new technology," Surgical Endoscopy, 2004; 19 (4): 477-483.
Hanly et al., "Robotic Abdominal Surgery," The American Journal of Surgery 188 (Suppl.to Oct. 1994): 19S-26S,2004.
Palm, William, "Rapid Prototyping Primer" May 1998 (revised Jul. 30, 2002) (http://www.me.psu.edu/lamancusa/rapidpro/primer/chapter2.htm).
Patronik et al., "Development of a Tethered Epicardial Crawler for Minimally Invasive Cardiac Therapies," IEEE, pp. 239-240.
Patronik et al., "Crawling on the Heart: A Mobile Robotic Device for Minimally Invasive Cardiac Interventions," MICCAI, 2004, pp. 9-16.
Patronik et al., "Preliminary evaluation of a mobile robotic device for navigation and intervention on the beating heart," Computer Aided Surgery, 10(4): 225-232, Jul. 2005.
Peirs et al., "A miniature manipulator for integration in a self-propelling endoscope," Sensors and Actuators A, 2001, 92: 343-349.
Peters, "Minimally Invasive Colectomy: Are the Potential Benefits Realized?" Dis Colon Rectum 1993; 36: 751-756.
Phee et al, "Analysis and Development of Locomotion Devices for the Gastrointestinal Tract," IEEE Transaction on Biomedical Engineering, vol. 49, No.6, Jun. 2002, pp. 613-616.
Phee et al, "Development of Microrobotic Devices for Locomotion in the Human Gastrointestinal Tract," International Conference on Computational Intelligence, Robotics and Autonomous Systems (CIRAS 2001), Nov. 28-30, (2001), Singapore.
Platt et al., "In Vivo Robotic Cameras can Enhance Imaging Capability During Laparoscopic Surgery," in the Proceedings of the Society of American Gastrointestinal Endoscopic Surgeons (SAGES) Scientific Conference, Ft. Lauderdale, FL, Apr. 13-16, 2005, I pg.
Preliminary Amendment filed Apr. 11, 2007, in related case U.S. Appl. No. 11/403,756, 7 pp.
Preliminary Amendment filed July 30, 2008, in related case U.S. Appl. No. 12/171,413, 4 pp.
RCE and Amendment filed Jun. 13, 2007, in related case U.S. Appl. No. 11/403,756, 8 pp.
Rentschler et al., "Mobile In Vivo Biopsy and Camera Robot," Studies in Health and Infonnatics Medicine Meets Virtual Reality, vol. 119., pp. 449-454, IOS Press, Long Beach, CA, 2006e.
Rentschler et al., "Mobile In Vivo Biopsy Robot," IEEE International Conference on Robotics and Automation, Orlando, Florida, May 2006, pp. 4155-4160.

(56) References Cited

OTHER PUBLICATIONS

Rentschler et al., "Miniature in vivo Robots for Remote and Harsh Environments," IEEE Transactions on Information Technology in Biomedicine, Jan. 2006; 12(1): 66-75.
Rentschler et al., "An In Vivo Mobile Robot for Surgical Vision and Task Assistance," Journal of Medical Devices, Mar. 2007, vol. 1: 23-29.
Rentschler et al., "In vivo Mobile Surgical Robotic Task Assistance," 1 pg.
Rentschler et al., "In vivo Robotics during the NEEMO 9 Mission," Medicine Meets Virtual Reality, Feb. 2007, I pg.
Rentschler et al., "In Vivo Robots for Laparoscopic Surgery," Studies in Health Technology and Infonnatics—Medicine Meets Virtual Reality, ISO Press, Newport Beach, CA, 2004a, 98: 316-322.
Rentschler et al., "Mechanical Design of Robotic In Vivo Wheeled Mobility," ASME Journal of Mechanical Design, 2006a, pp. I-II.
Rentschler et al., "Mobile In Vivo Camera Robots Provide Sole Visual Feedback for Abdominal Exploration and Cholecystectomy," Journal of Surgical Endoscopy, 20-I: 135-138, 2006b.
Rentschler et al., "Mobile in Vivo Robots Can Assist in Abdominal Exploration," from the Proceedings of the Society of American Gastrointestinal Endoscopic Surgeons (SAGES) Scientific Conference, Ft. Lauderdale, FL, Apr. 13-16, 2005b.
Rentschler et al., "Modeling, Analysis, and Experimental Study of In Vivo Wheeled Robotic Mobility," IEEE Transactions on Robotics, 22 (2): 308-321, 2005c.
Rentschler et al., "Natural Orifice Surgery with an Endoluminal Mobile Robot," The Society of American Gastrointestinal Endoscopic Surgeons, Dallas, TX, Apr. 2006d, 14 pp.
Rentschler et al., "Theoretical and Experimental Analysis of In Vivo Wheeled Mobility," ASME Design Engineering Technical Conferences: 28th Biennial Mechanisms and Robotics Conference, Salt Lake City, Utah, Sep. 28-Oct. 2, 2004, pp. 1-9.
Rentschler et al., "Toward In Vivo Mobility," Studies in Health Technology and Informatics—Medicine Meets Virtual Reality, ISO Press, Long Beach, CA, 2005a, III: 397-403.
Response to Rule 312 Amendment in related case U.S. Appl. No. 11/695,944, dated Jan. 12, 2009, 2 pp.
Riviere et al., "Toward Active Tremor Canceling in Handheld Microsurgical Instruments," IEEE Transactions on Robotics and Automation, Oct. 2003, 19(5): 793-800.
Rosen et al., "Force Controlled and Teleoperated Endoscopic, Grasper for Minimally Invasive Surgery—Experimental Performance Evaluation," IEEE Transactions of Biomedical Engineering, Oct. 1999; 46(10): 1212-1221.
Rosen et al., "Objective Laparoscopic Skills Assessments of Surgical Residents Using Hidden Markov Models Based on Haptic Information and Tool/Tissue Interactions," Studies in Health Technology and Informatics—Medicine Meets Virtual Reality, Jan. 2001, 7 pp.
Rosen et al., "Spherical Mechanism Analysis of a Surgical Robot for Minimally Invasive Surgery—Analytical and Experimental Approaches," Studies in Health Technology and Informatics—Medicine Meets Virtual Reality, pp. 442-448, Jan. 2005.
Rosen et al., "Task Decomposition of Laparoscopic Surgery for Objective Evaluation of Surgical Residents' Learning Curve Using Hidden Markov Model," Computer Aided Surgery, vol. 7, pp. 49-61, 2002.
Rosen et al., "The Blue DRAGON—A System of Measuring the Kinematics and the Dynamics of Minimally Invasive Surgical Tools In-Vivo," Proc. of the 2002 IEEE International Conference on Robotics and Automation, Washington, DC, pp. 1876-1881, May 2002.
Ruurda et al., "Robot-Assisted surgical systems: a new era in laparoscopic surgery," Ann R. Coll Surg Engl., 2002; 84: 223-226.
Ruurda et al., "Feasibility of Robot-Assisted Laparoscopic Surgery," Surgical Laparoscopy, Endoscopy & Percutaneous Techniques, 2002; 12(1):41-45.
Sackier et al., "Robotically assisted laparoscopic surgery," Surgical Endoscopy, 1994; 8: 63-66.
Salky, "What is the Penetration of Endoscopic Techniques into Surgical Practice?" Digestive Surgery, 2000; 17:422-426.
Satava, "Surgical Robotics: The Early Chronicles," Surgical Laparoscopy, Endoscopy & Percutaneous Techniques, 2002; 12(1): 6-16.
Schippers et al., (1996) "Requirements and Possibilities of Computer-Assisted Endoscopic Surgery," In: Computer Integrated Surgery: Technology and Clinical Applications, pp. 561-565.
Schurr et al., "Robotics and Telemanipulation Technologies for Endoscopic Surgery," Surgical Endoscopy, 2000; 14: 375-381.
Schwartz, "In the Lab: Robots that Slink and Squirm," The New York Times, Mar. 27, 2007, 4 pp.
Sharp LL-151-3D, http://www.sharp3d.com, 2006, 2 pp.
Slatkin et al., "The Development of a Robotic Endoscope," Proceedings of the 1995 IEEE International Conference on Robotics and Automation, pp. 162-171, 1995.
Smart Pill "Fantastic Voyage: Smart Pill to Expand Testing," http://www.smartpilldiagnostics.com, Apr. 13, 2005, 1 pg.
Southern Surgeons Club (1991), "A prospective analysis of 1518 laparoscopic cholecystectomies," N. Eng. 1 Med. 324 (16): 1073-1078.
Stefanini et al., "Modeling and Experiments on a Legged Microrobot Locomoting in a Tubular Compliant and Slippery Environment," Int. Journal of Robotics Research, vol. 25, No. 5-6, pp. 551-560, May-Jun. 2006.
Stiff et al.., "Long-term Pain: Less Common After Laparoscopic than Open Cholecystectomy," British Journal of Surgery, 1994; 81: 1368-1370.
Strong, et al., "Efficacy of Novel Robotic Camera vs. a Standard Laproscopic Camera," Surgical Innovation vol. 12, No. 4, Dec. 2005, Westminster Publications, Inc., pp. 315-318.
Suzumori et al., "Development of Flexible Microactuator and its Applications to Robotics Mechanisms," Proceedings of the IEEE International Conference on Robotics and Automation, 1991: 1622-1627.
Taylor et al., "A Telerobotic Assistant for Laparoscopic Surgery," IEEE Eng Med Biol, 1995; 279-287.
Tendick et al.. (1993), "Sensing and Manipulation Problems in Endoscopic Surgery: Experiment, Analysis, and Observation," Presence 2( 1): 66-81.
Stoianovici et al., "Robotic Tools for Minimally Invasive Urologic Surgery", Jan. 1, 2002, pp. 1-17.
Cleary et al., "State of the Art in Surgical Rootics: Clinical Applications and Technology Challenges", "Computer Aided Surgery", Jan. 1, 2002, pp. 312-328, vol. 6.
Green, "Telepresence Surgery", Jan. 1, 1995, Publisher: IEEE Engineering in Medicine and Biology.

* cited by examiner

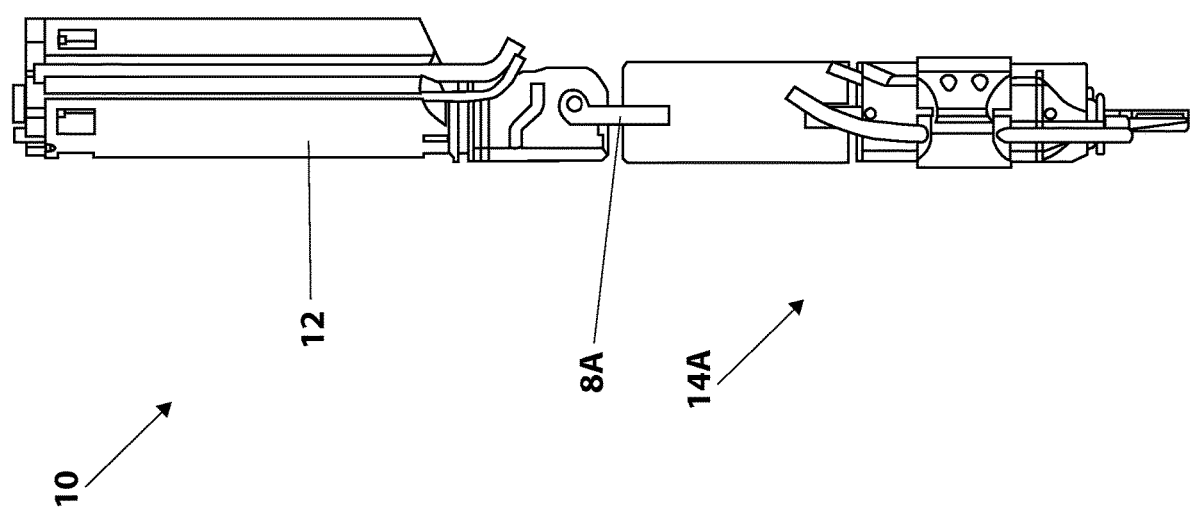

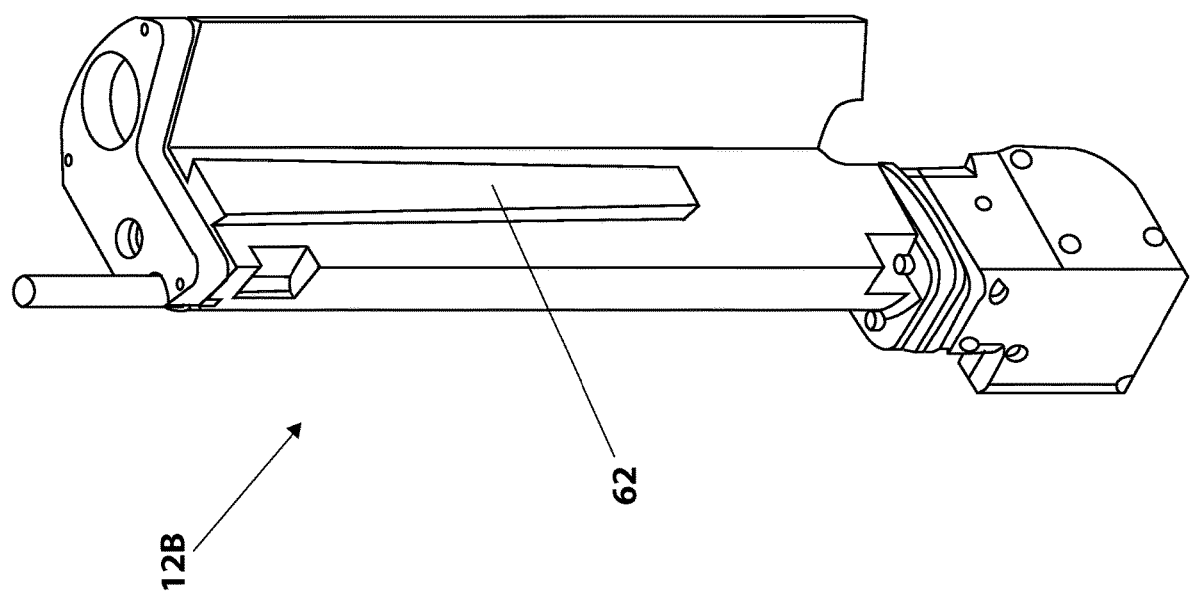

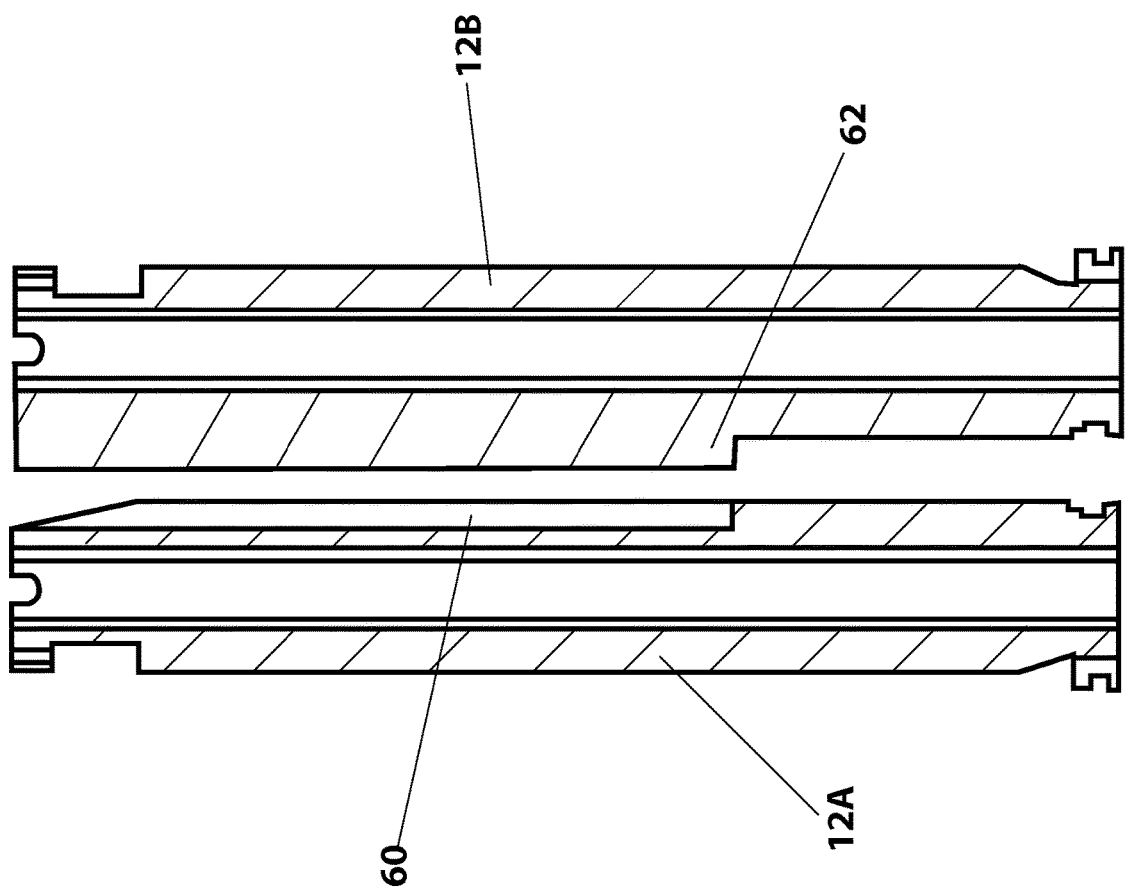

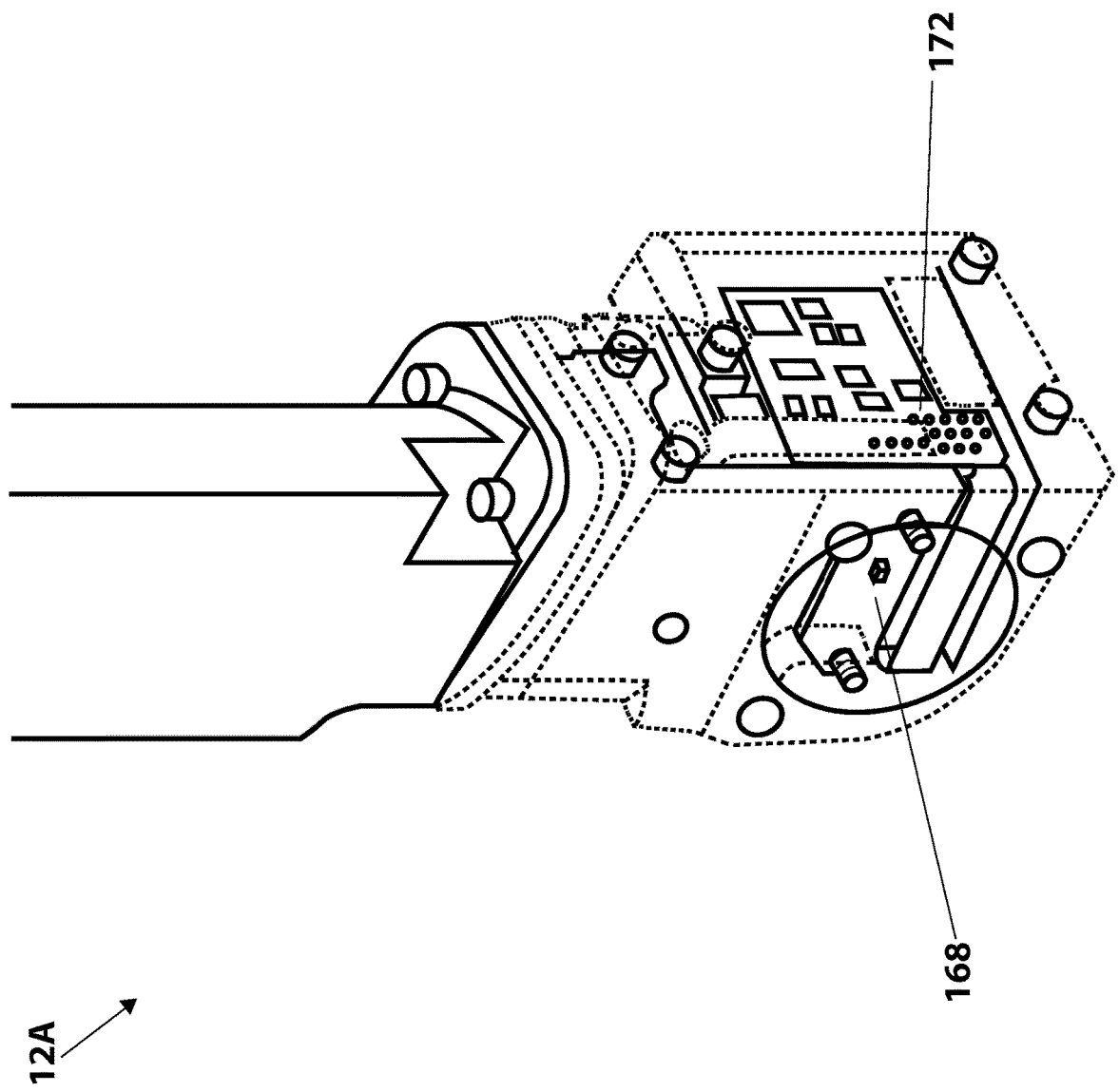

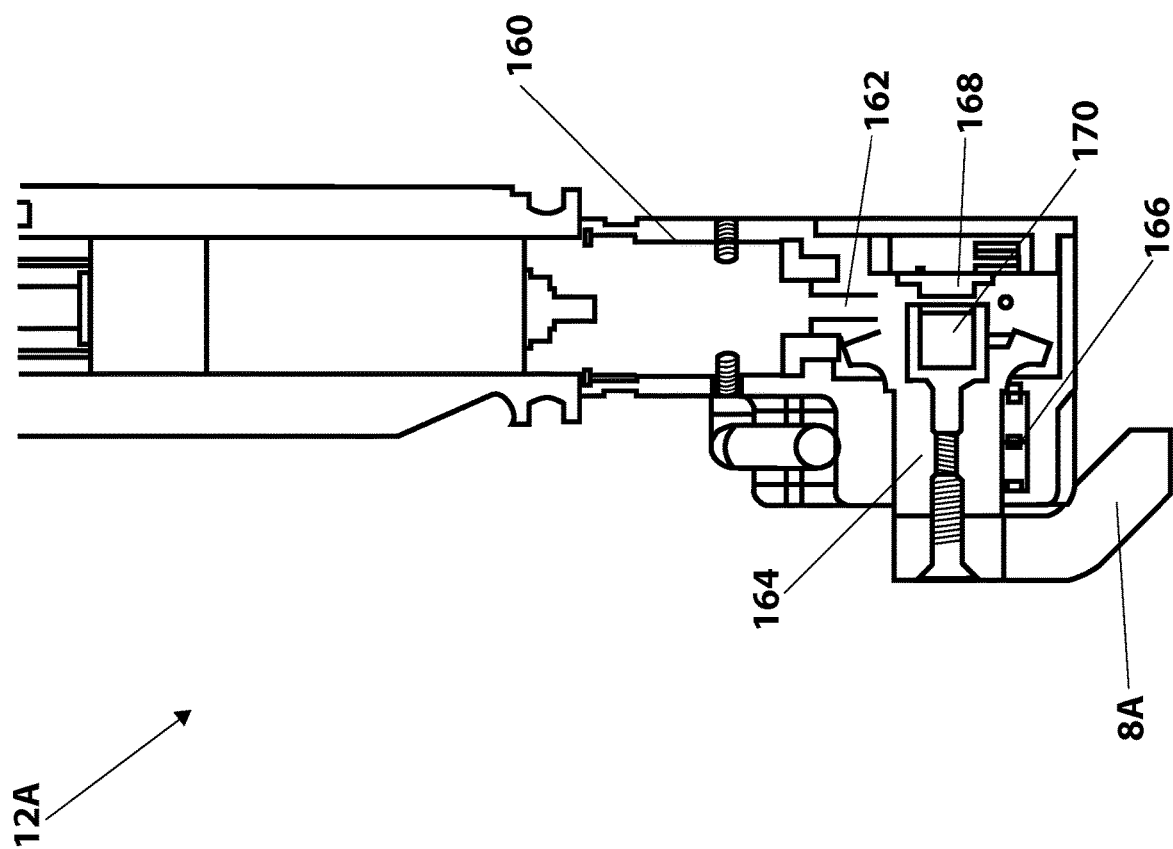

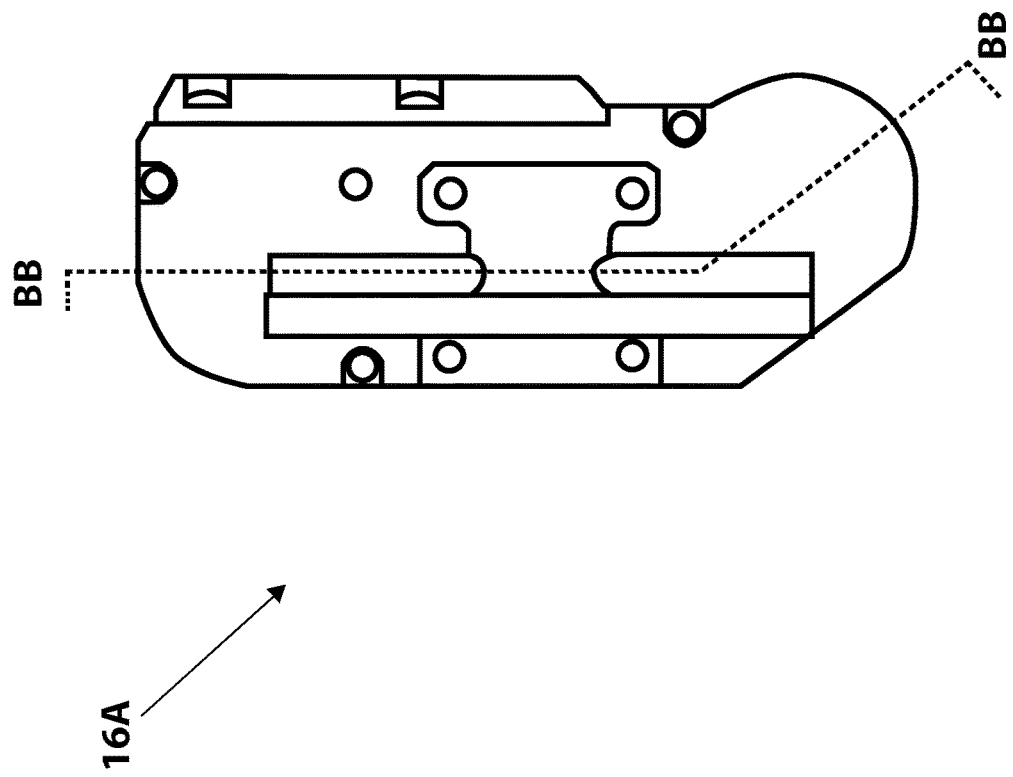

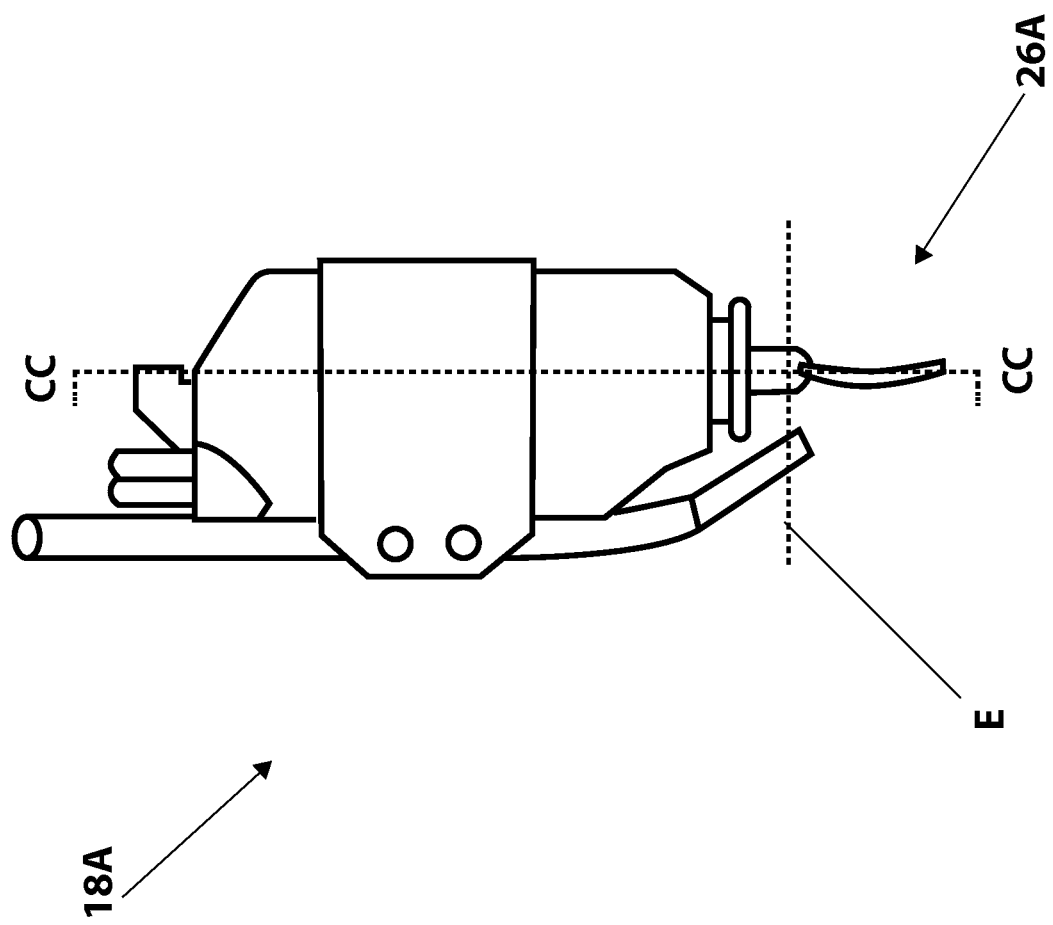

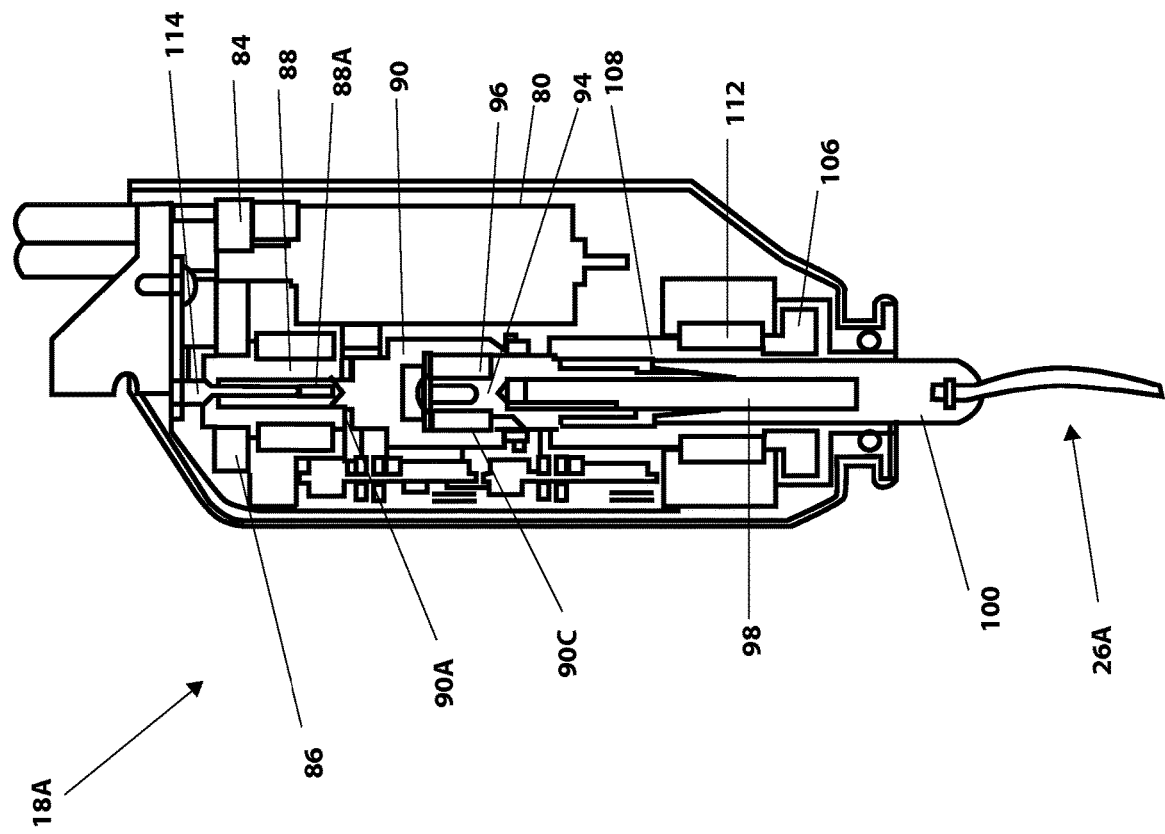

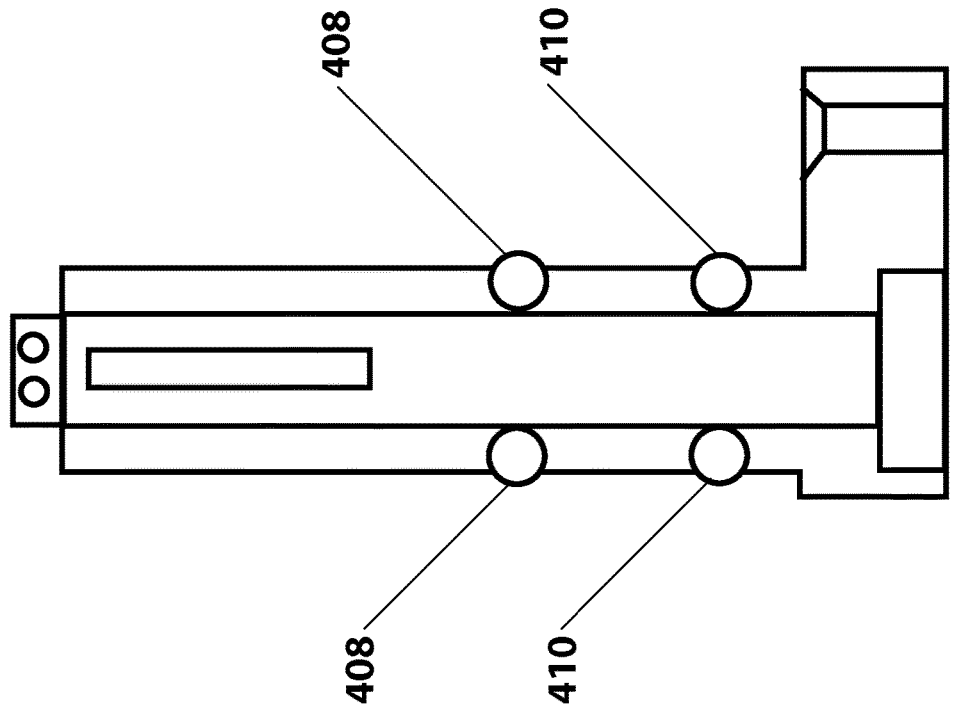

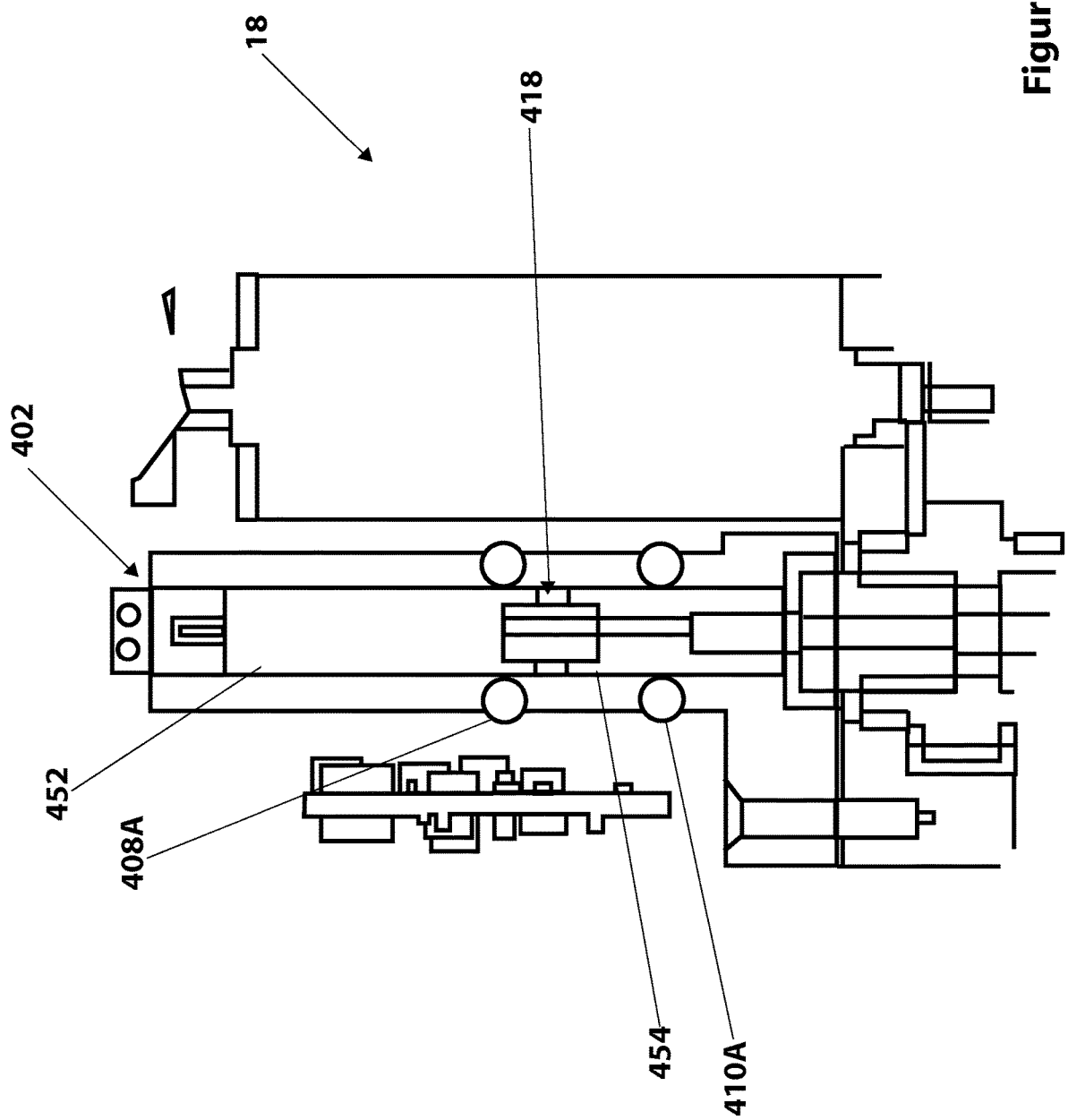

ROBOTIC SURGICAL DEVICES, SYSTEMS, AND RELATED METHODS

CROSS REFERENCE TO RELATED APPLICATIONS

This application claims priority from U.S. Provisional Application 61/680,809, filed Aug. 8, 2012, and entitled "Robotic Surgical Devices, Systems, and Methods," which is hereby incorporated herein by reference in its entirety.

TECHNICAL FIELD

The embodiments disclosed herein relate to various medical devices and related components, including robotic and/or in vivo medical devices and related components. Certain embodiments include various robotic medical devices, including robotic devices that are disposed within a body cavity and positioned using a support component disposed through an orifice or opening in the body cavity. Further embodiment relate to methods of operating the above devices.

BACKGROUND

Invasive surgical procedures are essential for addressing various medical conditions. When possible, minimally invasive procedures such as laparoscopy are preferred.

However, known minimally invasive technologies such as laparoscopy are limited in scope and complexity due in part to 1) mobility restrictions resulting from using rigid tools inserted through access ports, and 2) limited visual feedback. Known robotic systems such as the da Vinci® Surgical System (available from Intuitive Surgical, Inc., located in Sunnyvale, Calif.) are also restricted by the access ports, as well as having the additional disadvantages of being very large, very expensive, unavailable in most hospitals, and having limited sensory and mobility capabilities.

There is a need in the art for improved surgical methods, systems, and devices.

BRIEF DESCRIPTION OF THE DRAWINGS

FIG. 2C is a cut-away view of an arm of a robotic medical device, according to one embodiment.

FIG. 3B is a perspective view of another body portion of a robotic device and related equipment, according to one embodiment.

FIG. 4B is a sideview of the body portion of a robotic device and related equipment, according to one embodiment.

FIG. 5C is a perspective cross-sectional view of a body portion of a robotic device and related equipment, according to one embodiment.

FIG. 5D is a side cross-sectional view of a body portion of a robotic device and related equipment, according to one embodiment.

FIG. 7A is a cross-sectional sideview of the upper arm of a robotic device, according to one embodiment.

FIG. 8A is a sideview of a forearm of a robotic device, according to one embodiment.

FIG. 8C is another cross-sectional view of a forearm of a robotic device, according to one embodiment.

FIG. 11D is another cross-sectional sideview of the embodiment of FIG. 11A.

FIG. 11F is another cross-sectional sideview of the embodiment of FIG. 11A, with associated components in the forearm.

DETAILED DESCRIPTION

Figure 1:
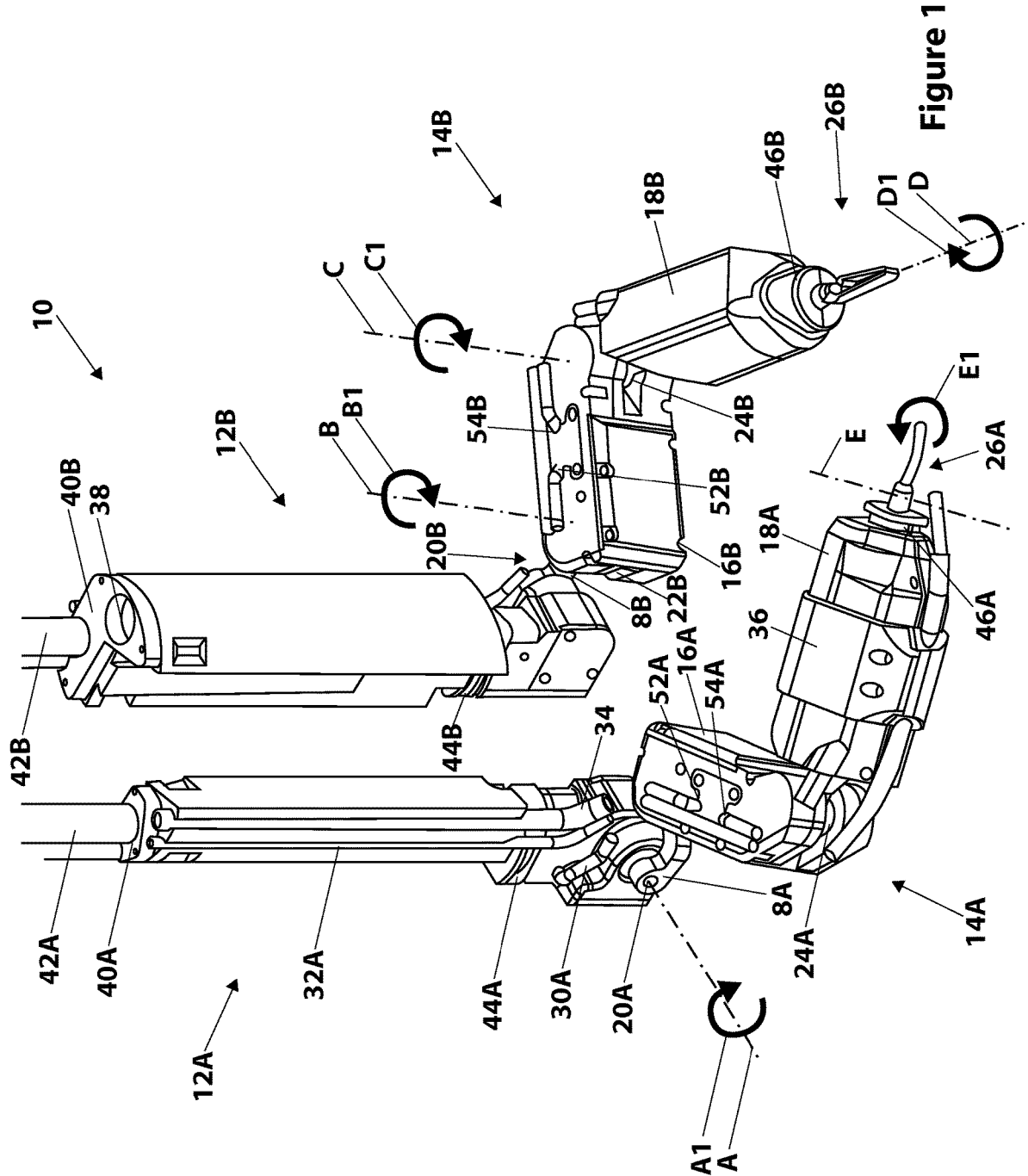
FIG. 1 is a diagram showing a robotic surgical system, including a robotic device positioned inside a body and axis of rotation, according to one embodiment.

The various systems and devices disclosed herein relate to devices for use in medical procedures and systems. More specifically, various embodiments relate to various medical devices, including robotic devices and related methods and systems.

It is understood that the various embodiments of robotic devices and related methods and systems disclosed herein can be incorporated into or used with any other known medical devices, systems, and methods. For example, the various embodiments disclosed herein may be incorporated into or used with any of the medical devices and systems disclosed in copending U.S. application Ser. No. 11/766,683 (filed on Jun. 21, 2007 and entitled "Magnetically Coupleable Robotic Devices and Related Methods"), Ser. No. 11/766,720 (filed on Jun. 21, 2007 and entitled "Magnetically Coupleable Surgical Robotic Devices and Related Methods"), Ser. No. 11/966,741 (filed on Dec. 28, 2007 and entitled "Methods, Systems, and Devices for Surgical Visualization and Device Manipulation"), 61/030,588 (filed on Feb. 22, 2008), Ser. No. 12/171,413 (filed on Jul. 11, 2008 and entitled "Methods and Systems of Actuation in Robotic Devices"), Ser. No. 12/192,663 (filed Aug. 15, 2008 and entitled Medical Inflation, Attachment, and Delivery Devices and Related Methods"), Ser. No. 12/192,779 (filed on Aug. 15, 2008 and entitled "Modular and Cooperative Medical Devices and Related Systems and Methods"), Ser. No. 12/324,364 (filed Nov. 26, 2008 and entitled "Multifunctional Operational Component for Robotic Devices"), 61/640,879 (filed on May 1, 2012), Ser. No. 13/493,725 (filed Jun. 11, 2012 and entitled "Methods, Systems, and Devices Relating to Surgical End Effectors"), Ser. No. 13/546,831 (filed Jul. 11, 2012 and entitled "Robotic Surgical Devices, Systems, and Related Methods"), 61/680,809 (filed Aug. 8, 2012), Ser. No. 13/573,849 (filed Oct. 9, 2012 and entitled "Robotic Surgical Devices, Systems, and Related Methods"), and Ser. No. 13/738,706 (filed Jan. 10, 2013 and entitled "Methods, Systems, and Devices for Surgical Access and Insertion"), and U.S. Pat. No. 7,492,116 (filed on Oct. 31, 2007 and entitled "Robot for Surgical Applications"), U.S. Pat. No. 7,772,796 (filed on Apr. 3, 2007 and entitled "Robot for Surgical Applications"), and U.S. Pat. No. 8,179,073 (issued May 15, 2011, and entitled "Robotic Devices with Agent Delivery Components and Related Methods"), all of which are hereby incorporated herein by reference in their entireties.

Certain device and system implementations disclosed in the applications listed above can be positioned within a body cavity of a patient in combination with a support component similar to those disclosed herein. An "in vivo device" as used herein means any device that can be positioned, operated, or controlled at least in part by a user while being positioned within a body cavity of a patient, including any device that is coupled to a support component such as a rod or other such component that is disposed through an opening or orifice of the body cavity, also including any device positioned substantially against or adjacent to a wall of a body cavity of a patient, further including any such device that is internally actuated (having no external source of motive force), and additionally including any device that may be used laparoscopically or endoscopically during a surgical procedure. As used herein, the terms "robot," and "robotic device" shall refer to any device that can perform a task either automatically or in response to a command.

Certain embodiments provide for insertion of the present invention into the cavity while maintaining sufficient insufflation of the cavity. Further embodiments minimize the physical contact of the surgeon or surgical users with the present invention during the insertion process. Other implementations enhance the safety of the insertion process for the patient and the present invention. For example, some embodiments provide visualization of the present invention as it is being inserted into the patient's cavity to ensure that no damaging contact occurs between the system/device and the patient. In addition, certain embodiments allow for minimization of the incision size/length. Further implementations reduce the complexity of the access/insertion procedure and/or the steps required for the procedure. Other embodiments relate to devices that have minimal profiles, minimal size, or are generally minimal in function and appearance to enhance ease of handling and use.

Certain implementations disclosed herein relate to "combination" or "modular" medical devices that can be assembled in a variety of configurations. For purposes of this application, both "combination device" and "modular device" shall mean any medical device having modular or interchangeable components that can be arranged in a variety of different configurations. The modular components and combination devices disclosed herein also include segmented triangular or quadrangular-shaped combination devices. These devices, which are made up of modular components (also referred to herein as "segments") that are connected to create the triangular or quadrangular configuration, can provide leverage and/or stability during use while also providing for substantial payload space within the device that can be used for larger components or more operational components. As with the various combination devices disclosed and discussed above, according to one embodiment these triangular or quadrangular devices can be positioned inside the body cavity of a patient in the same fashion as those devices discussed and disclosed above.

As best shown in FIG. 1, in certain exemplary embodiments, the device 10 has two coupleable bodies 12A, 12B, each of which is rotatably coupled to one of two arms 14A, 14B as shown. The coupleable bodies 12A, 12B are also referred to as "shoulders," "shoulder assemblies," "connectors," and "connector assemblies." More specifically, each arm 14A, 14B has a coupling link 8A, 8B that couples the arm 14A, 14B to one of the coupleable bodies 12A, 12B. Each arm has an inner link (also referred to herein as an "inner arm," "inner arm assembly," "upper arm," "upper arm assembly," "first link," or "first link assembly") 16A, 16B and an outer link (also referred to herein as an "outer arm," "outer arm assembly," "forearm," "forearm assembly," "second link," or "second link assembly") 18A, 18B. The upper arms 16A, 16B are rotatably coupled to the coupling links 8A, 8B, which are rotatably coupled to the coupleable bodies 12A, 12B. In the right arm 14A, the upper arm 16A is rotatably coupled to the forearm 18A, while in the left arm 14B, the upper arm 16B is rotatably coupled to the forearm 18B.

Figure 5A:
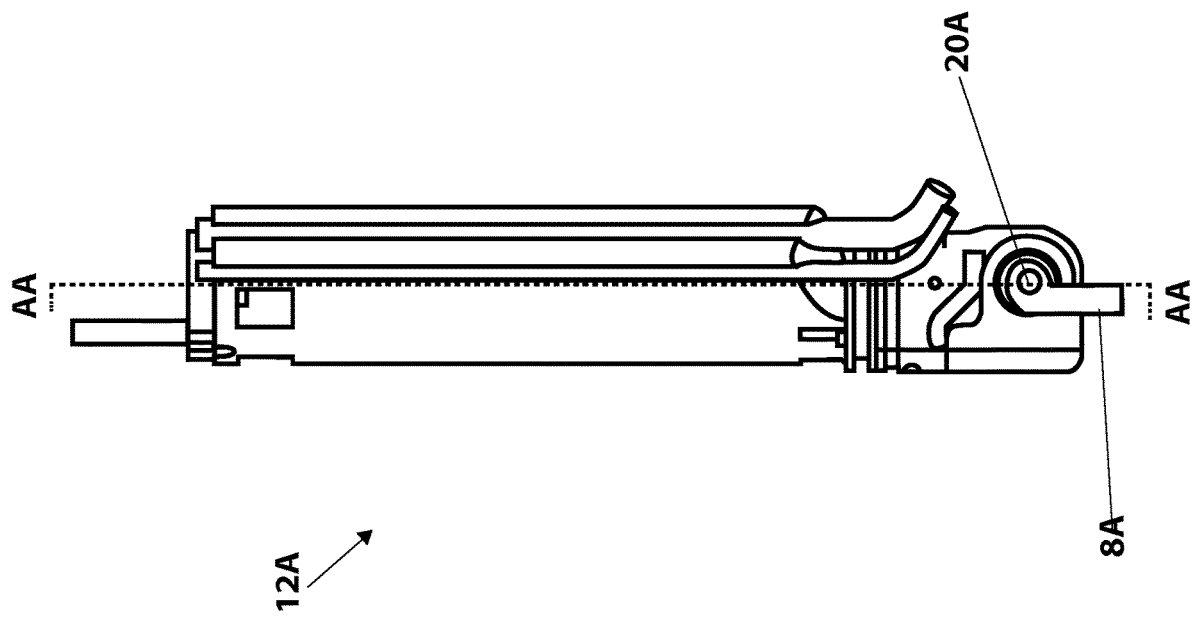
FIG. 5A is a sideview of a body portion of a robotic device and related equipment, according to one embodiment.
Figure 5B:
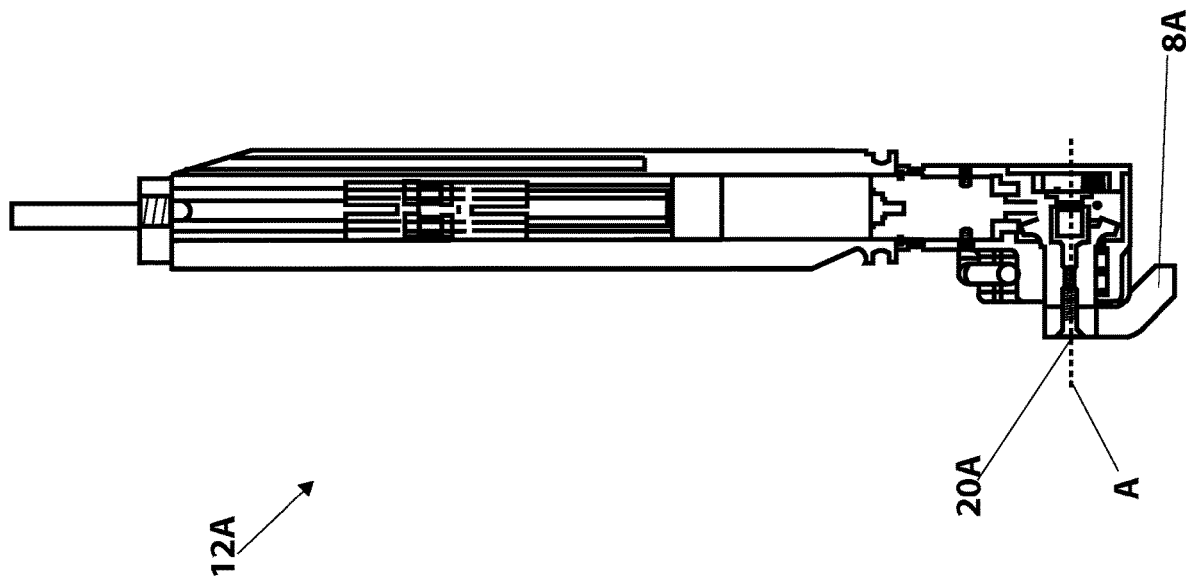
FIG. 5B is a side cross-sectional view of a body portion of a robotic device and related equipment, according to one embodiment.

Each of the arms 14A, 14B has five degrees of freedom. That is, each arm 14A, 14B has four rotatable joints or components and a single bipolar tool. For example, as best shown in FIGS. 1, 5A, and 5B, the coupling link 8A, 8B of each arm 14A, 14B has a rotatable joint 20A, 20B that is rotatable around an axis A that is perpendicular to the length of each of the coupleable bodies 12A, 12B, as shown by arrow A1. The rotatable joints 20A, 20B couple each of the coupleable bodies 12A, 12B to one of the coupling links 8A, 8B. This rotation around axis A is also called "shoulder pitch." FIGS. 5A and 5B depict the right coupleable body 12A. More specifically, FIG. 5A is a sideview of the right body 12A, while FIG. 5B is a cross-sectional cutaway view depicting the internal portion of the body 12A marked by line AA-AA in FIG. 5A. Further, FIG. 5B depicts axis A around which rotatable joint 20A rotates.

Figure 7B:
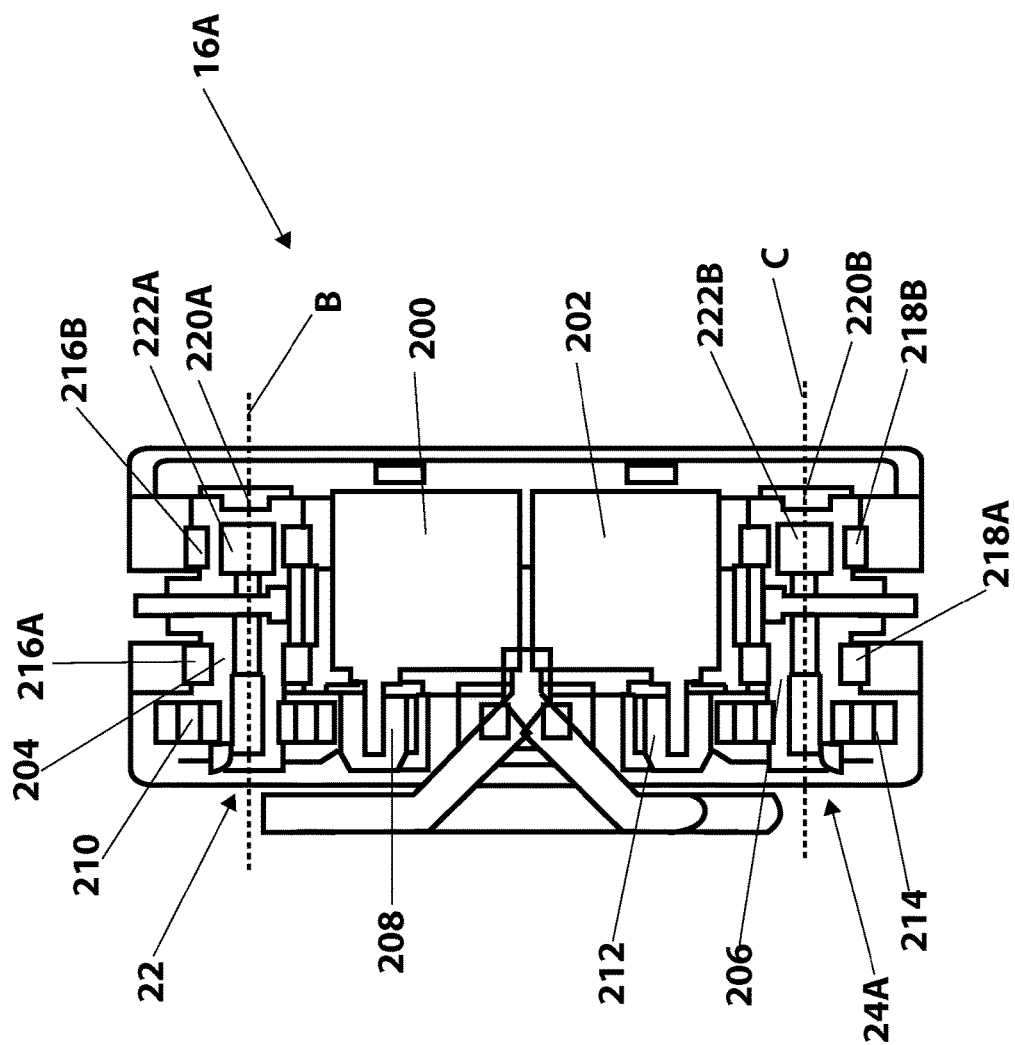
FIG. 7B is a cross-sectional sideview of the upper arm of a robotic device from an alternate view, according to one embodiment.

As best shown in FIGS. 1, 7A, and 7B, the coupling link 8A, 8B of each arm 14A, 14B also has a rotatable joint 22A, 22B that is rotatable around an axis B that is perpendicular to the axis A, as shown by arrow B1. FIGS. 7A and 7B depict the right upper arm 16A. More specifically, FIG. 7A is a top view of the right upper arm 16A, while FIG. 7B is a cross-section cutaway sideview depicted the internal portion of the upper arm 16A marked by line BB-BB in FIG. 7A. FIG. 7B also depicts axis B around which rotatable joint 22A rotates. The rotatable joints 22A, 22B couple the coupling links 8A, 8B to the upper arms 16A, 16B. This rotation around axis B is also called "shoulder yaw."

Also best depicted in FIGS. 1, 7A, and 7B, the arms 14A, 14B each have a rotatable joint 24A, 24B that is rotatable around an axis C that is parallel to axis B, as shown by arrow C1. FIG. 7B depicts axis C around which rotatable joint 24A rotates. The rotatable joints 24A, 24B couple the upper arms 16A, 16B to the forearms 18A, 18B. This rotation around axis C is also called "forearm yaw."

Figure 8B:
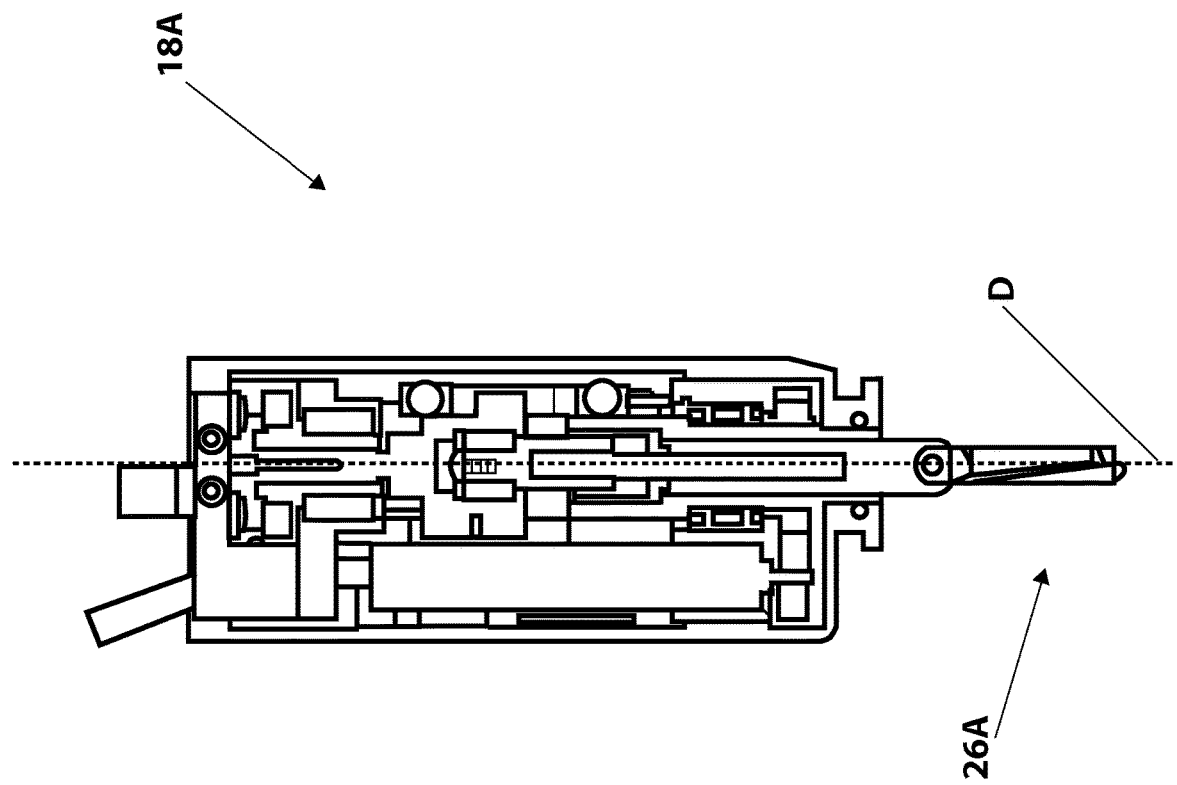
FIG. 8B is a cross-sectional view of a forearm of a robotic device, according to one embodiment.

Additionally, as best shown in FIGS. 1 and 8B, each of the forearms 18A, 18B (or a portion thereof) are configured to rotate around an axis D that is perpendicular to axis C, as shown by arrow D1. This rotation allows for the rotation or "roll" of the end effectors 26A, 26B coupled to the distal end of each of the forearms 18A, 18B. This rotation around axis D is also called "end effector roll."

Further, as best shown in FIGS. 1 and 8A, each of the end effectors 26A, 26B, or, more specifically, certain components thereof, are configured to rotate or move around an axis E that is perpendicular to axis D, as shown by arrow E1. This rotation or movement allows for the opening and closing of the end effector 26A, 26B (also referred to as moving the end effector 26A, 26B between an open and closed position), such as a grasper or gripper or scissors. This rotation around axis E is also called "end effector opening/closing." FIG. 8A is a top view of the right forearm 18A, while FIG. 8B is a cross-section cutaway sideview depicted the internal portion of the forearm 18A marked by line CC-CC in FIG. 8A. FIG. 8A depicts axis E around which the end effector opening/closing occurs, while FIG. 8B depicts axis D around which the end effector roll occurs.

As best shown in FIGS. 1, 2A, 3A, 3B, 4A, and 4B, the two coupleable bodies 12A, 12B are configured to be coupled together. That is, each of the two bodies 12A, 12B have configurations that are mateable to each other such that the right body 12A can mate with and couple to the left body 12B such that the two bodies 12A, 12B form a single body 12. In one example, each of the bodies 12A, 12B have a matching coupling feature that allows the two bodies 12A, 12B to couple together such that they are retained in that coupled configuration. As shown in FIGS. 3A, 3B, 4A, and 4B, the right body 12A has a tapered notch 60 defined in one wall of the body 12A. The notch 60 is wider at the top of the notch 60 than it is at the bottom. Similarly, the left body 12B has a tapered projection 62 that is sized and configured to fit in the notch 60. The projection 62 is wider at the top of the projection 62 than it is at the bottom. In one embodiment, the two bodies 12A, 12B are coupled by positioning the left body 12B such that the bottom portion of the projection 62 can be slid into the top portion of the notch 60 and urged downward such that the projection 62 is positioned in the notch 60. When the projection 62 is correctly positioned in the notch 60, the two bodies 12A, 12B are mated correctly and the coupling is maintained by the mating of the notch 60 and projection 62. Alternatively, any other known mating or coupling feature or mechanism can be used. This coupleability of the two bodies 12A, 12B allows for the two bodies 12A, 12B to be coupled to each other prior to positioning the device 10 into the body or after the two arms 14A, 14B have been inserted into the target body cavity.

The upper arms 16A, 16B and the forearms 18A, 18B are operably coupled to an external controller (not shown) via electrical cables that transport both power and data. In certain embodiments, all six of the segments are operably coupled to such connection components (also referred to herein generally as "connection lines" or "connection components"), including both shoulders. In accordance with one implementation, two such connection components are provided, one for each arm. As best shown in FIG. 2B, in this embodiment the cables are bus power and communication lines 30A, 30B that are disposed in or coupled to the connector 12. The lines 30A, 30B transport power from an external power source (not shown) to the motors (not shown) disposed in the arm segments 16A, 16B, 18A, 18B and further transport data to and from the segments 16A, 16B, 18A, 18B to the controller. According to one embodiment, the proximal end of the lines 30A, 30B are operably coupled to an external source (not shown). According to one embodiment, the external source is an external controller that is a power supply and a communication port. Alternatively, the power supply and the controller can be separate external components. At their distal ends, the power and communication lines 30A, 30B are operably coupled to the microcontrollers and the motors in the arms 14A, 14B as well as the microcontrollers and motors in the shoulders. More specifically, as shown in FIGS. 1 and 2B, the right line 30A extends from the right connector 12A to the right upper arm 16A and is positioned through a hole 52A formed in a top portion of the upper arm 16A. In the upper arm 16A, the line 30A is operably coupled to the at least one microcontroller and the at least one motor (not shown) in the arm 16A. From the upper arm 16A, the line 30A extends out of a hole 54A and to the forearm 18A, where the line 30A is coupled to the at least one microcontroller and the at least one motor (not shown) in the forearm 18A.

Similarly, as also shown in FIGS. 1 and 2B, the left line 30B extends from the left connector 12B to the left upper arm 16B and is positioned through a hole 52B formed in a top portion of the upper arm 16B. In the upper arm 16B, the line 30B is operably coupled to the at least one microcontroller and the at least one motor (not shown) in the arm 16B. From the upper arm 16B, the line 30B extends out of a hole 54B and to the forearm 18B, where the line 30B is coupled to the at least one microcontroller and the at least one motor (not shown) in the forearm 18B. In certain embodiments, the lines 30A, 30B are reinforced or mechanically strain-relieved at the access points to the arm segments (such as holes 52A, 52B, 54A, 54B) to minimize or eliminate damage to the lines 30A, 30B caused by strain as a result of the movement of the arms 14A, 14B. Additionally the lines 30A, 30B are sealed at the access points to prevent fluid ingress into the robot.

Figure 2A:
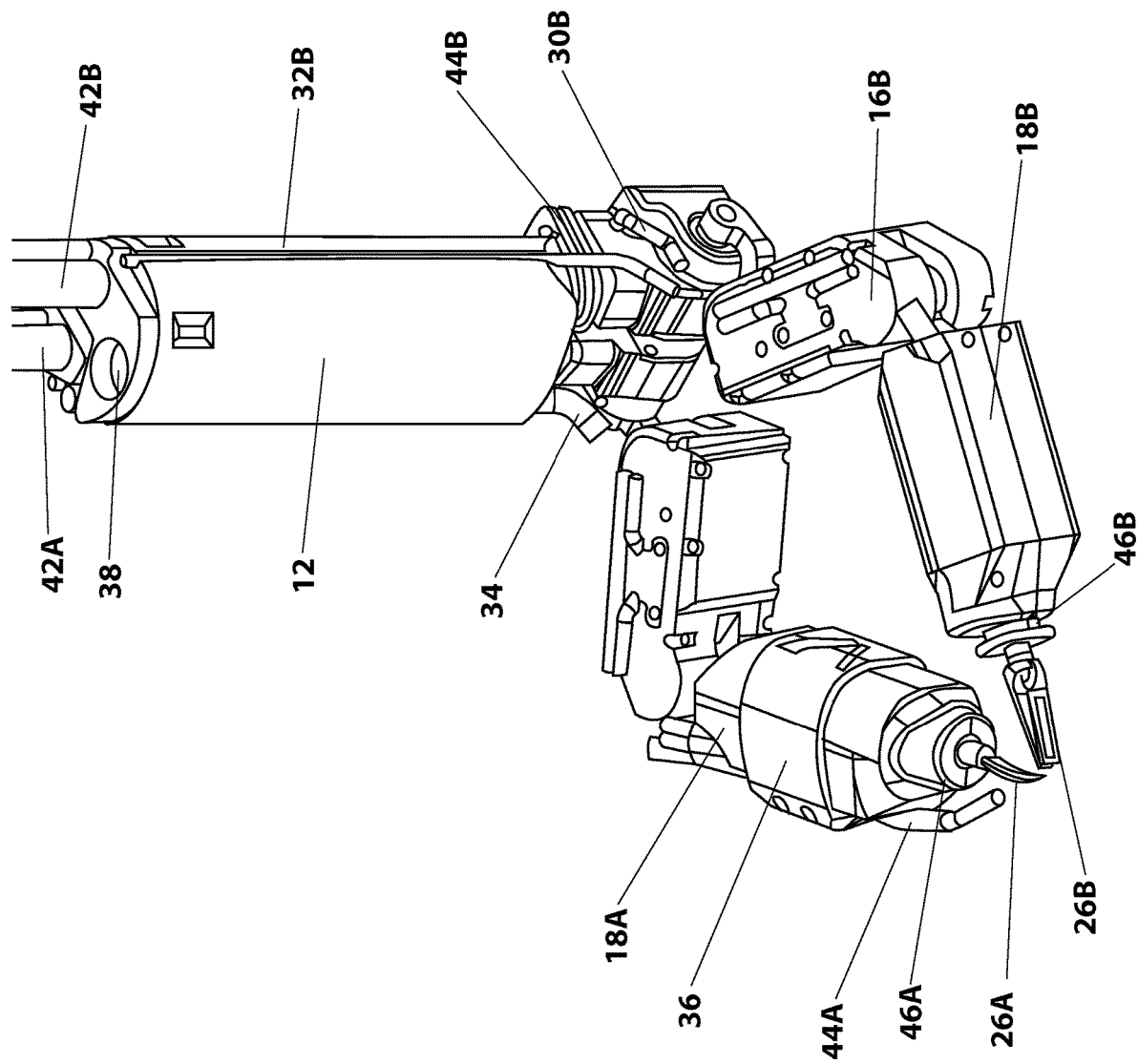
FIG. 2A is a perspective view of a robotic medical device, according to one embodiment.
Figure 2B:
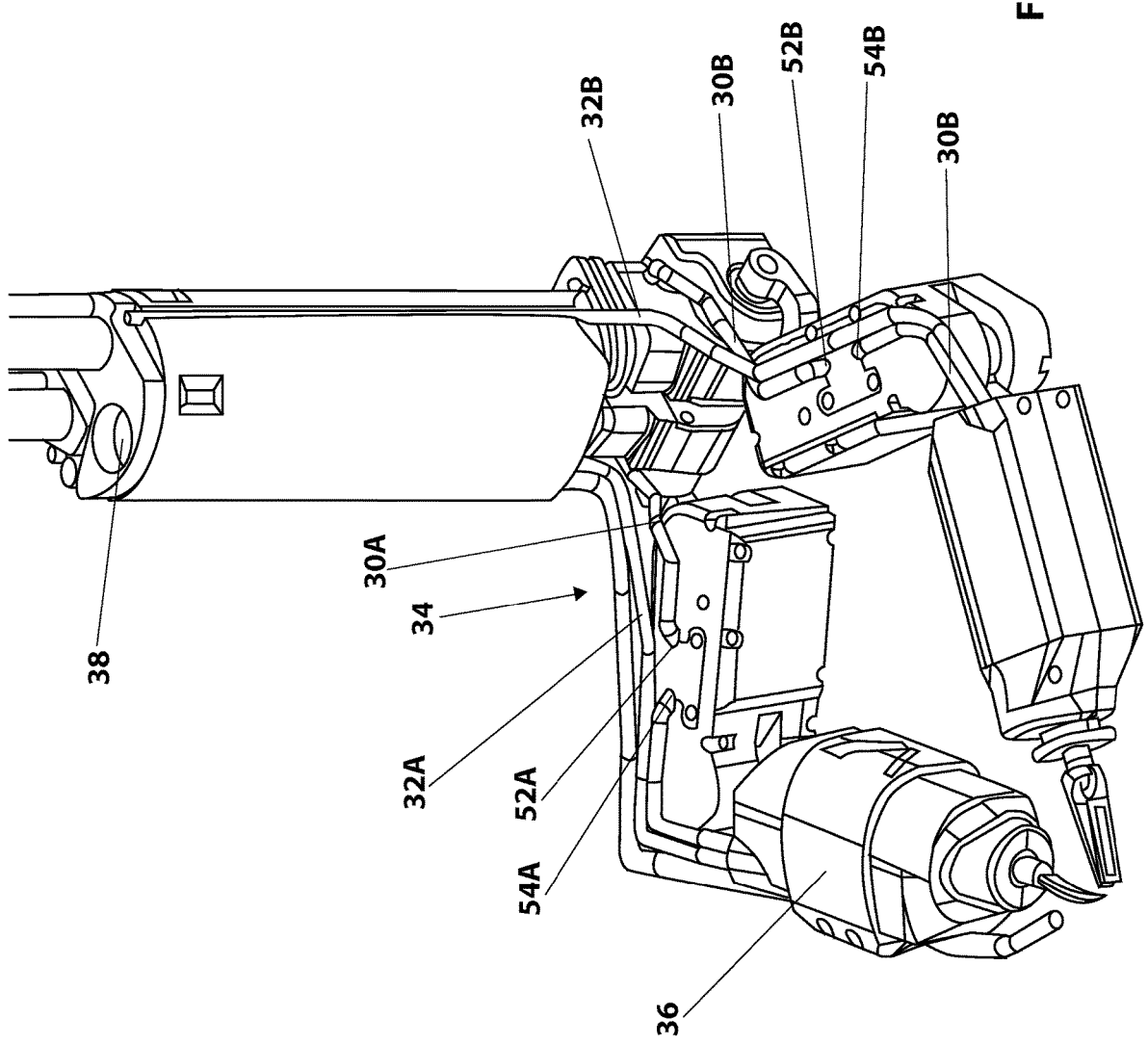
FIG. 2B is a perspective view of a robotic medical device, according to one embodiment.

As best shown in FIGS. 1, 2A, and 2B, two cautery lines 32A, 32B are also disposed in or coupled to the connector 12A, 12B. In this depicted embodiment, the right cautery line 32A is attached to an exterior portion of the right connector 12A (as best shown in FIG. 1), while the left cautery line 32B is attached to an exterior portion of the left connector 12B (as best shown in FIGS. 2A and 2B). The proximal ends of the lines 32A, 32B are coupled to an external power source (not shown). As best shown in FIG. 2B, the right cautery line 32A extends from the right connector 12A to the right forearm 18A, in which the line 32A is operably coupled to the end effector 26A. In one implementation, the portion of the line 32A that extends from the connector 12A to the forearm 18A is coupled to an exterior portion of the upper arm 16A as shown. Alternatively, the line 32A could extend through an interior portion of the upper arm 16A. Similarly, the left cautery line 32B extends from the left connector 12B to the left forearm 18B, in which the line 32B is operably coupled to the end effector 26B. In one implementation, the portion of the line 32B that extends from the connector 12B to the forearm 18B is coupled to an exterior portion of the upper arm 16B as shown. Alternatively, the line 32B could extend through an interior portion of the upper arm 16B.

As best shown in FIGS. 1 and 2B, a dual suction/irrigation line 34A, 34B is also coupled to the connector 12. The dual line 34A, 34B is a known line that is comprised of at least one line that can be alternatively used for suction or irrigation. In certain other embodiments, more than one line can be provided, thus providing for suction and irrigation. In the embodiment depicted in FIGS. 1 and 2B, at its proximal end, the dual suction/irrigation line 34 is coupled to an external irrigation/suction component (not shown) that provides suction or irrigation to the lumen. In one embodiment, the line 34A, 34B is coupled at its proximal end to a valve having two separate lines: one line extending to a known suction device and the other line extending to a known irrigation device. This commercially-available valve is known generally as a "trumpet valve." Alternatively, the dual line 34A, 34B is coupled to any known external component that provides suction and irrigation, or is coupled to two separate devices, one providing suction and the other providing irrigation. Alternatively, it is understood that two separate lines can be provided—a suction line and an irrigation line. In this embodiment, the dual suction/irrigationline 34A is coupled to an exterior portion of the right connector 12A. The suction/irrigation line 34A extends from the right connector 12A to the right arm 14A, where the line 34A is coupled to an exterior portion of the upper arm 16A and to an exterior portion of the forearm 18A as shown.

In one embodiment, the forearm 18A has an attachment component 36 configured to couple the suction/irrigation line 34 to the forearm 18A. In this particular exemplary embodiment, the attachment component 36 is an attachment collar 36 configured to be positioned around the forearm 18A and coupled to the line 34 such that the collar 36 helps to keep the line 34 coupled to the forearm 18A. At its distal end, the dual suction/irrigation line 34 is operably coupled to the cautery scissors 26A.

As shown in FIGS. 2A and 2B, the connector 12 has a laparoscope lumen 38 defined in the connector 12. The lumen 38 is configured to receive any standard laparoscopic imaging device. Further, each of the two coupleable connectors 12A, 12B defines an insertion rod lumen 40A, 40B. Each lumen 40A, 40B is configured to receive an insertion rod 42A, 42B.

Figure 6:
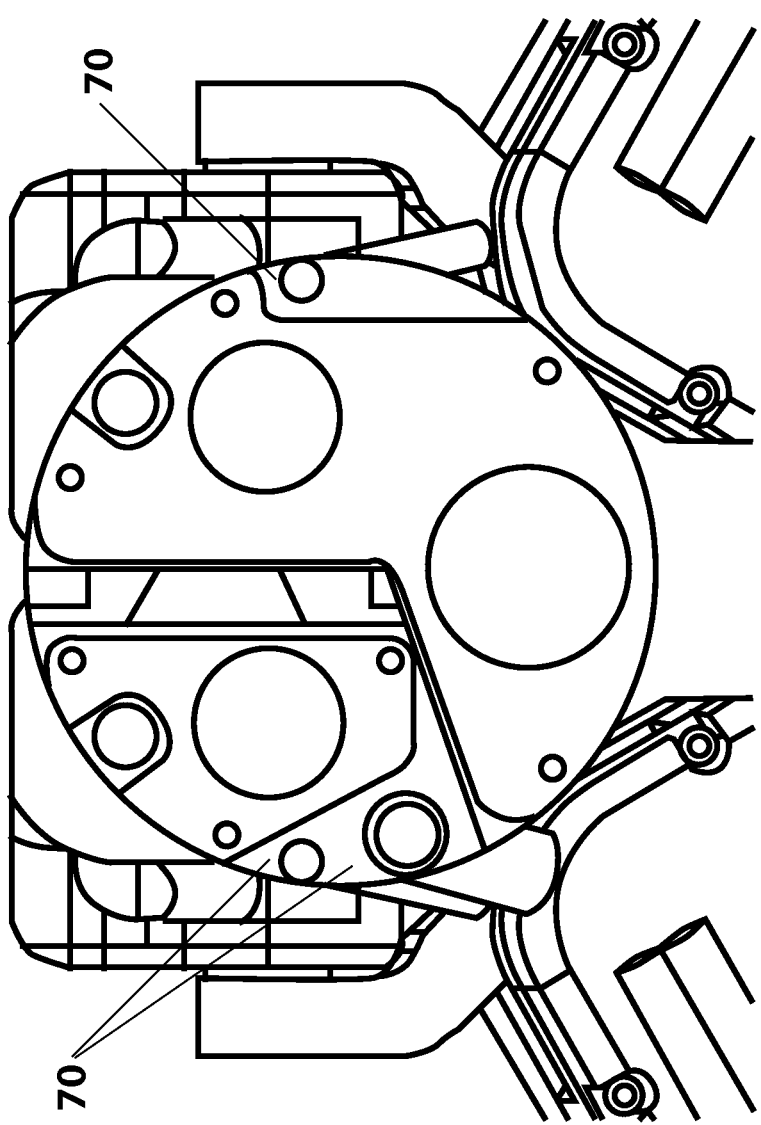
FIG. 6 is an endlong cross-sectional view of a body portion of a robotic device, according to one embodiment.

In accordance with one implementation, each of the power and communications lines 30A, 30B, the cautery lines 32A, 32B, and the dual suction/irrigation line 34 are all coupled with or disposed in the connector 12 such that a seal is maintained between the connector 12 and the access port (not shown) mounted to the patient. That is, as best shown in FIG. 6, the connector 12 (and the two connector bodies 12A, 12B), according to one embodiment, has grooves or channels 70 defined along the outer surface of the two bodies 12A, 12B such that the various lines and cables (including the power and communications lines 30A, 30B, the cautery lines 32A, 32B, the suction/irrigation line 34, and any other lines or cables that might be incorporated into the device) are positioned in those grooves or channels 70. The positioning of the lines or cables in the grooves or channels 70 helps to maintain a smooth outer perimeter around the outer surface of the connector 12, thereby ensuring a successful fluidic seal with the access port when the connector 12 is positioned therethrough. It is understood that the access port can be any known port for use with laparoscopic surgical tools, including the port devices described in U.S. patent application Ser. No. 13/738,706, filed on Jan. 10, 2013, which is hereby incorporated herein by reference in its entirety. In certain exemplary embodiments, the access port can be readily removed, cleaned and sterilized.

According to one implementation, the arms 14A, 14B are configured to receive a fluid sealing component over the arms 14A, 14B. That is, as best shown in FIG. 1, each of the coupleable connectors 12A, 12B, has a channel 44A, 44B defined around the connectors 12A, 12B and each of the arms 14A, 14B has a channel 46A, 46B defined around a distal portion of the forearms 18A, 18B. Fluid sealing protective sleeves (not shown), such as those, for example, described in U.S. application Ser. No. 13/573,849, filed on Oct. 9, 2012, which is hereby incorporated by reference herein in its entirety, are positioned over each arm 14A, 14B and the ends of each sleeve are positioned in one of the channels 44A, 44B, 46A, 46B such that the sleeves are coupled to the arms 14A, 14B such that the sleeves create a fluidic seal around each arm 14A, 14B, whereby moisture and liquid are prevented from ingressing into the arms 14A, 14B.

Each of the joints described above is operably coupled to a motor via a geartrain (not shown). Further, each joint is also operably coupled to a microcontroller. In addition, each joint is operably coupled to at least one position sensor. According to one embodiment, each joint is coupled to both a relative position sensor and an absolute position sensor. According to another embodiment, each joint has at least a relative position sensor.

Figure 2D:
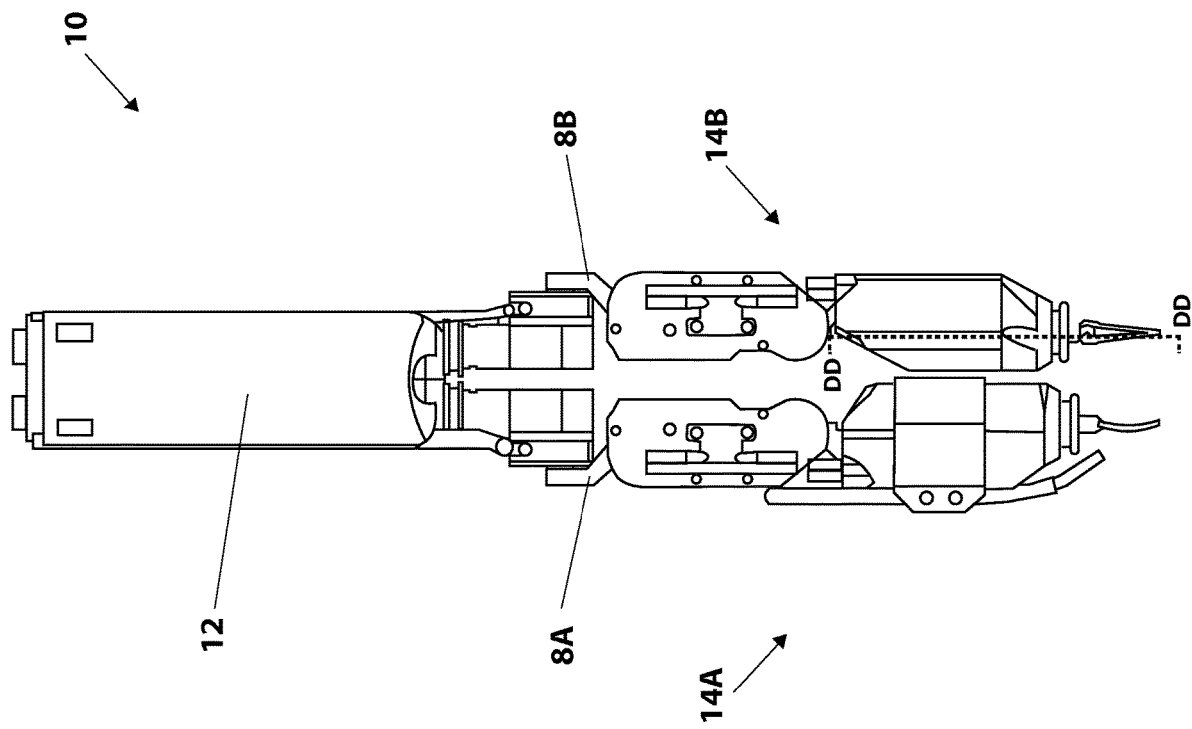
FIG. 2D is a sideview of a robotic medical device, according to one embodiment.
Figure 3A:
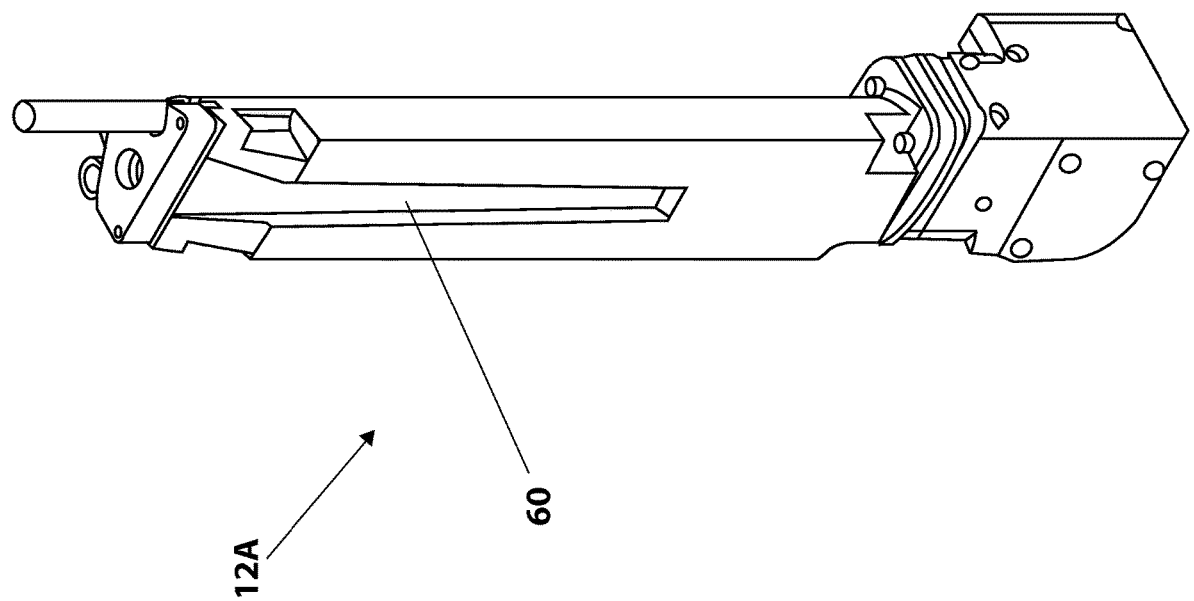
FIG. 3A is a perspective view of a body portion of a robotic device and related equipment, according to one embodiment.
Figure 4A:
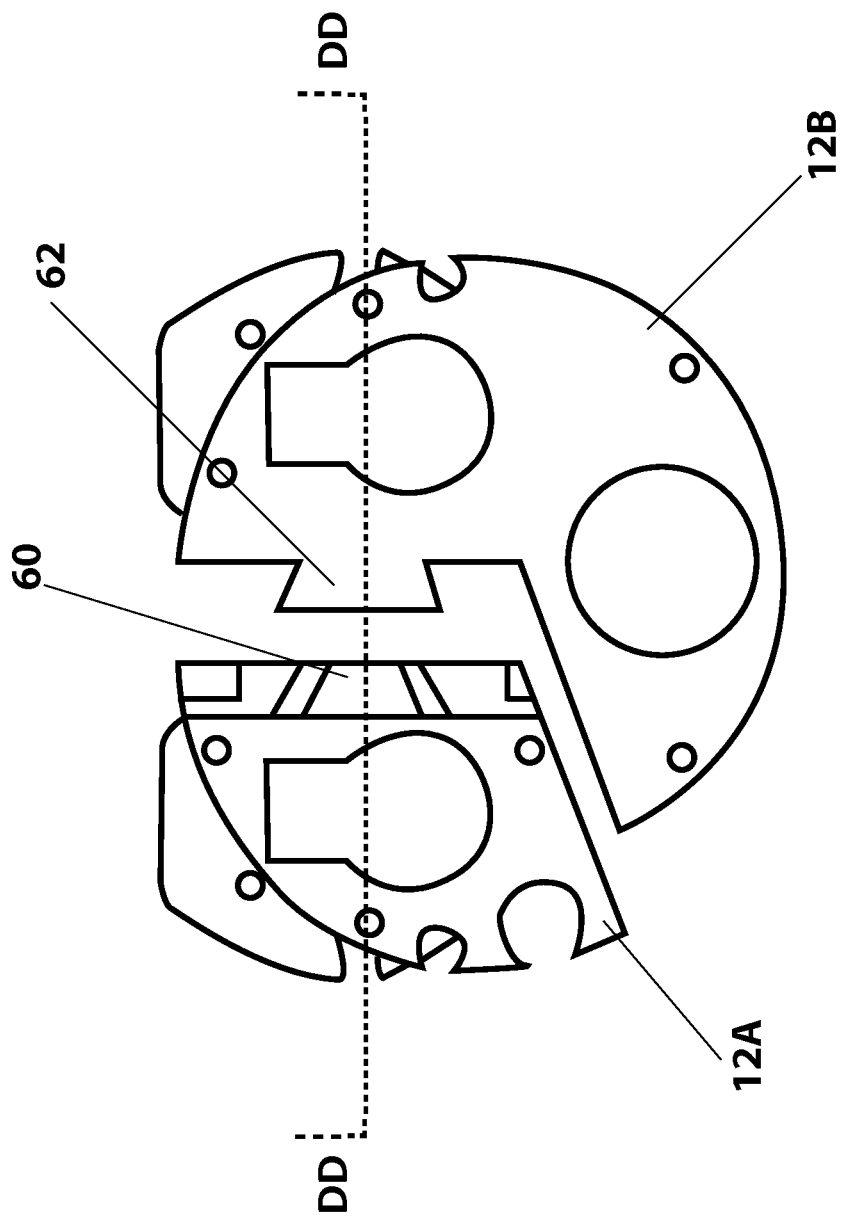
FIG. 4A is an endlong view of the body portion of a robotic device and related equipment, according to one embodiment.

As best shown in FIGS. 2C and 2D, the configuration of the connector 12 and the arms 14A, 14B in this embodiment provide a minimal cross-sectional area for the device 10, thereby allowing for easy insertion of the device 10 through a small incision and into a small cavity of a patient. That is, the coupling of the arms 14A, 14B to the connector 12 via the coupling links 8A, 8B, along with the ability to position the arms 14A, 14B as shown in FIGS. 2C and 2D, results in a narrower device 10 that can fit through smaller incisions in comparison to devices that are wider/have larger cross-sections. In use, the arms 14A, 14B of the device 10 can be positioned as shown in these figures prior to insertion into a patient's cavity. The device 10 can then be positioned through an incision in a single linear motion. In one embodiment, the device 10 is inserted one arm at a time. That is, the two coupleable bodies 12A, 12B with arms attached are positioned in the patient's cavity prior to coupling the two bodies 12A, 12B together. Alternatively, the device 10 is inserted as a single unit, with the two bodies 12A, 12B already coupled together.

FIGS. 5C and 5D depict a close-up of the right connector 12A, according to one embodiment. It is understood that the internal components of the right connector 12A as described herein are substantially similar to the equivalent components in the left connector 12B, so the following description shall encompass those equivalent components as well. As best shown in FIG. 5D, the right connector 12A has a connector motor 160 that is operably coupled to a bevel motor gear 162. The bevel motor gear 162 is operably coupled to a bevel driven gear 164, which constitutes joint 20A discussed above. The drive gear 164 is supported in this embodiment by two bearings 166 and is operably coupled to the right coupling link 8A, which is also described above. In one implementation, a magnetic absolute position encoder 168 (also shown in FIG. 5C) and an encoder magnet 170 are operably coupled to the driven gear 164, and are thereby configured to provide information about the position of the gear 164. As best shown in FIG. 5C, a motor control board 172 is positioned in the housing of the connector 12A.

In accordance with one embodiment, the right and left upper arms 16A, 16B, including the coupling links 8A, 8B, have configurations that are identical or substantially similar and are simply minor versions of each other. Alternatively, they can have some different components as necessary for the specific end effectors that might be coupled to the forearms 18A, 18B.

Figure 7C:
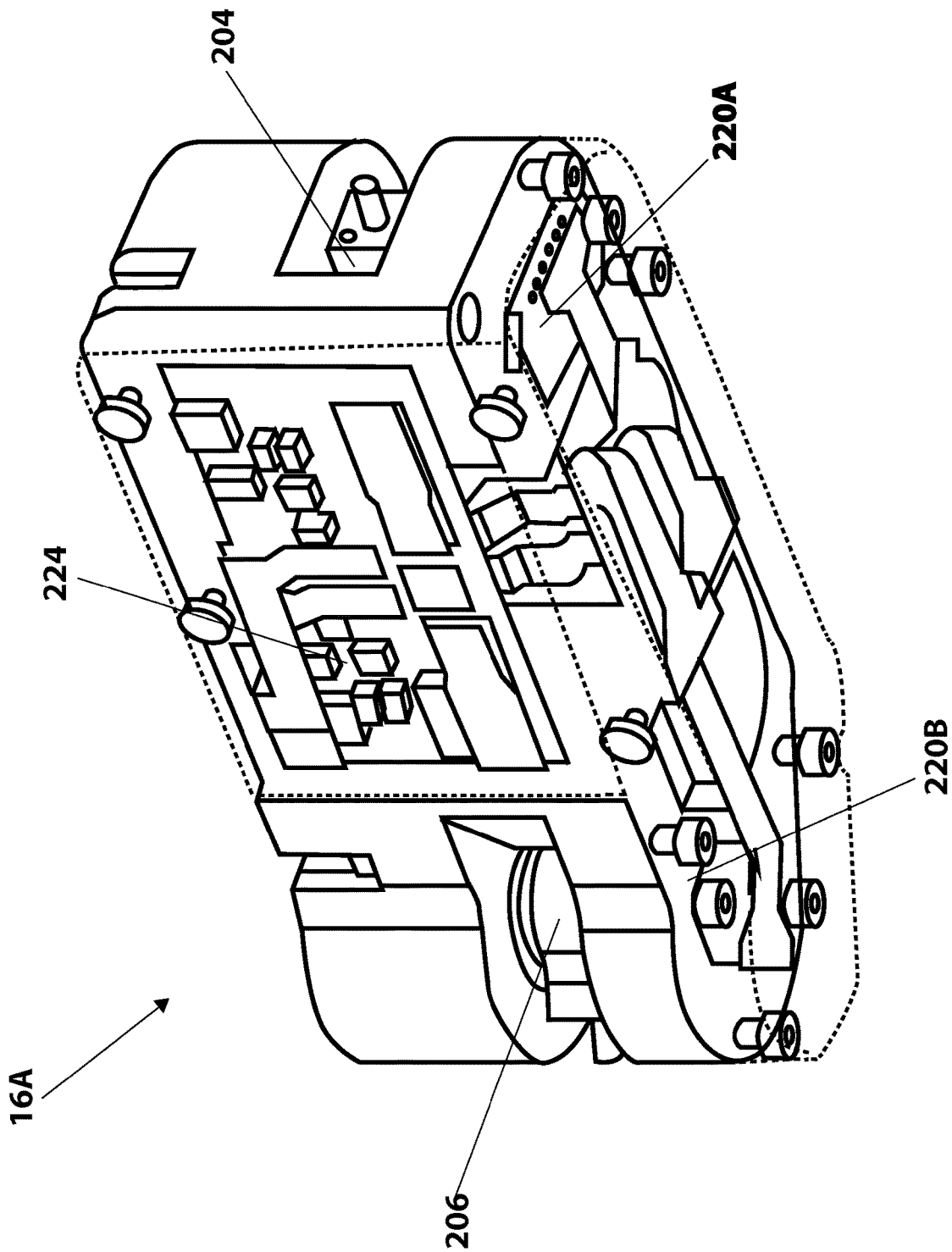
FIG. 7C is a perspective internal view of the upper arm of a robotic device, according to one embodiment.

FIGS. 7A, 7B, and 7C depict a right upper arm 16A, according to one embodiment. It is understood that the internal components of the right upper arm 16A as described herein are substantially similar to the equivalent components in the left upper arm 16B, so the following description shall encompass those equivalent components as well. The upper arm 16A has two motors 200, 202. The first motor 200 is configured to actuate the shoulder shaft 204 to rotate in relation to the coupling link 8A, thereby rotating around axis B. The second motor 202 is configured to actuate the elbow shaft 206 to rotate in relation to the forearm 18A, thereby rotating around axis C.

As best shown in FIG. 7B, the first motor 200 is operably coupled to motor gear 208, which is operably coupled to the driven gear 210. The driven gear 210 is operably coupled to the shoulder shaft 204 such that rotation of the driven gear 210 causes rotation of the shoulder shaft 204. The shaft 204 is supported by bearings 216A, 216B. The motor 202 is operably coupled to motor gear 212, which is operably coupled to the driven gear 214. The driven gear 214 is operably coupled to the elbow shaft 206 such that rotation of the driven gear 214 causes rotation of the elbow shaft 206. The shaft 206 is supported by bearings 218A, 218B.

Each of the shafts 204, 206 is operably coupled to an encoder magnet 222A, 222B, each of which is operably coupled to an absolute position magnetic encoder 220A, 220B. The encoders 220A, 220B work in a fashion similar to the position encoders described above. At least one motor control board 224 is positioned in the housing of the upper arm 16A as best shown in FIG. 7C.

In contrast, in this implementation as shown in FIGS. 1 and 2A, the right and left forearms 18A, 18B are not identical. That is, the right forearm 18A has an end effector 26A further comprising cautery scissors 26A. According to one embodiment, the cautery scissors 26A is a "quick-change" mono-polar cautery scissors 26A. That is, the cautery scissors 26A can be coupled to or removed from the forearm 18A without the need to assemble or disassemble any other components. More specifically, in this exemplary embodiment, a commercially-available cautery scissors 26A called the ReNew Laparoscopic Endocut Scissors Tip™, which is available from Microline Surgical, Inc., located in Beverly, Mass., is removeably coupled to the forearm 18A. Alternatively, any known easily removeable end effector or any known mechanism or method for providing easy coupling and uncoupling of the end effector 26A can be used. In a further alternative, the end effector 26A can be any known end effector for use with an arm of a robotic surgical device.

Figure 8D:
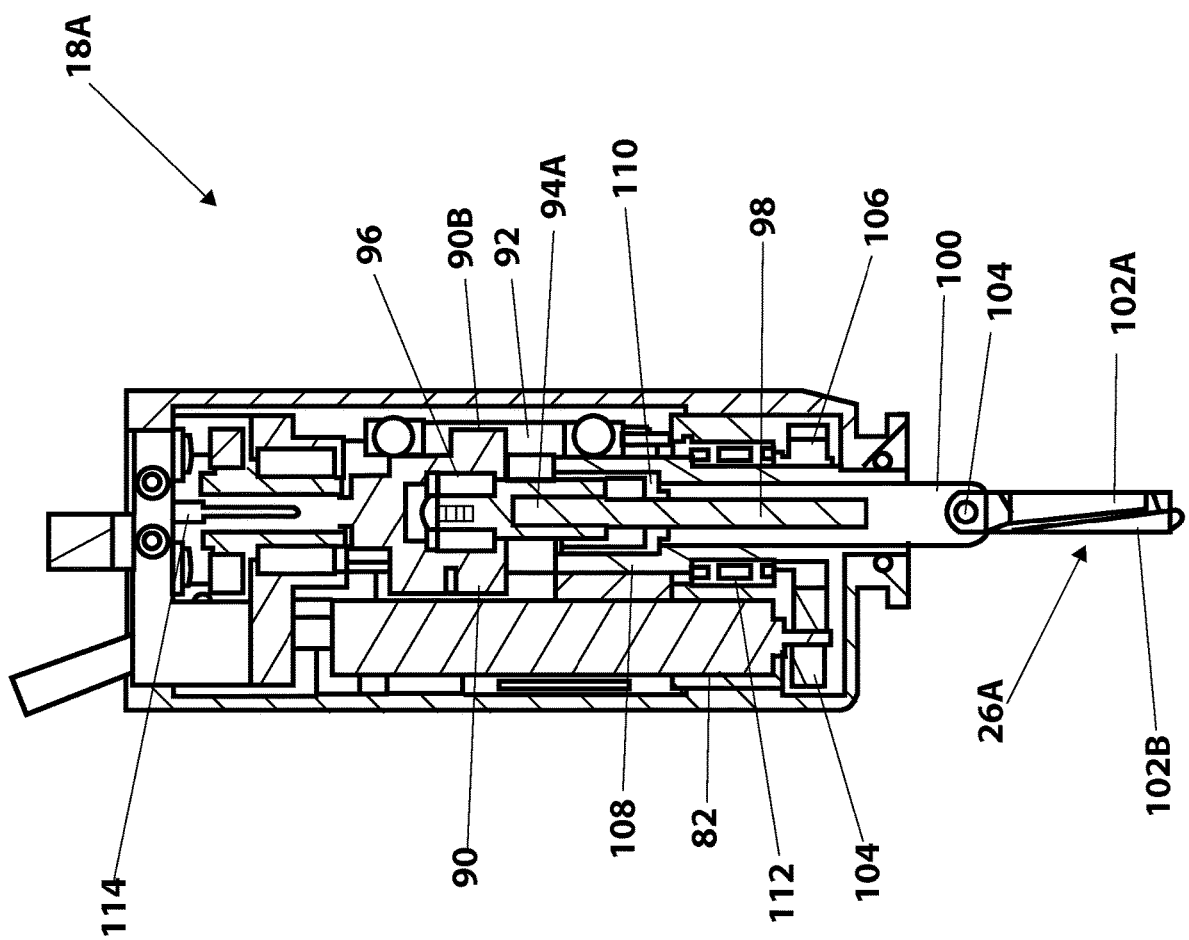
FIG. 8D is yet another cross-sectional view of a forearm of a robotic device, according to one embodiment.

One exemplary embodiment is depicted in FIGS. 8A-8D. FIGS. 8A-8D depict several views of the right forearm 18A according to one implementation. FIG. 8C is a cross-sectional cutaway view of the forearm 18A that is perpendicular to the plane of the line CC-CC of FIG. 8A, while FIG. 8D is a cross-sectional cutaway view of the forearm along line CC-CC of FIG. 8A. The forearm 18A has two motors 80, 82. As best shown in FIG. 8C, the motor 80 is operably coupled to the end effector 26A such that the motor 80 actuates the end effector 26A to move between its open and closed positions. As best shown in FIG. 8D, the motor 82 is operably coupled to the end effector 26A such that the motor 82 actuates the end effector 26A to "roll," which is rotation around an axis parallel to the longitudinal length of the arm 18A.

Focusing on FIG. 8C, the motor 80 actuates the end effector 26A to open and close in the following fashion. The motor 80 has a motor gear 84 that is operably coupled to a driven gear 86. The driven gear 86 is operably coupled to a connector component 88 such that the connector component 88 rotates when the driven gear 86 rotates. Connector component 88 is supported by two bearings (not shown). The connector component 88 has a threaded inner lumen 88A and is operably coupled to a translation component 90. More specifically, the translation component 90 has a proximal threaded projection 90A that is threadably coupled to the threaded inner lumen 88A such that rotation of the connector component 88 causes axial movement of the translation component 90. In addition, as best shown in FIG. 8D, the translation component 90 has a projection 90B extending from an outer circumference of the component 90 such that the projection 90B is positioned in a slot 92 that constrains the translation component 90 from rotating. As such, when the driven gear 86 rotates and thus causes the connector component 88 to rotate, the rotation of the connector component 88 causes the translation component 90 to move axially along the longitudinal axis of the arm 18A.

The translation component 90 defines a lumen 90C at its distal end that is configured to receive the coupling component 94, as best shown in FIG. 8C. Further, the lumen 90C contains at least one bearing 96 that is positioned between the translation component 90 and the coupling component 94 such that the translation component 90 and the coupling component 94 are rotationally independent of each other. That is, the coupling component 94 can rotate inside the lumen 90C of the translation component 90 while the translation component 90 does not rotate. The coupling component 94 has a threaded lumen 94A configured to receive a rod (or pin) 98 that has external threads on its proximal end that are threadably coupled to the threaded lumen 94A of the coupling component 94. The distal end of the rod 98 is slidably positioned in the end effector housing 100 such that the rod 98 can slide axially back and forth in relation to the housing 100. The rod 98 is operably coupled to the first and second blades 102A, 102B of the scissors 26A via linkages (not shown) such that the axial movement of the rod 98 causes the blades 102A, 102B to pivot around the pivot axis 104, thereby causing the blades 102A, 102B to open and close. More specifically, in one embodiment, movement of the rod 98 in a distal direction (toward the scissors 26A) causes the blades 102A, 102B to move away from each other such that the scissors 26A move toward an open position, while proximal movement of the rod 98 causes the scissors 26A to move toward a closes position.

Focusing on FIG. 8D, the motor 82 actuates the end effector 26A to roll in the following fashion. The motor 82 has a motor gear 104 that is operably coupled to a driven gear 106. The driven gear 106 is operably coupled to a roll shaft 108 such that the roll shaft 108 rotates when the driven gear 106 rotates. The at least one bearing 112 disposed around the roll shaft 108 allows the roll shaft 108 to rotate in relation to the forearm 18A. The roll shaft 108 is operably coupled to rotational connector 110, such that roll shaft is constrained linearly and rotationally. Housing 100 is threadably coupled to rotational connector 110, such that the two components are operably coupled, again constrained linearly and rotationally. In certain embodiments, roll shaft 108 does not have any threads. As such, the roll shaft 108, the housing 100, and the rotational connector 110 are all coupled together such that they are capable of rotating together. Thus, actuation of the motor 82 results in rotation of the housing 100 and thus rotation of the end effector 26A. According to one embodiment, the forearm 18A also has at least one position sensor to provide information to an external controller (not shown) or a microcontroller regarding the position of the end effector 26A.

The electrical connection required for the cautery feature of the end effector 26A is maintained in the following fashion. An electrical contact pin 114 is slidably positioned within the lumen 88A of the connector component 88 and is electrically coupled at its proximal end to the cautery line 32A discussed elsewhere herein (and depicted in FIGS. 1 and 2B). The lumen 88A contains bifurcated leaf springs which maintain electrical contact and provide long life to mechanism. This was accomplished by taking an off the shelf socket connector and press fitting the socket portion into part 88. At its distal end, the pin 114 is electrically coupled to the translation component 90, which is electrically coupled through the other coupling components discussed above to the blades 102A, 102B of the end effector 26A, thereby allowing for electrical coupling of the cautery line 32A to the end effector 26A.

Figure 9A:
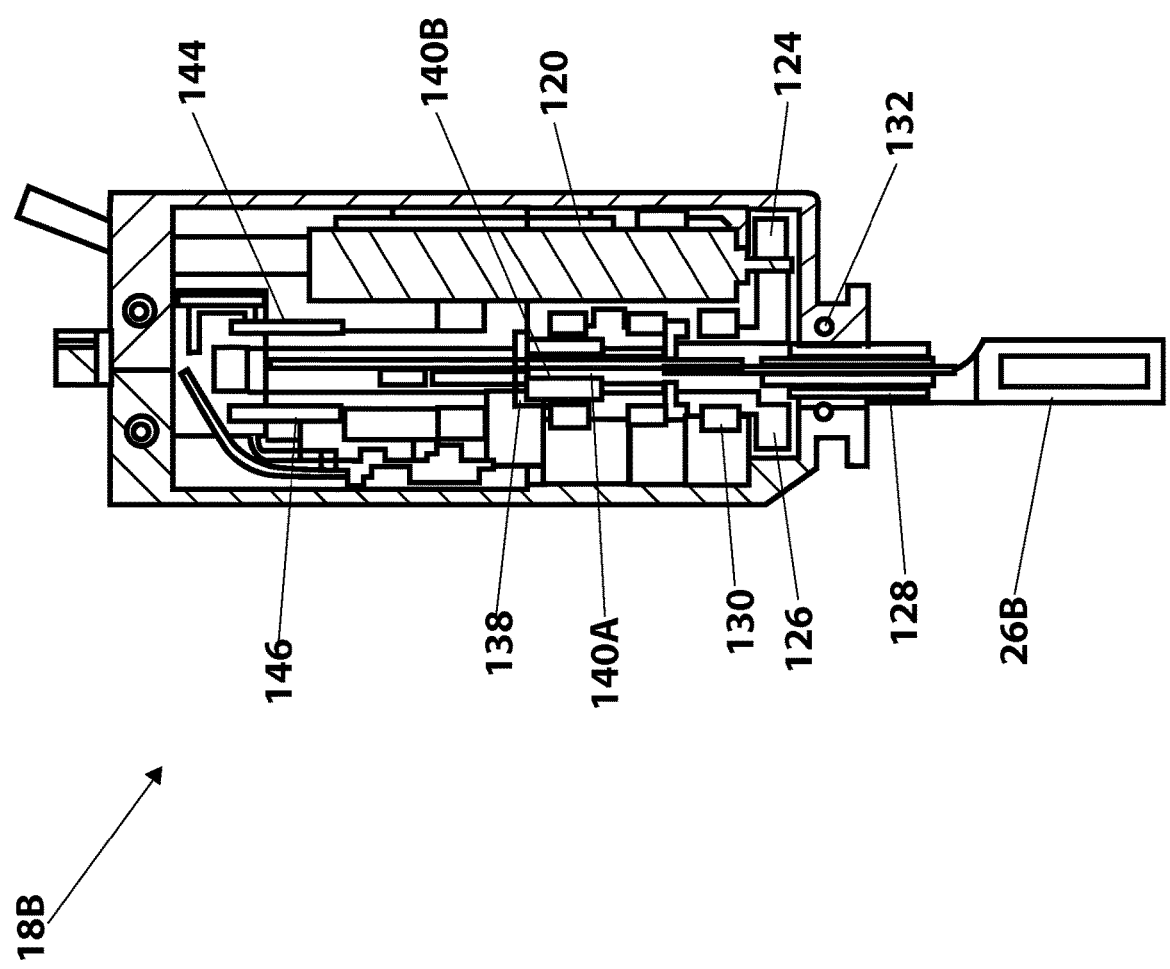
FIG. 9A is cross-sectional sideview of the forearm of a robotic device, according to another embodiment.
Figure 9B:
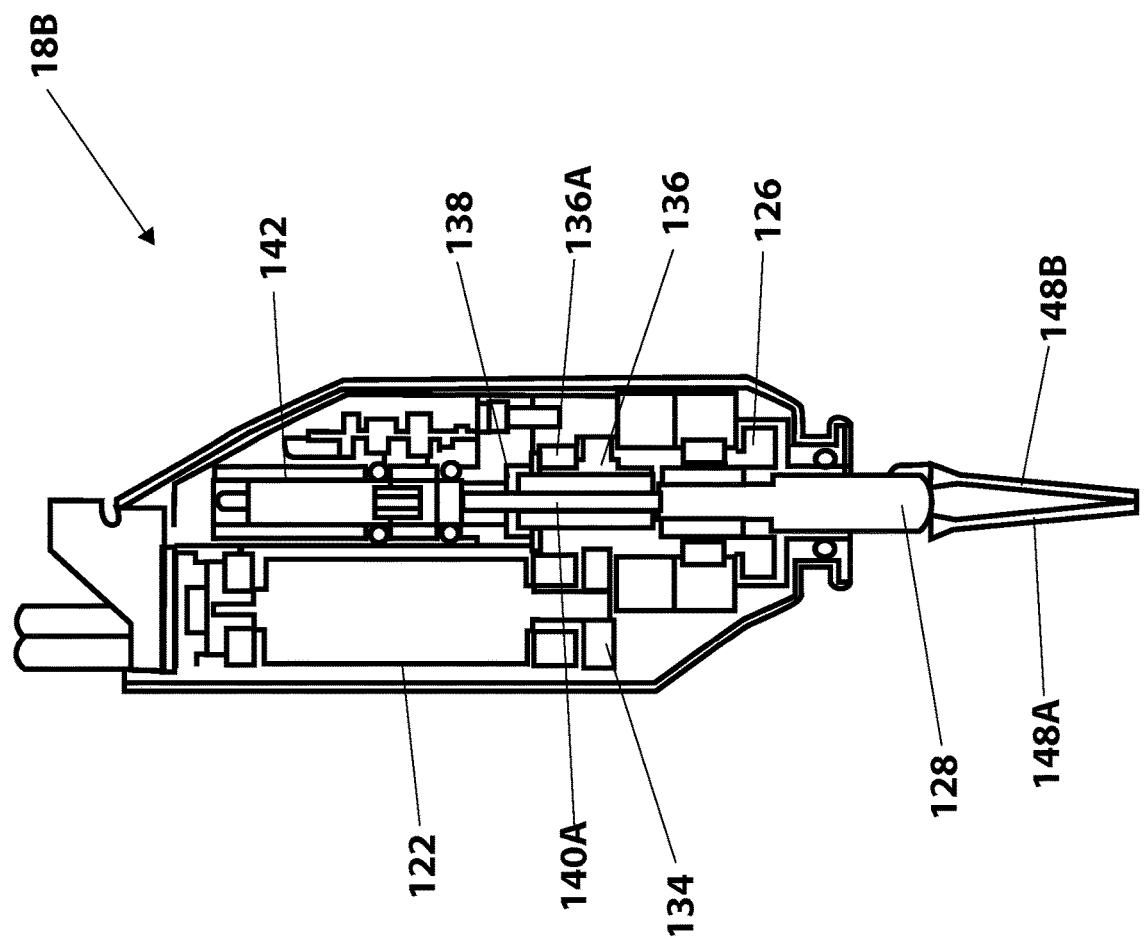
FIG. 9B is another cross-sectional sideview of the forearm of a robotic device, according to another embodiment.

The left forearm 18B has an end effector 26B that is a cautery grasper 26B, as shown in FIGS. 9A and 9B. According to one embodiment, the cautery grasper 26B is an integrated bi-polar cautery grasper 26B. In this context, "integrated" is intended to mean that the grasper 26B is an integral part of the forearm 18B such that replacement of the grasper 26B with another end effector would require disassembly of the forearm 18B. Alternatively, the grasper 26B is not an integral part of the forearm 18B but rather is easily removable and interchangeable with other end effectors. For example, in one embodiment, the end effector 26B is a "quick change" end effector 26B similar to the right end effector 26A as described above.

FIGS. 9A and 9B depict the left forearm 18B according to one implementation. FIG. 9A is a cross-sectional cutaway view of the forearm 18B along line DD-DD of FIG. 2D, while FIG. 9B is a cross-sectional cutaway view of the forearm along a line that is perpendicular to the plane of line DD-DD of FIG. 2D. The forearm 18B has two motors 120, 122. As best shown in FIG. 9A, the motor 120 is operably coupled to the end effector 26B such that the motor 120 actuates the end effector 26B to "roll," which is rotation around an axis parallel to the longitudinal length of the arm 18B. As best shown in FIG. 9B, the motor 122 is operably coupled to the end effector 26B such that the motor 122 actuates the end effector 26B to move between its open and closed positions.

Focusing on FIG. 9A, the motor 120 actuates the end effector 26B to roll in the following fashion. The motor 120 has a motor gear 124 that is operably coupled to a driven gear 126. The driven gear 126 is operably coupled to a end effector housing 128 such that the housing 128 rotates when the driven gear 126 rotates. As such, actuation of the motor 120 causes rotation of the end effector 26B. The at least one bearing 130 positioned around a proximal portion of the driven gear 126 to allow the gear 126 and the housing 128 to rotate in relation to the arm 18B. An O-Ring 132 forms a seal around the housing 128, but does not support the shaft and does not aid in its rotation or constraint. Applying a radial loaded to the O-ring 132 could potentially compromise the seal which is its primary and sole function.

Focusing on FIG. 9B, the motor 122 actuates the end effector 26B to open and close in the following fashion. The motor 122 has a motor gear 134 that is operably coupled to a driven gear 136. The driven gear 136 is operably coupled to a connector component 138, which is threadably coupled to an inner lumen 136A of the driven gear 136 such that the connector component 138 translates when the driven gear 136 rotates. The connector component 138 is operably coupled to connector rods 140A, 140B, which are operably coupled at their proximal ends to a slip ring 142 (as best shown in FIG. 9A). The connector component 138, rods 140A, 140B, and slip ring 142 are coupled to each other rotationally and axially such that rotation of the connector component 138 causes rotation of both the rods 140A, 140B and the slip ring 142. Further, as the driven gear 136 rotates, the assembly of the coupled components 138, 140A, 140B, 142 moves axially in relation to the driven gear 136. The assembly 138, 140A, 140B, 142 is also coupled to the end effector housing 128 such that housing 128 rotates when the assembly 138, 140A, 140B, 142 rotates. However, the assembly 138, 140A, 140B, 142 can move axially independently of the housing 128. Each of the rods 140A, 140B is operably coupled to one of the fingers 148A, 148B of the grasper 26B via a linkage (not shown) within the housing 128. As the rods 140A, 140B move axially, they move the linkages, thereby causing the fingers 148A, 148B to move between their open and closed positions. The driven gear 136 thus causes translation, not rotation of the assembly 138, 140, 142. Its rotation is contrained by the housing 128, which in turn is constrained by the driven gear 126, which in turn is rotationally constrained by motor gear 124, which is in turn constrained by motor 120. Therefore, it is the motor 120 that provides the rotational constraint in a similar fashion to the projection 90B in FIG. 8D. In contrast to the right arm, the linear motion and the rotational motion of this mechanism is coupled. When a user wishes to roll the tool and maintain a constant open or closed position, both motors 120, 122 must be actuated and match speed. When a user wishes to open or close the tool, the motor 122 must be actuated and hold position to constrain the rotation.

According to one embodiment, the forearm 18B also has a set of position sensors to provide information to an external controller (not shown) or a microcontroller regarding the position of the end effector 26B. In the implementation as shown in FIG. 9A, an array of LEDs 144 and a set of position sensors 146 are positioned in the forearm 18B such that the axial position of the end effector 26B can be determined based on the position of the slip ring 142. More specifically, the array of LEDs 144 are positioned on one side of the ring 142 and the sensors 146 are positioned on the other side such that the position of the slip ring 142 can be determined based on which sensors 146 are sensing light emitted from LEDs 144 (and which sensors 146 are not). This information about the position of the slip ring 142 can be used to determine the position of the end effector 26B.

Figure 10:
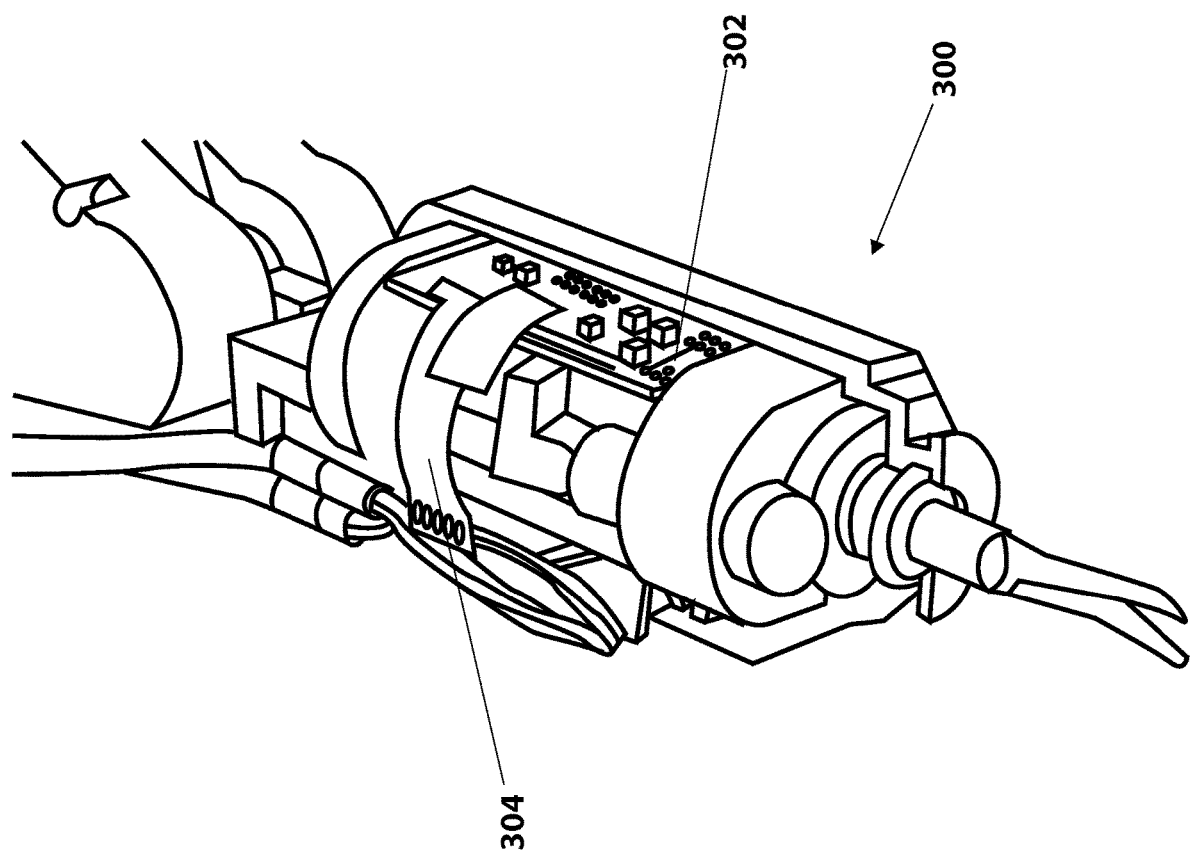
FIG. 10 is a perspective internal view of a forearm of a robotic device, according to another exemplary embodiment.

As best shown in FIG. 10, in certain exemplary embodiments of the present invention 300, the onboard microcontrollers, or PCBs 302, are operably connected with uniform flex tapes 304. In certain embodiments, the various PCBs are identical and the flex tapes are universally adaptable.

Figure 11A:
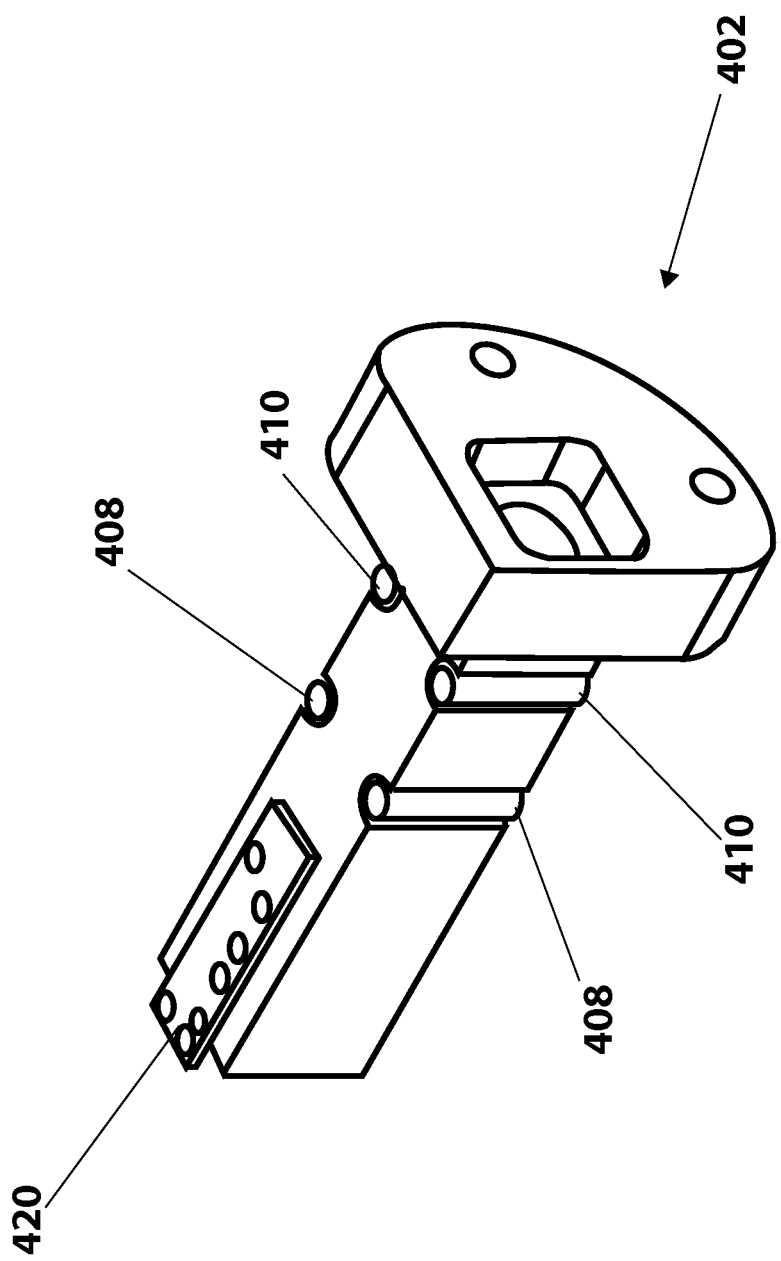
FIG. 11A contains a perspective view of an exemplary embodiment of the rotary slip ring assembly according to an exemplary embodiment.
Figure 11B:
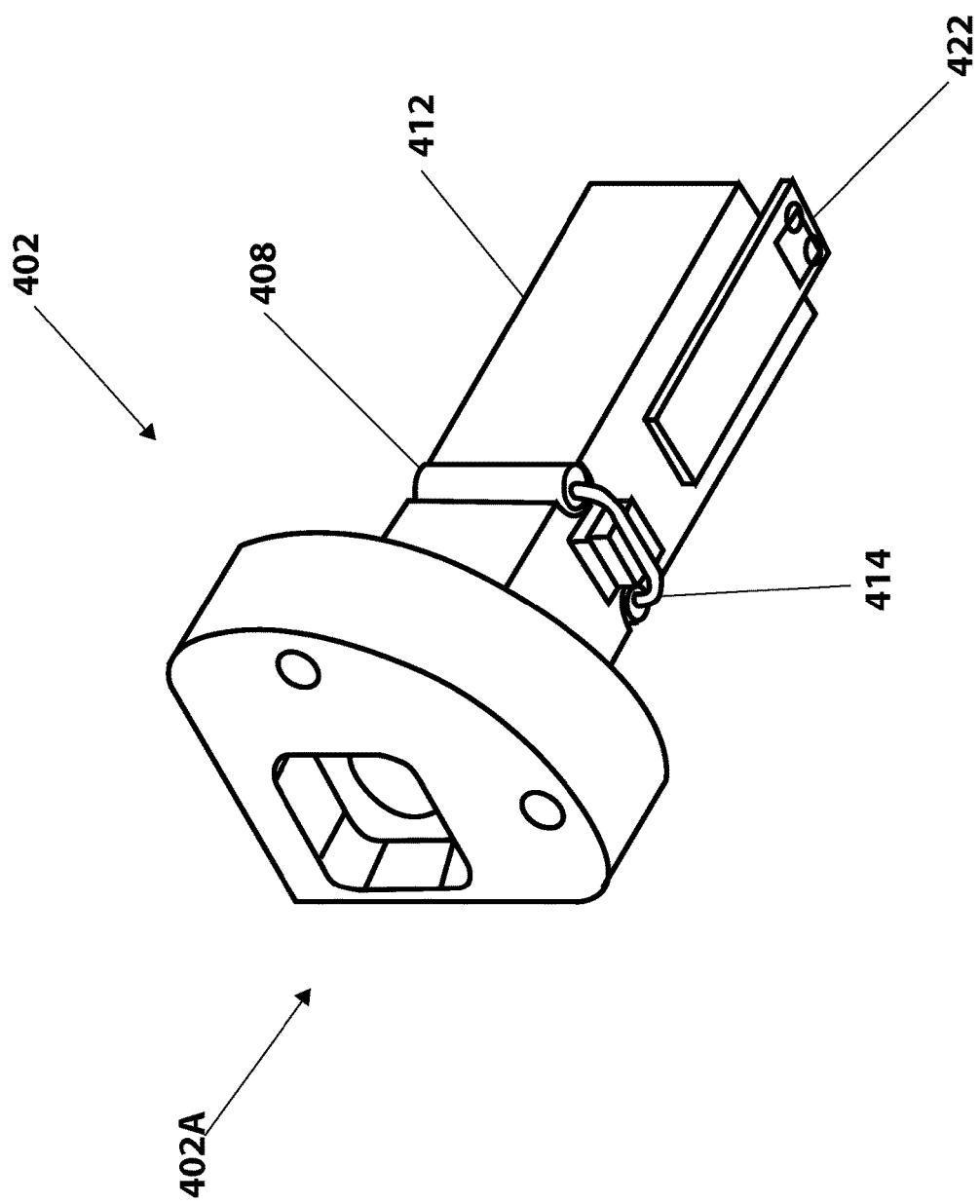
FIG. 11B contains another perspective view of an exemplary embodiment of the rotary slip ring assembly the embodiment of FIG. 11A.
Figure 11C:
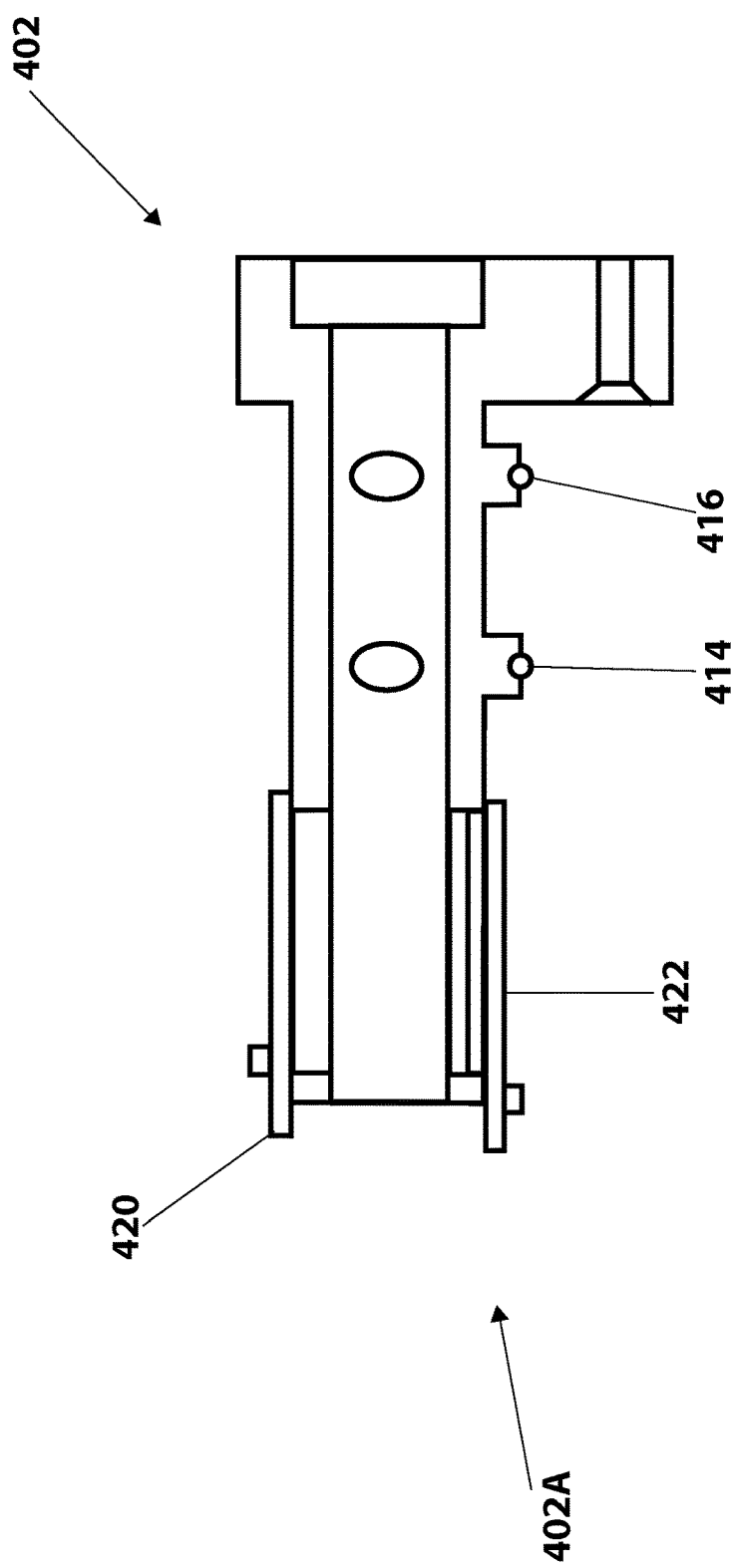
FIG. 11C is a cross sectional sideview of the rotary slip ring assembly the embodiment of FIG. 11A.
Figure 11E:
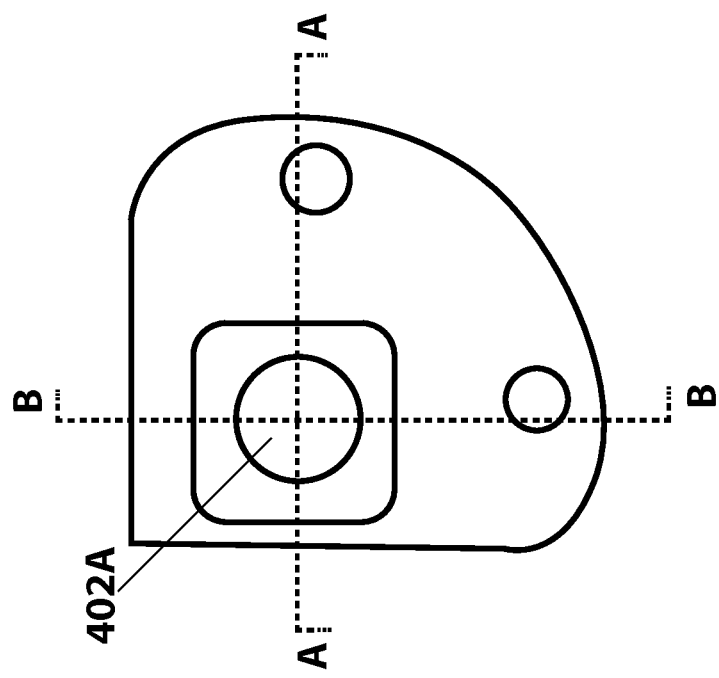
FIG. 11E is an endview of the embodiment of FIG. 11A.
Figure 12A:
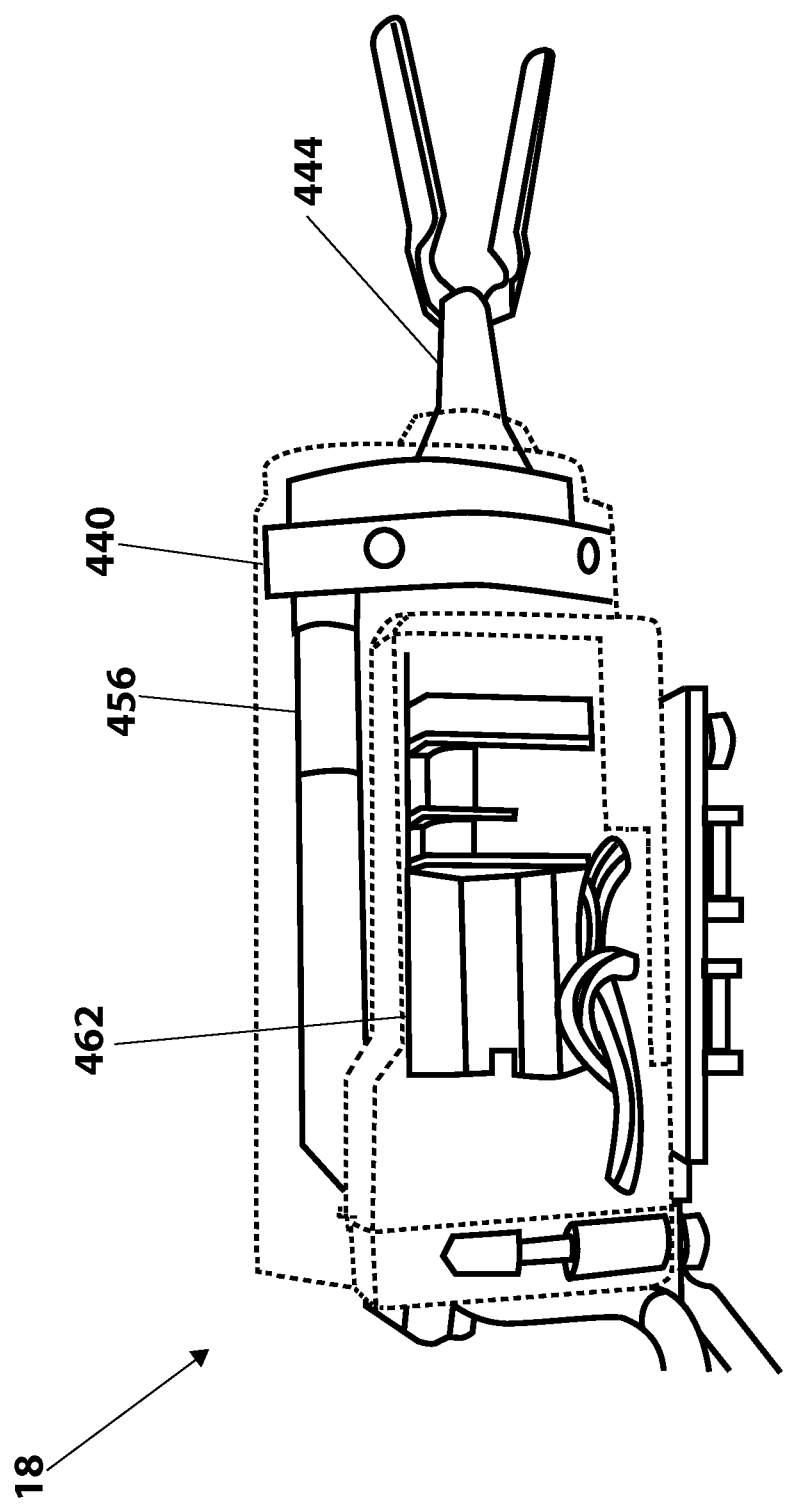
FIG. 12A is a cutaway sideview of an exemplary embodiment of the surgical device forearm and tool assembly.
Figure 12B:
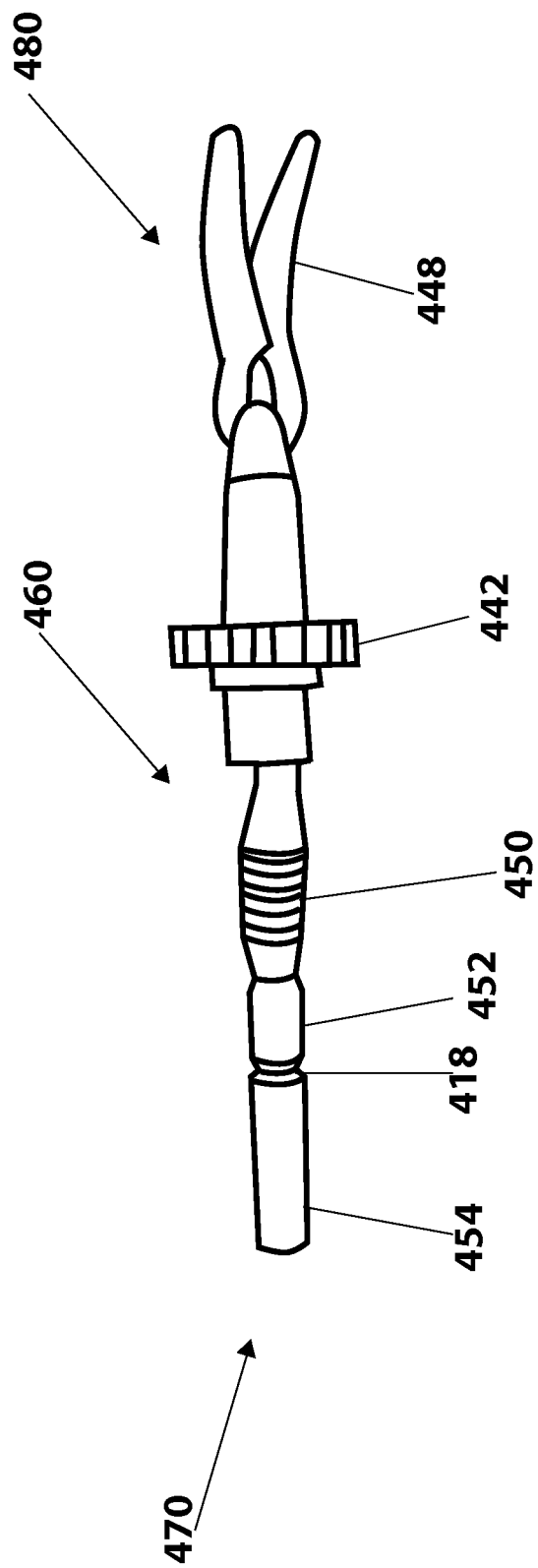
FIG. 12B is a side view of the tool assembly, according to an exemplary embodiment.
Figure 13A:
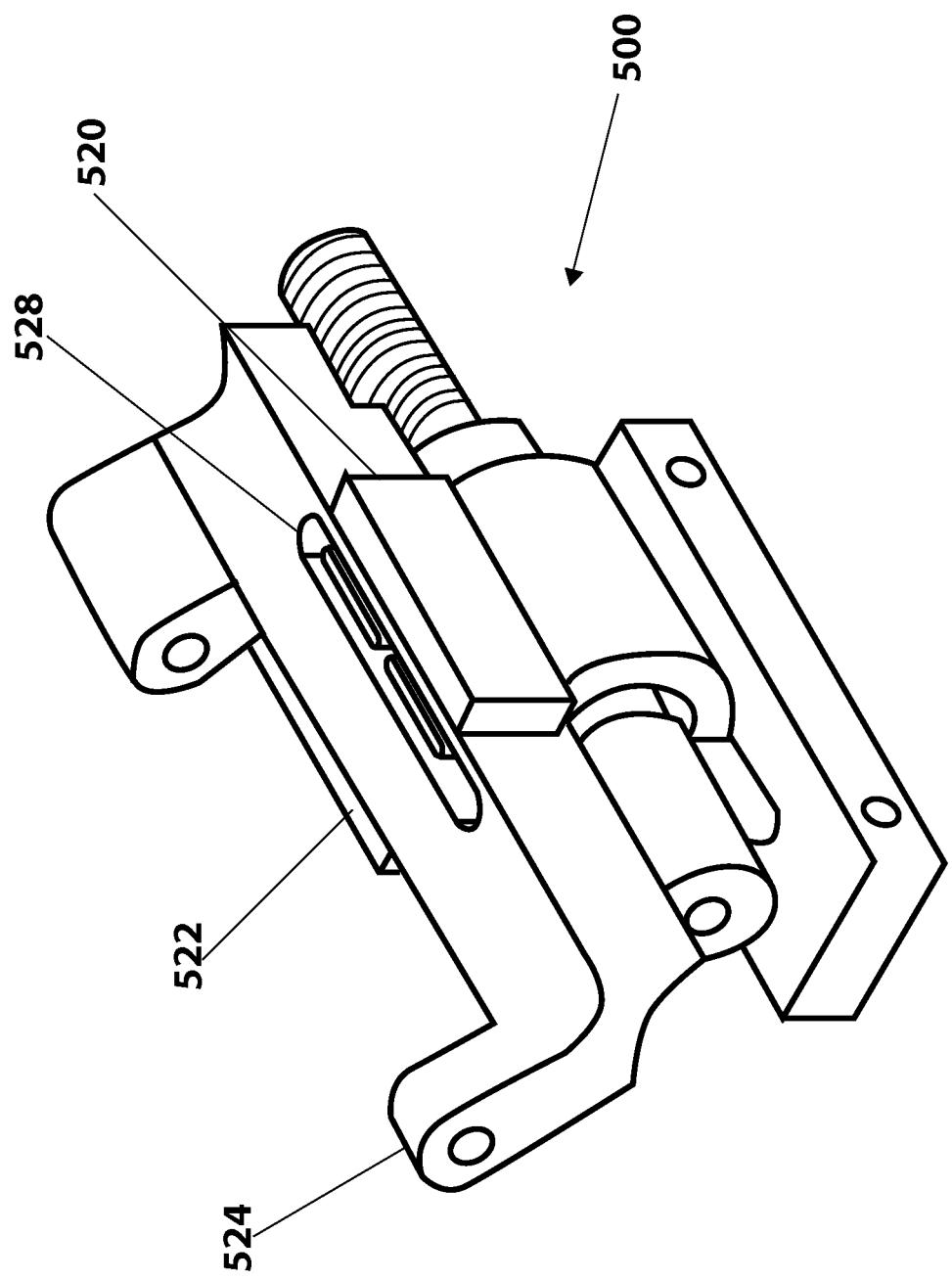
FIG. 13A is a perspective cutaway view of an exemplary embodiment of the surgical device forearm showing an embodiment of a linear encoder.
Figure 13B:
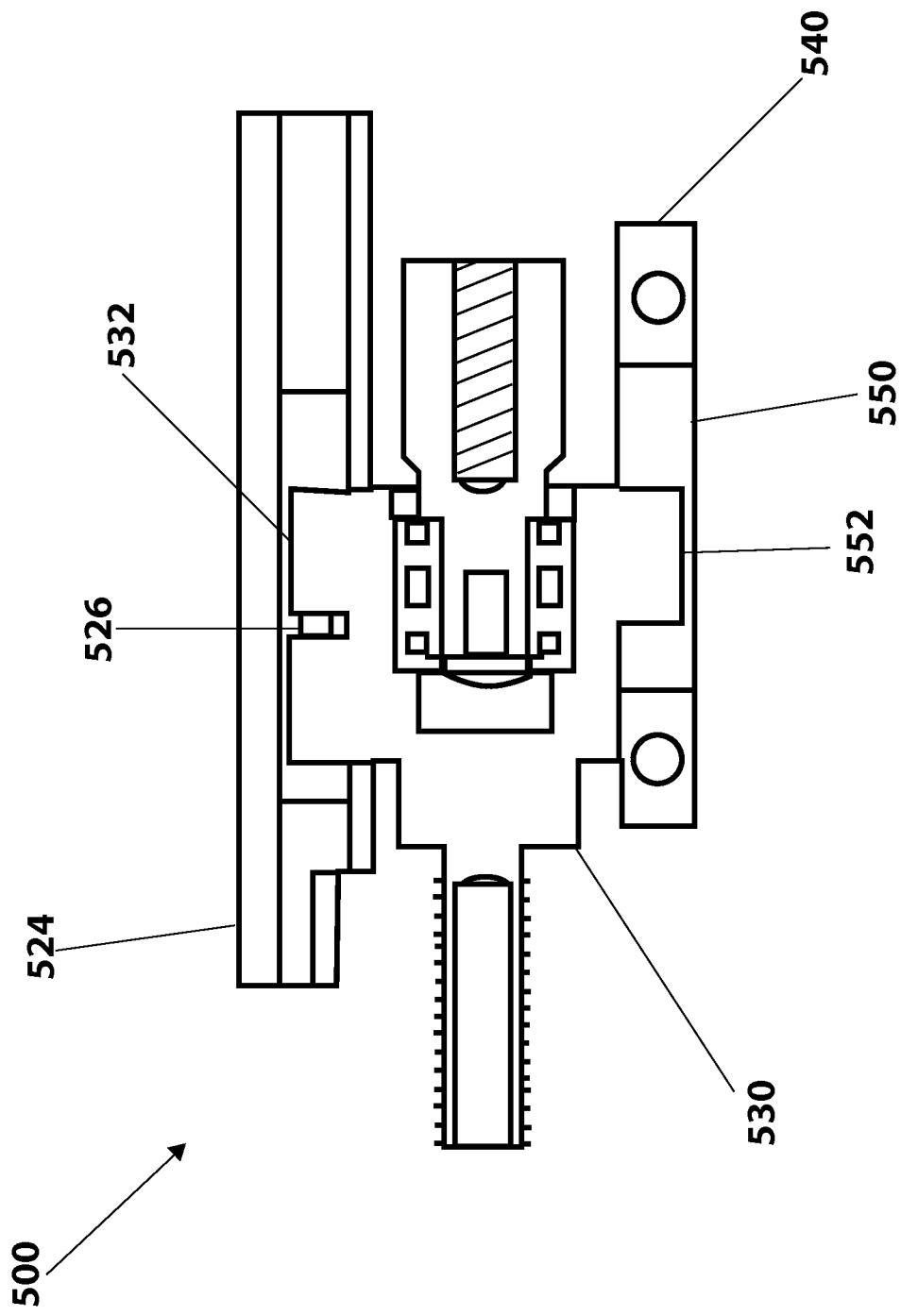
FIG. 13B is a cross-sectional sideview of the embodiment of a linear encoder according to FIG. 13A.
Figure 13C:
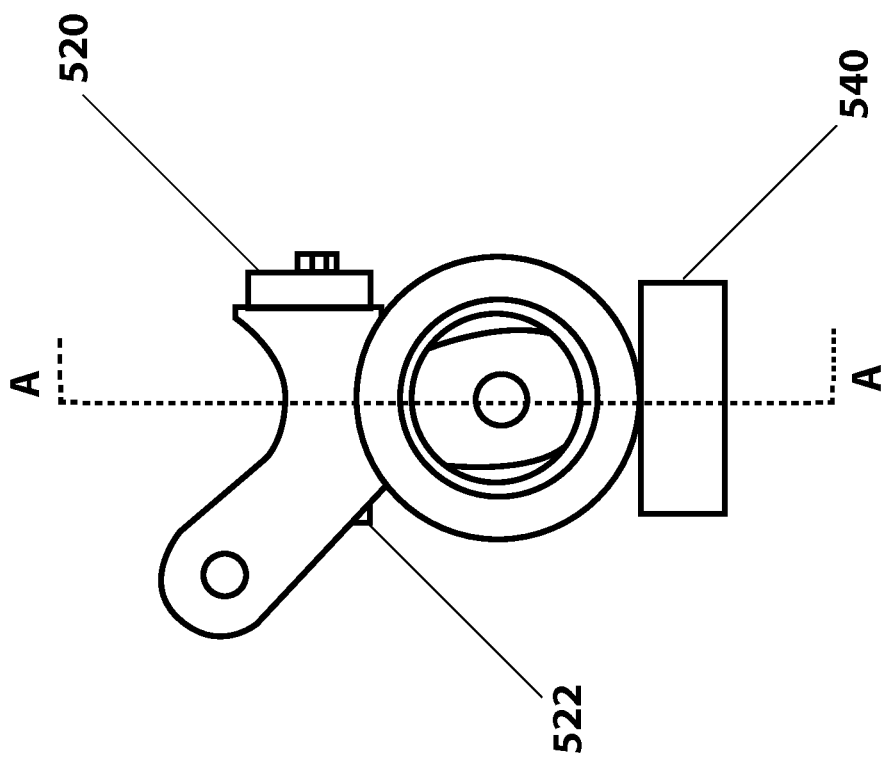
FIG. 13C is an end view of the embodiment of a linear encoder according to FIG. 13A and showing the cross section of FIG. 13B.
Figure 13D:
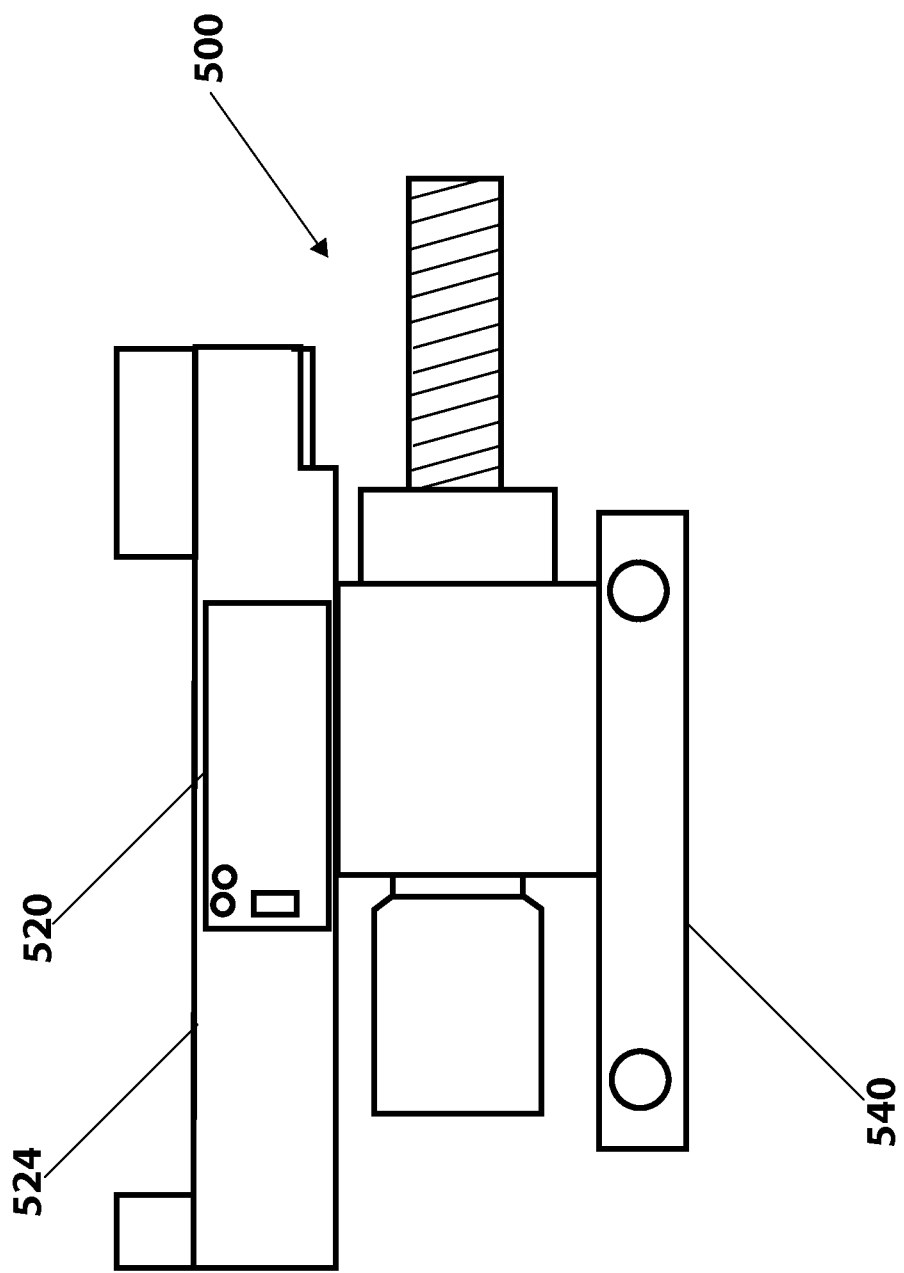
FIG. 13D is a sideview of the embodiment of a linear encoder according to FIG. 13A.

In certain exemplary embodiments of the forearm, 18 as shown in FIGS. 11A-11F and 12, the surgical device further comprises a linear slip ring assembly 402 (best shown in FIGS. 11A-11F) for use with an end effector, such as a bipolar cautery end effector, or "tool assembly" 460 which is shown generally in FIG. 12. In these embodiments, the bi-polar cautery end effector having two grasper fingers operates by coupling the two grasper fingers to separate electrical channels. The linear slip ring assembly 402 has an opening 402A that receives the tool assembly 460 (depicted in FIGS. 11F and 12) so as to provide electrical and mechanical communication between the tool assembly and the linear slip ring, and thereby couple the two grasper fingers to a power source. In certain embodiments, this is an external power source.

In certain implementations, the linear slip ring assembly 402 is a novel two-channel linear slip ring assembly 402 capable of allowing both rotating motion and translating motion of the tool assembly 460 disposed therein. The linear slip ring assembly also contains two electrical channels (as described below) that are isolated from one another throughout the assembly and connect to the linear slip ring 402 so as to pass bi-polar cautery power to the grasper fingers as they roll and open or close.

In exemplary embodiments, the linear slip ring assembly 402 has a first stator pair 408 and second stator pair 410. The first and second stator pairs 408, 410 are each spring loaded onto the housing 412 by U-springs 414, 416 and are operably coupled with the corresponding slip ring rotors 452, 454 of the tool assembly 460 (shown in FIG. 12). The slip ring rotors 452, 454 are capable of both translational and continuous rotation of the end effector. An insulator 418 separates the slip ring rotors 452, 454 to maintain electrical isolation.

Focusing on FIG. 12, in operation, exemplary end effector embodiments 440 having the linear slip ring assembly 440A further comprise a tool assembly 460 having a roll gear 442, which is permanently bonded to the tool housing 444. In operation, by rotating the roll gear 442, the tool housing assembly, 460 as described previously, all of the tool rotates. This rotation includes the grasper 448, the roll gear 442, the leadscrew 450, and the slip ring rotators 452, 454. In these embodiments, the roll gear 442 is fixed in place axially in the forearm assembly 440 and operably coupled to the roll motor 456. In these implementations, the roll gear 442 is not free to move linearly, and can only move rotationally. Actuating the roll motor 456 thus causes the entire tool assembly 460 to rotate.

In exemplary embodiments, a linear motor 462 is coupled to an internally threaded driven gear (shown in reference to FIG. 9B as the driven gear 136). This driven gear 136 is in turn threadably coupled to the connector component, or "leadscrew" 450 (shown in FIG. 9B as the connector component 138). The driven leadscrew drives the leadscrew 450 linearly so as to open and close the grasper 448.

Further, the leadscrew 450 and roll gear 442 are coupled together. In operation, in order to achieve pure roll, both the roll gear 442 and the driven leadscrew must rotate at the same speed. This is done so that there is no relative angular velocity between the leadscrew 450 and the leadscrew gear. By way of example, if the roll gear 442 were to spin (and the tool 460 spin with it), while the driven leadscrew gear maintained position, the leadscrew 450 would be spinning within the leadscrew gear and causing translation, in the depicted embodiment the opening or closing of the grasper 448.

Similarly, in order to achieve pure opening or closing of the grasper 448, the roll gear 442 must hold position while the driven leadscrew gear rotates and drives the leadscrew 450 linearly. If the roll gear 442 were free to spin while the driven leadscrew gear operates, no relative motion between the leadscrew 450 and leadscrew gear would occur and thus there would be no linear translation, and thus no opening or closing of the grasper 448.

In these exemplary embodiments, the cautery slip ring rotors 452, 454 are permanently coupled mechanically to the leadscrew 450 along an axis, but remain isolated 418 electrically from the leadscrew 450, such that the cautery slip ring rotors 452, 454 translate with the leadscrew 450 and rotated when entire tool 460 rotates.

Thus, in certain exemplary embodiments, the entire tool 460 is rotationally coupled. The proximal portion 470 (including the leadscrew 450 and the cautery slip ring rotors 452, 454) can translate with respect to the distal portion 480 (including the roll gear gear 442, the tool housing 440 and the grasper 448). This translation drives the grasper 448 open and closed. Further, and as discussed in relation to FIG. 11A-F, each of the cautery slip ring rotors 452, 454 is electrically coupled to one grasper jaw 448A, 448B. As previously discussed in reference to FIG. 11A-11F, each of the cautery slip ring rotors 452, 454 are also electrically coupled to a stator pair 408, 410, and is electrically isolated from every other element in the system.

According to another implementation, the surgical device forearm 18 further comprises a linear encoder, as is depicted in FIGS. 11A-F and discussed further herein in reference to 13A-D. Linear encoders serve as absolute position sensors by assessing the absolute position of the end effector or forearm. In these embodiments, the forearm 18 further comprises a pixel array 420 and LED array 422, as best shown in FIGS. 11A & 11B, which function together to determine the position of aspects of the surgical device. By way of example, in these embodiments, this functions is performed by broadcasting and receiving a signal—such as LED light—to determine the position of those aspects by assessing shadows or breaks in the LED light. Data from the magnetic absolute position encoder (discussed in relation to FIGS. 5C and 7B herein) and the linear position encoder can both be used as feedback sensors in the control algorithm. In certain implementations, the absolute linear position optical encoder is coupled to the gripper translation assembly and the custom relative rotary position optical encoder is coupled to the motor shaft, and both are used as the feedback sensors in the control algorithm. This is discussed further herein in relation to FIG. 13A-13D.

In the implementation shown in FIG. 11A-11F, an array of LEDs 422 and the pixel array 420 are positioned on the housing 412 such that the axial position of the end effector (not shown) can be determined based on the position of the projection from the LED array 422. More specifically, the array of LEDs on one side of the housing and the pixel array 420 are positioned on opposite sides of the housing 412 such that the position of the LED projection can be determined based on which sensors are sensing light emitted from LEDs (and which sensors are not) based on the position of the end effector disposed within that channel.

In certain embodiments, the motor control boards are integrated into the forearm housing, best shown as reference numbers 80 in FIGS. 8C and 122 in FIG. 9B. The linear position encoder is attached to the back of the tool drive motor. In certain embodiments, the surgical device comprises a rotary relative position encoder having a fan with a plurality of equally spaced blades operationally coupled to the dependant motor. As the dependant motor spins, these blades break a beam between an infrared sensor and receiver, thereby counting rotations of the motor.

Again, according to certain additional implementations, the surgical device has a linear encoder 500, as depicted in FIG. 13A-D. In these implementations, the LED emitter 522 is a PCB further comprising an array of LEDs. In these implementations, the receiver array 520 is also a PCB, and further comprises a linear array of light sensitive pixels. In certain implementations, the receiver array 520 comprises a COTS integrated circuit. In such exemplary embodiments, each element of output of the linear array 522 is continuously sampled by the receiver array 520 and the voltage level is recorded. By way of example, in these implementations, the voltage level is directly proportional to the amount of light collected by the pixel during the last sample period, such that increases in receive light correlates to increases in voltage, so as to communicate feedback concerning the absolute position of the surgical device and end effector.

In the exemplary embodiments of the linear encoder 500 depicted in FIGS. 13A-13D, the receiver array 520 and the LED emitter 522 are supported by a support piece 524 with at least one window (one labeled 526, others not shown), and a slit 528. According to one embodiment, the support piece 524 is made of machined delrin. The window 526 or windows allow light to pass from the LED emitter 522 to the receiver 520. The support piece 524 can accommodate a leadscrew 530. In certain implementations, the leadscrew 530 further comprises a slotted extrusion 532 which translates linearly to the slit 528. A gap in the extrusion 532 allows light to pass from the LED emitter 522 to the receiver 520. As the leadscrew 530 translates, the slot in extrusion 532 moves correspondingly, thereby casting a shadow on the receiver everywhere except in the location of the slot. In this way, absolute position of the leadscrew 530 is determined.

In certain implementations, a second extrusion 552 slides in a slot 550 in the second support piece 540. This slot 550 has a tighter fit than between the slotted extrusion 532 and slot 528. In this way the second support piece 540 can act as the rotational constraint for the leadscrew 530. In this implementation, the second extrusion 552 causes friction (or "rubs") against the second support piece 540 and slot 550. Conversely, the slotted extrusion 532 does not rub in slot 528. This implementation prevents material build up, deformation, or other deterioration of the sensor unit.

Thus, certain embodiments of the present invention provide redundant position sensing. For example, each forearm may have a relative position sensor. In these embodiments, each forearm also may further comprise an absolute position encoder. As would be apparent to those of skill in the art, the coupling of the absolute and relative position sensing allows for both homing of the device and the addition of safety features.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

Although the present invention has been described with reference to preferred embodiments, persons skilled in the art will recognize that changes may be made in form and detail without departing from the spirit and scope of the invention.

What is claimed is:

1. A robotic device, comprising:
   a. a connector comprising:
      i. a first coupleable body comprising at least one first connector motor;
      ii. a second coupleable body comprising at least one second connector motor; and
      iii. a lumen defined within the connector and sized to accept a laparoscopic imaging device;
   b. a first segmented robotic arm in operational communication with the first coupleable body and first connector motor, the first segmented robotic arm comprising:
      i. a first upper arm in operable and rotational communication with the first coupleable body, the first upper arm comprising a first upper arm housing containing:
         A. a plurality of first upper arm motors; and
         B. a first upper arm motor control board;
      ii. a first forearm in operable and rotational communication with the first upper arm, the first forearm having a first forearm housing containing:
         A. a plurality of first forearm motors;
         B. a first forearm motor control board; and
         C. a first end effector housing defined in the first forearm housing;
   c. a second segmented robotic arm in operational communication with the second coupleable body and second connector motor, the second segmented robotic arm comprising:
      i. a second upper arm in operable and rotational communication with the second coupleable body, the second upper arm comprising a second upper arm housing containing:
         A. a plurality of second upper arm motors; and
         B. a second upper arm motor control board;
      ii. a second forearm in operable and rotational communication with the second upper arm, the second forearm having a second forearm housing containing:
         A. a plurality of second forearm motors;
         B. a second forearm motor control board; and
         C. a second end effector housing defined in the second forearm housing;
   d. a first end effector in operational communication with the first segmented robotic arm via the first end effector housing; and
   e. a second end effector in operational communication with the second segmented robotic arm via the second end effector housing,
   wherein:
      i. the first coupleable body further comprises a notch;
      ii. the second coupleable body further comprises a projection; and
      iii. the notch and the projection are designed to be operationally communicable.

2. The surgical device of claim 1, further comprising an LED array disposed within the first forearm housing.

3. The surgical device of claim 1, further comprising an absolute position sensor disposed within the first forearm housing.

4. A modular surgical device comprising:
   a. a connector comprising:
      i. a first coupleable body enclosing at least one motor control board;

ii. a second coupleable body;
iii. two or more connector motors disposed within the first or second coupleable body and in operational communication with the at least one motor control board;
iv. a lumen defined within the connector and sized to accept a laparoscopic imaging device,
wherein the first coupleable body is constructed and arranged to be coupled to the second coupleable body;
b. a first segmented robotic arm in operational communication with at least one of the two or more connector motors, the first segmented robotic arm comprising:
i. a first upper arm comprising a first upper arm housing containing:
A. a plurality of first upper arm motors; and
B. a first upper arm motor control board;
ii. a first forearm in operable and rotational communication with the first upper arm, the first forearm having a first forearm housing containing:
A. a plurality of first forearm motors;
B. a first forearm motor control board; and
C. a first end effector housing defined in the first forearm housing;
c. a second segmented robotic arm in operational communication with at least one of the two or more connector motors, the second segmented robotic arm comprising:
i. a second upper arm comprising a second upper arm housing containing:
A. a plurality of second upper arm motors; and
B. a second upper arm motor control board;
ii. a second forearm in operable and rotational communication with the second upper arm, the second forearm having a second forearm housing containing:
A. a plurality of second forearm motors;
B. a second forearm motor control board; and
C. a second end effector housing defined in the second forearm housing;
d. a first end effector in operational communication with the first segmented robotic arm via the first end effector housing;
e. a second end effector in operational communication with the second segmented robotic arm via the second end effector housing; and
f. first and second connection lines, one for each segmented robotic arm,
thereby allowing for independent operation of the segmented robotic arms.

5. The surgical device of claim 4, further comprising at least one irrigation line.

6. The surgical device of claim 4, wherein the connector comprises a first coupling body and a second coupling body.

7. The surgical device of claim 6, wherein the first coupleable body and second coupleable body are mateable to form a single body.

8. The surgical device of claim 7, wherein the first coupleable body comprises a first mating feature and the second coupleable body comprises a second mating feature.

9. The surgical device of claim 8, wherein the first mating feature is a notch and the second mating feature is a projection.

10. A modular surgical device comprising:
a. a connector comprising:
i. a first body portion comprising at least one motor control board in electrical communication with two or more connector motors disposed within the first body portion;
ii. a second body portion; and
iii. a lumen defined within the connector and sized to accept a laparoscopic imaging device,
wherein the first body portion is constructed and arranged to be coupled to the second body portion;
b. a first segmented robotic arm in operational communication with at least one of the two or more connector motors, the first segmented robotic arm comprising:
i. a first upper arm comprising a first upper arm housing containing:
A. a plurality of first upper arm motors; and
B. a first upper arm motor control board;
ii. a first forearm in operable and rotational communication with the first upper arm, the first forearm having a first forearm housing containing:
A. a plurality of first forearm motors;
B. a first forearm motor control board; and
C. a first end effector housing defined in the first forearm housing;
c. a second segmented robotic arm in operational communication with at least one of the two or more connector motors, the second segmented robotic arm comprising:
i. a second upper arm comprising a second upper arm housing containing:
A. a plurality of second upper arm motors; and
B. a second upper arm motor control board;
ii. a second forearm in operable and rotational communication with the second upper arm, the second forearm having a second forearm housing containing:
A. a plurality of second forearm motors;
B. a second forearm motor control board; and
C. a second end effector housing defined in the second forearm housing;
d. a first end effector in operational communication with the first segmented robotic arm via the first end effector housing; and
e. a second end effector in operational communication with the second segmented robotic arm via the second end effector housing,
wherein the first and second body portions and segmented robotic arms are constructed and arranged so as to operate independently in an uncoupled state.

11. The surgical device of claim 10, wherein the first end effector is chosen from a group consisting of a grasping component, a cauterizing component, a suturing component, an imaging component, an irrigation component, a suction component, an operational arm component, a sensor component, and a lighting component.

12. The surgical device of claim 10, wherein the second end effector is chosen from a group consisting of a grasping component, a cauterizing component, a suturing component, an imaging component, an irrigation component, a suction component, an operational arm component, a sensor component, and a lighting component.

13. The surgical device of claim 10, wherein the robotic device further comprises at least one absolute position sensor.

14. The surgical device of claim 13, wherein the at least one absolute position sensor is selected from the group consisting of a magnetic absolute position encoder and a linear encoder.

15. The surgical device of claim 10, further comprising a pixel array and an LED array.

\* \* \* \* \*